(12) United States Patent
Gollin et al.

(10) Patent No.: US 9,080,216 B2
(45) Date of Patent: *Jul. 14, 2015

(54) GENETIC CHANGES IN ATM AND ATR/CHEK1 AS PROGNOSTIC INDICATORS IN CANCER

(71) Applicant: University of Pittsburgh-of the CommonWealth System of Higher Education, Pittsburgh, PA (US)

(72) Inventors: Susanne M. Gollin, Pittsburgh, PA (US); Rahul Atul Parikh, Pittsburgh, PA (US); Xin Huang, Wexford, PA (US)

(73) Assignee: University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,745

(22) Filed: Apr. 23, 2013

(65) Prior Publication Data

US 2014/0088169 A1    Mar. 27, 2014

Related U.S. Application Data

(60) Continuation of application No. 13/407,165, filed on Feb. 28, 2012, now Pat. No. 8,466,123, which is a division of application No. 12/586,052, filed on Sep. 15, 2009, now Pat. No. 8,173,366, which is a continuation-in-part of application No. 12/079,900, filed on Mar. 28, 2008, now Pat. No. 8,263,329.

(60) Provisional application No. 60/908,891, filed on Mar. 29, 2007, provisional application No. 60/912,086, filed on Apr. 16, 2007, provisional application No. 60/912,355, filed on Apr. 17, 2007.

(51) Int. Cl.
| | |
|---|---|
| *C12Q 1/68* | (2006.01) |
| *A61K 31/7088* | (2006.01) |
| *A61K 31/7105* | (2006.01) |
| *A61K 45/06* | (2006.01) |
| *G01N 33/574* | (2006.01) |

(52) U.S. Cl.
CPC .......... *C12Q 1/6886* (2013.01); *A61K 31/7088* (2013.01); *A61K 31/7105* (2013.01); *A61K 45/06* (2013.01); *G01N 33/57407* (2013.01); *C12Q 1/6841* (2013.01); *C12Q 2600/106* (2013.01); *G01N 2333/91215* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,173,366 | B2 | 5/2012 | Gollin et al. |
| 8,263,329 | B2 | 9/2012 | Gollin et al. |
| 8,466,123 | B2 | 6/2013 | Gollin et al. |
| 2005/0191632 | A1 | 9/2005 | Byrd et al. |
| 2006/0205020 | A1 | 9/2006 | Carr |
| 2006/0216747 | A1 | 9/2006 | McSwiggen et al. |
| 2008/0145358 | A1 | 6/2008 | Zabludoff et al. |
| 2010/0173971 | A1 | 7/2010 | Gollin et al. |
| 2010/0324112 | A1 | 12/2010 | Gollin et al. |
| 2012/0295951 | A1 | 11/2012 | Gollin et al. |
| 2013/0338212 | A1 | 12/2013 | Gollin et al. |

OTHER PUBLICATIONS

U.S. Appl. No. 12/586,052, Apr. 12, 2012 Decision on Petition.
U.S. Appl. No. 12/586,052, Apr. 2, 2012 Amendment after Notice of Allowance and Petition filed.
U.S. Appl. No. 12/586,052, Feb. 27, 2012 Issue Fee payment.
U.S. Appl. No. 12/586,052, Feb. 1, 2011 Notice of Allowance.
U.S. Appl. No. 12/586,052, Sep. 26, 2011 Amendment and Request for Continued Examination (RCE).
U.S. Appl. No. 12/586,052, Jul. 27, 2011 Final Office Action.
U.S. Appl. No. 12/586,052, May 5, 2011 Response to Non-Final Office Action.
U.S. Appl. No. 12/586,052, Mar. 25, 2011 Examiner Interview Summary.
U.S. Appl. No. 12/586,052, Nov. 26, 2010 Non-Final Office Action.
U.S. Appl. No. 12/586,052, Oct. 14, 2010 Response to Restriction Requirement.
U.S. Appl. No. 12/586,052, Sep. 17, 2010 Restriction Requirement.
U.S. Appl. No. 12/079,900, Aug. 2, 2012 Decision on Petition.
U.S. Appl. No. 12/079,900, Jul. 17, 2012 Amendment after Notice of Allowance.
U.S. Appl. No. 12/079,900, May 24, 2012 Issue Fee payment.
U.S. Appl. No. 12/079,900, Mar. 12, 2012 Applicant Summary of Interview with Examiner.
U.S. Appl. No. 12/079,900, Feb. 29, 2012 Notice of Allowance.
U.S. Appl. No. 12/079,900, Nov. 25, 2011 Non-Final Office Action.
U.S. Appl. No. 12/079,900, Sep. 19, 2011 Amendment and Request for Continued Examination (RCE).
U.S. Appl. No. 12/079,900, Jul. 20, 2011 Final Office Action.
U.S. Appl. No. 12/079,900, May 5, 2011 Response to Non-Final Office Action.
U.S. Appl. No. 12/079,900, Mar. 25, 2011 Examiner Interview Summary.
U.S. Appl. No. 12/079,900, Feb. 3, 2011 Non-Final Office Action.
U.S. Appl. No. 12/079,900, Nov. 24, 2010 Response to Restriction Requirement.

(Continued)

*Primary Examiner* — Kimberly Chong
(74) *Attorney, Agent, or Firm* — Baker Botts, LLP

(57) ABSTRACT

The present invention relates to the discovery that, in human cancer, an 11q deletion of ATM together with an increase in ATR and CHEK1 expression correlates with resistance to ionizing radiation which could be overcome by inhibition of the ATR/CHEK1 pathway. It provides for methods of identifying patients unlikely to exhibit an adequate response to radiation therapy and/or chemotherapy who may benefit from ATR/CHEK1 pathway inhibition, as well as methods of treating said patients.

Figure 1:
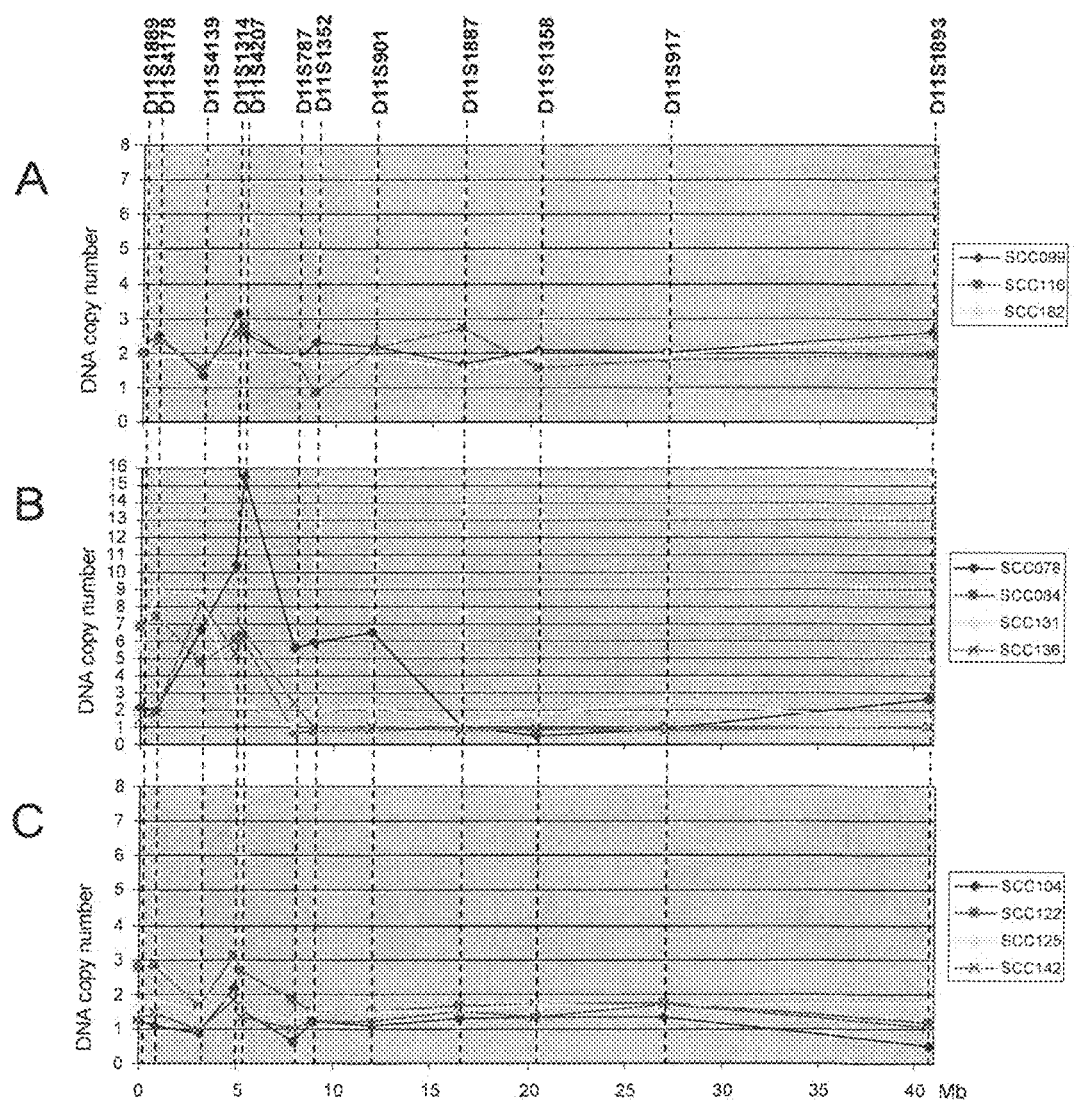

10 Claims, 43 Drawing Sheets
(20 of 43 Drawing Sheet(s) Filed in Color)

(56) References Cited

OTHER PUBLICATIONS

U.S. Appl. No. 12/079,900, Nov. 4, 2010 Restriction Requirement.
U.S. Appl. No. 13/407,165, May 16, 2013 Decision on Petition.
U.S. Appl. No. 13/407,165, Apr. 23, 2013 Issue Fee payment.
U.S. Appl. No. 13/407,165, Jan. 24, 2013 Notice of Allowance.
U.S. Appl. No. 13/407,165, Jan. 8, 2013 Response to Non-Final Office Action.
U.S. Appl. No. 13/407,165, Oct. 9, 2012 Non-Final Office Action.
U.S. Appl. No. 13/407,165, Sep. 27, 2012 Response to Restriction Requirement.
U.S. Appl. No. 13/407,165, 8/30/212 Restriction Requirement.
U.S. Appl. No. 13/480,358, Jun. 10, 2013 Issue Fee payment.
U.S. Appl. No. 13/480,358, Mar. 18, 2013 Notice of Allowance.
U.S. Appl. No. 13/480,358, Mar. 5, 2013 Response to Final Office Action.
U.S. Appl. No. 13/480,358, Feb. 11, 2013 Final Office Action.
U.S. Appl. No. 13/480,358, Jan. 14, 2013 Response to Non-Final Office Action.
U.S. Appl. No. 13/480,358, Oct. 12, 2012 Non-Final Office Action.
U.S. Appl. No. 13/480,358, 10/2/212 Response to Restriction Requirement.
U.S. Appl. No. 13/480,358, 9/17/212 Restriction Requirement.
U.S. Appl. No. 13/914,321, Jan. 28, 2014 Response to Non-Final Office Action.
U.S. Appl. No. 13/914,321, Nov. 7, 2013 Non-Final Office Action.
Abraham "Cell cycle checkpoint signaling through the ATM and ATR kinases" 2001, *Genes. Dev.* 15(17), 2177-96.
Akervall et al. "Amplification of cyclin D1 in squamous cell carcinoma of the head and neck and the prognostic value of chromosomal abnormalities and cyclin D1 overexpression" 1997, *Cancer*, 79(3):80-389.
Albertson et al. "Chromosome aberrations in solid tumors" 2003, *Nat. Genet.*, 34:369-76.
Ashman et al. "Prognostic value of genomic alterations in head and neck squamous cell carcinoma detected by comparative genomic hybridisation" 2003, *Br. J. Cancer*, 89:5:864-9.
Austen et al. "Mutation status of the residual ATM allele is an important determinant of the cellular response to chemotherapy and survival in patients with chronic lymphocytic leukemia containing an 11q deletion" 2007, *J. Clin. Onc.*, 25(34):5448-57.
Bakkenist et al. "DNA damage activates ATM through intermolecular autophosphorylation and dimer dissociation" 2003, *Nature*, 421(6922):499-506.
Baocheng et al. "Fhit and CHEK1 have opposing effects on homologous recombination repair" 2005, *Cancer Res.*, 65(19):8613-6.
Bartek et al. "CHEK1 and Chk2 kinases in checkpoint control and cancer" 2003, *Cancer Cell*, 3(5):421-9.
Bartkova et al. "Abnormal patterns of D-type cyclin expression and G1 regulation in human head and neck cancer" 1995, *Cancer Res.*, 55(4):949-56.
Bartkova et al. "DNA damage response as a candidate anti-cancer barrier in early human tumorigenesis" 2005, *Nature*, 434:864-870.
Bassing et al. "Histone H2AX: a dosage-dependent suppressor of oncogenic translocations and tumors" 2003, *Cell*, 114(3):359-70.
Bernard et al. "Molecular basis of 11q23 rearrangements in hematopoietic malignant proliferations" 1995, *Genes. Chromosomes Cancer*,13(2):75-85.
Bi et al. "Telomere protection without a telomerase; the role of ATM and Mre11 in *Drosophila* telomere maintenance" 2004, *Curr. Biol.*, 14(15):1348-53.
Bockmuhl et al. "Chromosomal alterations during metastasis formation of head and neck squamous cell carcinoma" 2002, *Genes Chromosomes Cancer*, 33(1):29-35.
Bolt et al. The ATM/p53 pathway is commonly targeted for inactivation in squamous cell carcinoma of the head and neck (SCCHN) by multiple molecular mechanisms 2005, *Oral Oncol.*, 41(10):1013-20.
Broeks et al. "ATM-heterozygous germline mutations contribute to breast cancer-susceptability" 2000, *Am. J. Hum. Genet.*, 66(2):494-500.
Broustas et al. "BRCC2, a novel BH3-like domain-containing protein, induces apoptosis in a caspase-dependent manner" 2004, *J. Biol. Chem.*, 279(25):26780-8.
Brown et al. "Essential and dispensable roles of ATR in cell cycle arrest and genome maintenance" 2003, *Genes. Dev.*, 17(5):615-28.
Burma et al. "ATM phosphorylates histone H2AX in response to DNA double-strand breaks" 2001, *J. Biol. Chem.*, 276(45):42462-7.
Busby et al. "The radiosensitizing agent 7-hydroxystaurosporine (UCN-01) inhibits the DNA damage checkpoint kinase hCHEK1" 2000, *Cancer Res.*, 60(8):2108-12.
Byun et al. "Functional uncoupling of MCM helicase and DNA polymerase activities activates the ATR-dependent checkpoint" 2005, *Genes. Dev.*, 19(9):1040-52.
Cabral et al. "Distinct functional interactions of human Skn-1 isoforms with Ese-1 during keratinocyte terminal differentiation" 2003, *J. Biol. Chem.*,278(20):17792-9.
Casper et al. "ATR regulates fragile site stability" 2002, *Cell*, 111(6):779-89.
Celeste et al. "H2AX haploinsufficiency modifies genomic stability and tumor susceptibility" 2003, *Cell*, 114(3):371-83.
Chen et al. "Selective Chk1 inhibitors differentially sensitize p53-deficient cancer cells to cancer therapeutics" 2006, *Int. J. Cancer* 119:2784-94.
Cheng et al. "The cell cycle checkpoint gene Rad9 is a novel oncogene activated by 11q13 amplification and DNA methylation in breast cancer" 2005, *Cancer Res.*, 65(19):8646-54.
Ciapponi et al. "The *Drosophila* Mre11/Rad50 complex is required to prevent both telomeric fusion and chromosome breakage" 2004, *Curr. Biol.*, 14:1360-6.
Cortez et al. "ATR and ATRIP: partners in checkpoint signaling" 2001, *Science*, 294(5547):1713-6.
Cuadrado et al. "ATM regulates ATR chromatin loading in response to DNA double-strand breaks" 2006, *J. Exp. Med.*, 203(2):297-303.
Dahiya et al. "Deletion of chromosome 11p15, p12, q22, q23-24 loci in human prostate cancer" 1997, *Int. J. Cancer*, 72:283-8.
De Klein et al. "Targeted disruption of the cell-cycle checkpoint gene ATR leads to early embryonic lethality in mice" 2000, *Curr. Biol.*, 10(8):479-82.
Dickson et al. "Human keratinocytes that express hTERT and also bypass a p16(INK4a)-enforced mechanism that limits life span become immortal yet retain normal growth and differentiation characteristics" 2000, *Mol. Cell Biol.*, 20(4):1436-47.
Elbashir et al. "Duplexes of 21-nucleotide RNAs mediate RNA interference in cultured mammalian cells" 2001, *Nature*, 411:494-8.
Evans et al. "Allelic deletion at 11q23.3-q25 is an early event in cervical neoplasia" 1998, *Oncogene*, 16:2557-64.
Fedier et al. "Loss of atm sensitises p53-deficient cells to topoisomerase poisons and antimetabolites" 2003, *Ann. Oncol.*, 14:938-45.
Fracchiolla et al. "Molecular and immunohistochemical analysis of the bcl 1 /cyclin D1 gene in laryngeal squamous cell carcinomas: Correlation of protein expression with lymph node metastases and advanced clinical stage" 1997, *Cancer*, 79(6):1114-21.
Gatti et al. "Ataxia-telangiectasia: an interdisciplinary approach to pathogenesis" 1991, *Medicine* (Baltimore), 70(2):99-117.
Genbank Acc. No. NM_001184, Mar. 24, 1999.
Genbank Acc. No. NM_001274, Mar. 24, 1999.
Genbank Acc. No. NM_053056, Nov. 16, 2001.
Gisselsson "Chromosome instability in cancer: how, when, and why?" 2003, *Adv. Cancer Res.*, 87:1-29.
Gisselsson et al. "Centrosomal abnormalities, multipolar mitoses, and chromosomal instability in head and neck tumours with dysfunctional telomeres" 2002, *Br. J. Cancer*, 87(2):202-7.
Golding et al. "Double strand break repair by homologous recombination is regulated by cell cycle-independent signaling via ATM in human glioma cells" 2004, *J. Biol. Chem.*, 279:15402-10.
Gollin "Chromosomal alterations in squamous cell carcinomas of the head and neck: window to the biology of disease" 2001, *Head Neck*, 23:238-53.
Gorgoulis et al. "Activation of the DNA damage checkpoint and genomic instability in human precancerous lesions" 2005, *Nature*, 434(7035):907-13.

(56) References Cited

OTHER PUBLICATIONS

Graves et al. "The CHEK1 protein kinase and the Cdc25C regulatory pathways are targets of the anticancer agent UCN-01" 2000, *J. Biol. Chem.*, 275(8):5600-5.
Hammond et al. "ATR/ATM targets are phosphorylated by ATR in response to hypoxia and ATM in response to reoxygenation" 2003, *J. Biol. Chem.*, 278(14):12207-13.
Hammond et al. "Inhibition of ATR leads to increased sensitivity to hypoxia/reoxygenation" 2004, *Cancer Res.*,64(18):6556-62.
Hekmat-Nejad et al. "Xenopus ATR is a replication-dependent chromatin-binding protein required for the DNA replication checkpoint" 2000, *Curr. Biol.*, 10:1565-73.
Helt et al. "Ataxia telangiectasia mutated (ATM) and ATM and Rad3-related protein exhibit selective target specificities in response to different forms of DNA damage" 2005, *J. Biol. Chem.*, 280(2):1186-92.
Holm "Cellular DNA amounts of squamous cell carcinomas of the head and neck region in relation to prognosis" 1982, *Laryngoscope*, 92(9 Pt 1):1064-9.
Huang et al. "Comprehensive genome and transcriptome analysis of the 11q13 amplicon in human oral cancer and synteny to the 7F5 amplicon in murine oral carcinoma" 2006, *Genes Chromosomes Cancer*, 45:1058-1069.
Huang et al. "High-resolution mapping of the 11q13 amplicon and identification of a gene, TAOS1, that is amplified and overexpressed in oral cancer cells" 2002, *Proc. Natl. Acad. Sci. U.S.A.* 99(17):11369-74.
Izzo et al. "Dysregulated cyclin D1 expression early in head and neck tumorigenesis: in vivo evidence for an association with subsequent gene amplification" 1998, *Oncogene*, 17(18):2313-22.
Jackson et al. "An indolocarbazole inhibitor of human checkpoint kinase (CHEK1) abrogates cell cycle arrest caused by DNA damage" 2000, *Cancer Res.*, 60(3):566-72.
Jemal et al. "Cancer statistics, 2006" 2006, *CA. Cancer J. Clin.*, 56(2):106-30.
Jin et al. "FISH characterization of head and neck carcinomas reveals that amplification of band 11q13 is associated with deletion of distal 11q" 1998, *Genes Chromosomes Cancer*, 22(4):312-20.
Jin et al. "Cyclin D1 amplification in chromosomal band 11q13 is associated with overrepresentation of 3q21-q29 in head and neck carcinomas" 2002, *Int. J. Cancer*, 98(3):475-479.
Jin et al. "Karyotypic heterogeneity and clonal evolution in squamous cell carcinomas of the head and neck" 2002, *Cancer Genet Cytogenet.*, 132:85-96.
Jin et al. "Molecular cytogenetic characterization of the 11q13 amplicon in head and neck squamous cell carcinoma" 2006, *Cytogenet Genome Res.*, 115:99-106.
Kalogeropoulos et al. "Chk-1 is an Essential Gene ad is required for an S-M Checkpoint during early embryogenesis" 2004, *Cell Cycle*, 3(9):1196-200.
Kang et al. "Expression status of ataxia-telangiectasia-mutated gene correlated with prognosis in advanced gastric cancer" 2008, *Mutat. Res.*, 638(1-2):17-25.
Lee et al. "Direct activation of the ATM protein kinase by the MRE11A/Rad50/Nbs1 complex" 2004, *Science*, 304(5667):93-6.
Lee et al., "Sustained activation of Ras/Raf/mitogen-activated protein kinase cascade by the tumor suppressor p53", 2000, *PNAS*, pp. 8203-8305.
Liu et al. "CHEK1 is an essential kinase that is regulated by Atr and required for the G(2)/M DNA damage checkpoint" 2000, *Genes. Dev.*,14(12):1448-59.
Llewellyn et al. "An analysis of risk factors for oral cancer in young people: a case-control study" 2004, *Oral Oncol.*, 40(3):304-13.
Lundberg et al. "Control of the cell cycle and apoptosis" 1999, *Eur. J. Cancer*, 35:531-9.
Martin-Granizo et al. "Squamous cell carcinoma of the oral cavity in patients younger than 40 years" 1997, *Otolaryngol Head Neck Surg.* ,117(3 Pt 1), 268-75.
Matsumoto et al. "Loss of heterozygosity analysis shows monoclonal evolution with frequent genetic progression and divergence in esophageal carcinosarcoma" 2004, *Hum. Pathol.*, 35:322-7.
Meyn "Ataxia-telangiectasia, cancer and the pathobiology of the ATM gene" 1999, *Clin. Genet.*, 55(5):289-304.
Michalides et al. "Overexpression of cyclin D1 correlates with recurrence in a group of forty-seven operable squamous cell carcinomas of the head and neck" 1995, *Cancer Res.*, 55:975-978.
Michalides et al. "Overexpression of cyclin D1 indicates a poor prognosis in squamous cell carcinoma of the head and neck" 1997, *Arch. Otolaryngol. Head Neck Surg.*, 123:497-502.
Mineta et al. "Cyclin D1 overexpression correlates with poor prognosis in patients with tongue squamous cell carcinoma" 2000, *Oral Oncol.*, 36:194-8.
Miyai et al. "Loss of heterozygosity analysis in uterine cervical adenocarcinoma" 2004, *Gynecol. Oncol.*, 94:115-120.
Monni et al. "Gain of 3q and deletion of 11q22 are frequent aberrations in mantle cell lymphoma" 1998, *Genes. Chromosomes Cancer*, 21(4):298-307.
Nagao et al. "Serum antioxidant micronutrients and the risk of oral leukoplakia among Japanese" 2000, *Oral. Oncol.*, 36(5):466-70.
Nakahara et al. "Alterations of Rb, p16(INK4A) and cyclin D1 in the tumorigenesis of oral squamous cell carcinomas" 2000, *Cancer Lett.*, 160(1):3-8.
Namazie et al. "Cyclin D1 Amplification and p16(MTS1/CDK4I) Deletion Correlate With Poor Prognosis in Head and Neck Tumors" Mar. 2002, *Laryngoscope*, 112:472-481.
Neville et al. "Oral cancer and precancerous lesions" 2002, *CA Cancer J. Clin.*, 52(4):195-215.
Ngheim et al. "ATR inhibition selectively sensitizes G1 checkpoint-deficient cells to lethal premature chromatin condensation", 2001, *Proc. Natl. Acad. Sci. U.S.A.*, 98(16):9092-7.
O'Connell et al. "G2 damage checkpoints: what is the turn-on?" 2005, *J. Cell Sci.* , 118(Pt 1):1-6.
O'Driscoll et al. "A splicing mutation affecting expression of ataxia-telangiectasia and Rad3-related protein (ATR) results in Seckel syndrome" 2003, *Nat. Genet.*, 33(4):497-501.
Parikh "The DNA Damage Response Pathway in Oral Squamous Cell Carcinoma" Oct. 9, 2006, University of Pittsburgh, University of Pittsburgh Health Sciences Library System (abstract); Jun. 2, 2007, ProQuest UMI Dissertation Publishing (full thesis).
Parikh et al. "Loss of distal 11q is associated with DNA repair deficiency and reduced sensitivity to ionizing radiation in head and neck squamous cell carcinoma" 2007, *Genes Chromosomes Cancer*, 46(8):761-75.
Paull et al. "A critical role for histone H2AX in recruitment of repair factors to nuclear foci after DNA damage" 2000, *Curr. Biol.*, 10:886-95.
Petti "Pooled estimate of world leukoplakia prevalence: a systematic review" 2003, *Oral Oncol.*, 39(8):770-80.
Poppe et al. "Expression analyses identify MLL as a prominent target of 11q23 amplification and support an etiologic role for MLL gain of function in myeloid malignancies" 2004, *Blood*, 103(1):229-35.
Prime et al. "A review of inherited cancer syndromes and their relevance to oral squamous cell carcinoma" 2001, *Oral Oncol.*, 37(1):1-16.
Reichart "Identification of risk groups for oral precancer and cancer and preventive measures" 2001, *Clin. Oral Investig.*, 5(4):207-13.
Reshmi et al. "Inverted duplication pattern in anaphase bridges confirms the breakage-fusion-bridge (BFB) cycle model for 11q13 amplification" 2007, *Cytogenet. Genome Res.*, 116:46-52.
Rhodus "Oral cancer: leukoplakia and squamous cell carcinoma" 2005, *Dent. Clin. North Am.*, 49(1):143-65, ix.
Rogakou et al. "DNA double-stranded breaks induce histone H2AX phosphorylation on serine 139" 1998,*J. Biol. Chem.* 273:5858-68.
Roh et al. "Visualization of the timing of gene amplification during multistep head and neck tumorigenesis" 2000, *Cancer Res.* 60:6496-502.
Sanchez et al. "Conservation of the CHEK1 checkpoint pathway in mammals: linkage of DNA damage to Cdk regulation through Cdc25" 1997, *Science*, 277(5331):1497-501.

(56) References Cited

OTHER PUBLICATIONS

Sarbia et al. "The predictive value of molecular markers (p53, EGFR, ATM, CHK2) in multimodally treated squamous cell carcinoma of the oesophagus" 2007, *British Journal of Cancer*, 97(10):1404-8.
Sarkaria et al. "Inhibition of ATM and ATR kinase activities by the radiosensitizing agent, caffeine" 1999, *Cancer Res.*, 59(17):4375-82.
Sartor "Role of p16/MTS1, cyclin D1 and RB in primary oral cancer and oral cancer cell lines" 1999, *Br. J. Cancer*, 80(1-2):79-86.
Saunders et al. "Chromosomal instability and cytoskeletal defects in oral cancer cells" 2000, *Proc. Natl. Acad. Sci. USA*, 97:303-8.
Schantz et al. "Head and neck cancer incidence trends in young Americans, 1973-1997, with a special analysis for tongue cancer" 2002, *Arch. Otolaryngol Head Neck Surg.*,128(3):268-74.
Schraml et al. "Tissue microarrays for gene amplification surveys in many different tumor types" 1999, *Clin. Cancer Res.*, 5:1966-75.
Schuuring "The involvement of the chromosome 11q13 region in human malignancies: cyclin D1 and EMS1 are two new candidate oncogenes" 1995, *Gene.*, 159(1):83-96.
Shiloh "ATM and ATR: networking cellular responses to DNA damage" 2001, *Curr. Opin. Genet. Dev.*, 11(1):71-7.
Shiloh "ATM and related protein kinases: safeguarding genome integrity" 2001, *Nat. Rev. Cancer*, 3(3):155-68.
Shiloh "ATM: ready, set, go" 2003, *Cell Cycle*, 2(2):116-7.
Shuster et al. "A consistent pattern of RIN1 rearrangements in oral squamous cell carcinoma cell lines supports a breakage-fusion-bridge cycle model for 11q13 amplification" 2000, *Genes Chromosomes Cancer*, 28(2):153-63.
Silverman "Demographics and occurrence of oral and pharyngeal cancers. The outcomes, the trends, the challenge" 2001, *J. Am. Dent. Assoc.*, 132:7S-11S.
Smith et al. "Duplications of ATR inhibits MyoD, induces aneuploidy and eliminates radiation-induced G1 arrest" 1998, *Nat. Genet.*,19(1):39-46.
Soderlund et al. "Intact Mre11/Rad50/Nbs1 complex predicts good response to radiotherapy in early breast cancer" 2007, *Int. J. Rad. Onco. Bio. Phys.*, 68(1):50-8.
Stell "Time to recurrence of squamous cell carcinoma of the head and neck" 1991, *Head*.
Ward et al. "Histone H2AX is phosphorylated in an ATR-dependent manner in response to replicational stress" 2001, *J. Biol. Chem.*, 276(51):47759-62.
Westphal et al. "Loss of atm radiosensitizes multiple p53 null tissues" 1998, *Cancer Res.*, 58:5637-9.
White et al. "The influence of clinical and demographic risk factors on the establishment of head and neck squamous cell carcinoma cell lines" 2007, *Oral Onco.*, 43(7):701-12.
Ye et al. "Expression patterns of the ATM gene in mammary tissues and their associations with breast cancer survival" 2007, *Cancer*, 109(9):1729-35.
Zatkova et al. "Distinct sequences on 11q13.5 and 11q23-24 are frequently coamplified with MLL in complexly organized 11q amplicons in AML/MDS patients" 2004, *Genes Chromosomes Cancer*, 39(4):263-76.
Zhao et al. "Structural basis for CHEK1 inhibition by UCN-01" 2002, *J. Biol. Chem.*, 277(48):46609-15.
Zhou et al. "Drug discovery targeting CHEK1 and CHK2 kinases" 2003, *Prog. Cell Cycle Res.*, 5:413-21.

Peripheral blood

UPCI:SCC084

UPCI:SCC104

OVCAR-3

Peripheral blood

UPCI:SCC131

FIGURE 11A-B
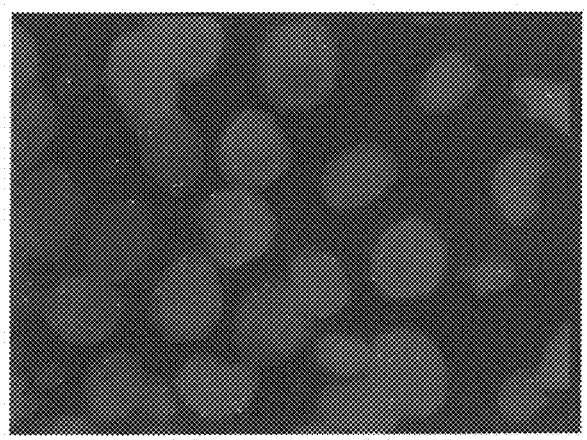
A. Normal
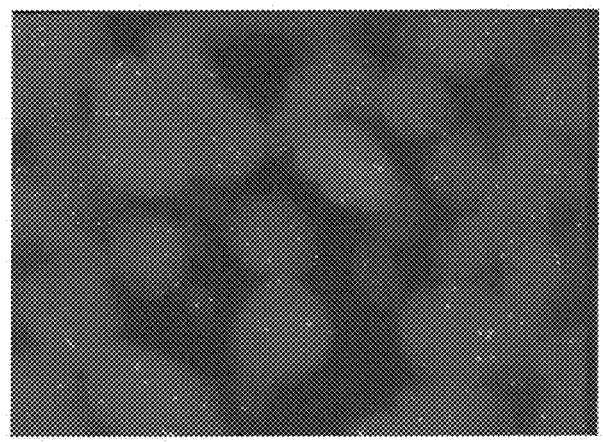
B. Tumor

FIGURE 11C-D
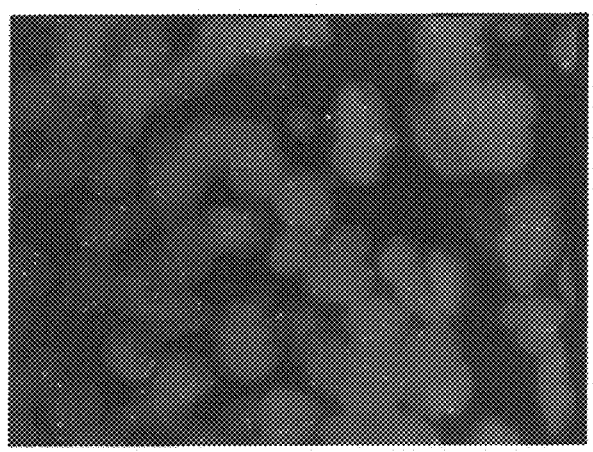
C. Normal
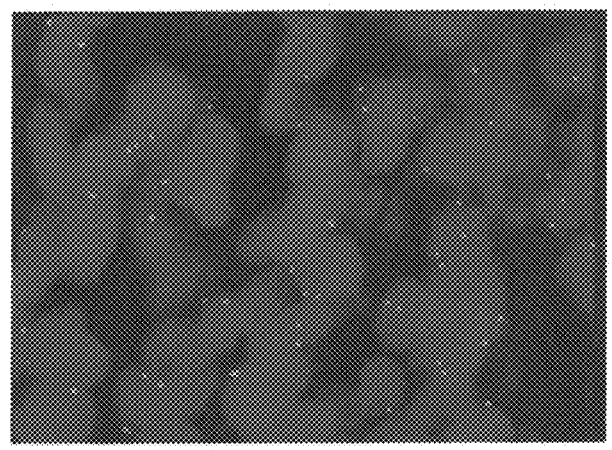
D. Tumor

FIGURE 11E-F
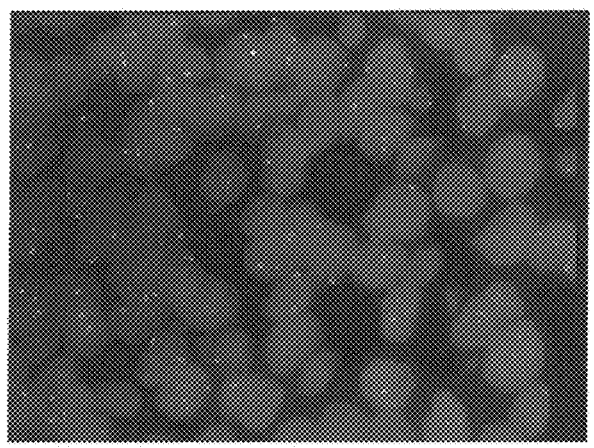
E. Normal
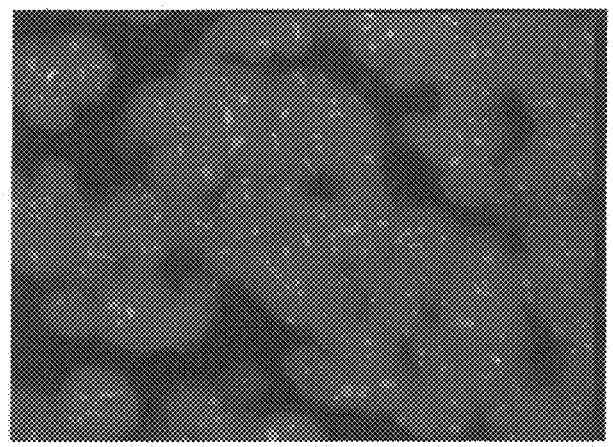
F. Tumor

FIGURE 12A-B
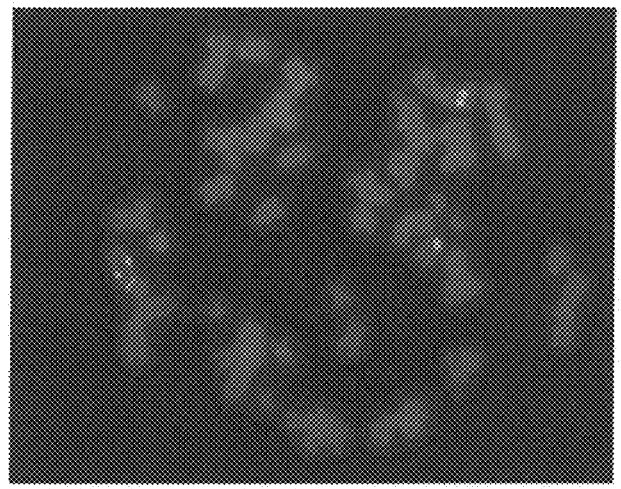
A.
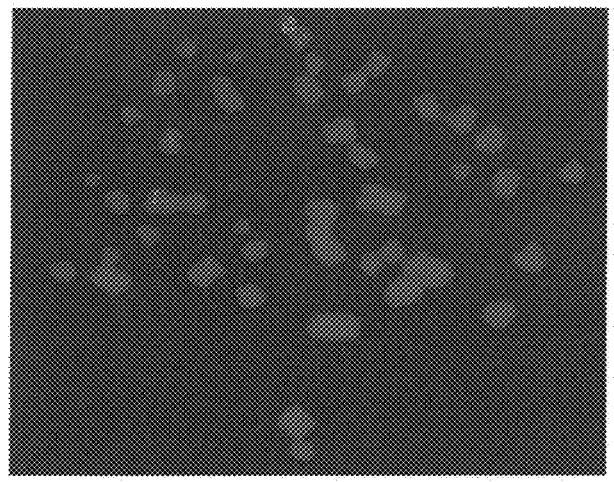
B.

FIGURE 12C-D
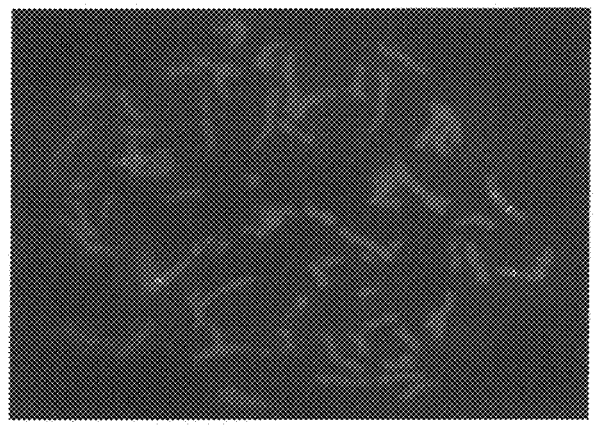
C.
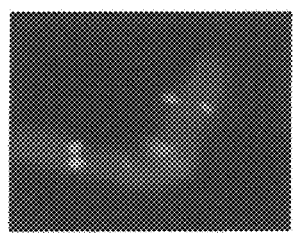
D.

FIGURE 14A-B
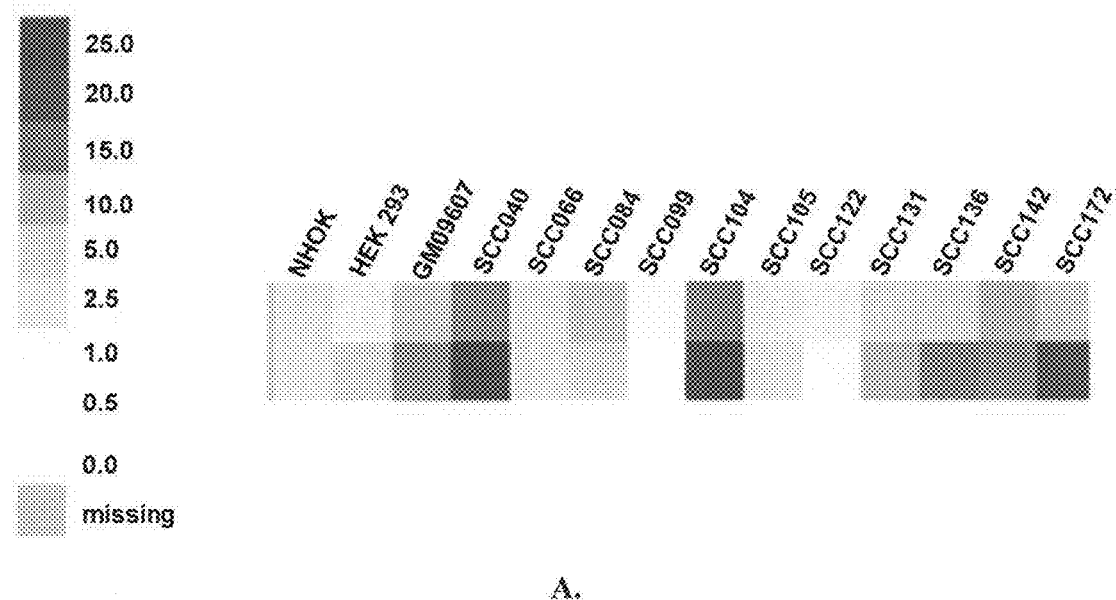
A.
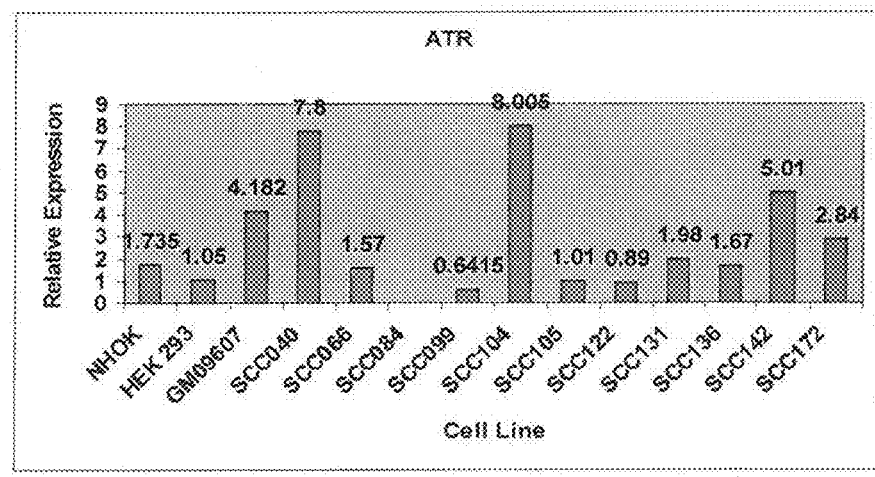
B.

FIGURE 17
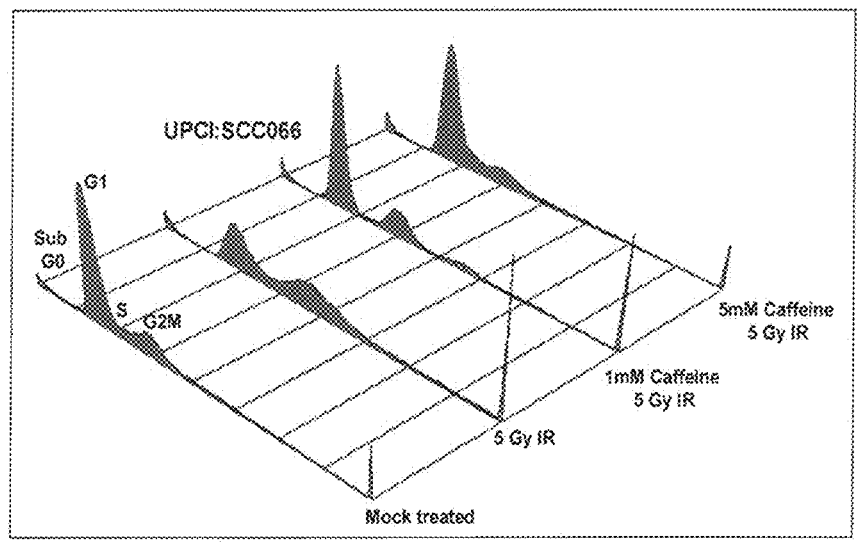
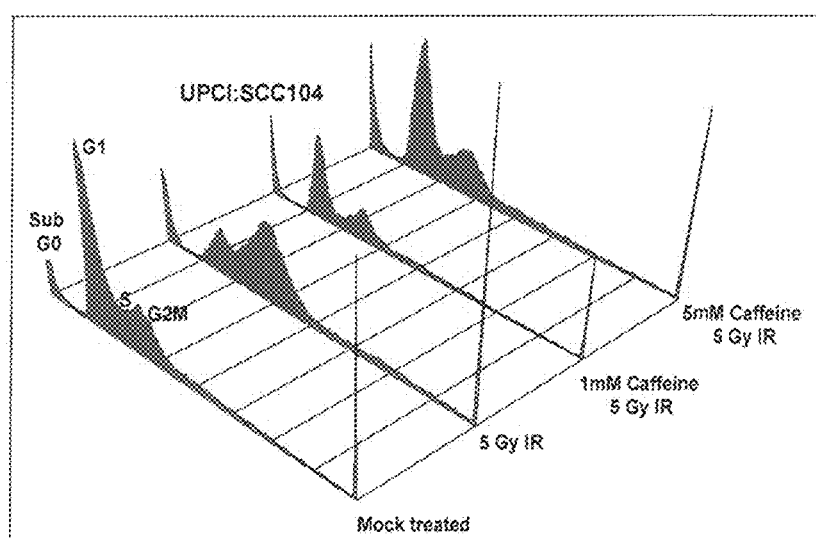

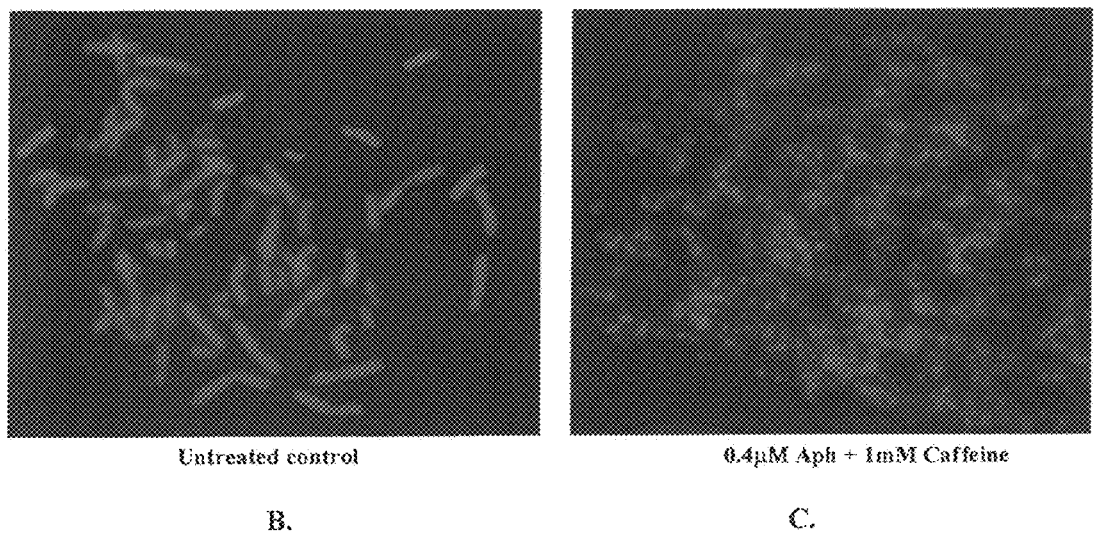
FIGURE 18B-C

FIGURE 21
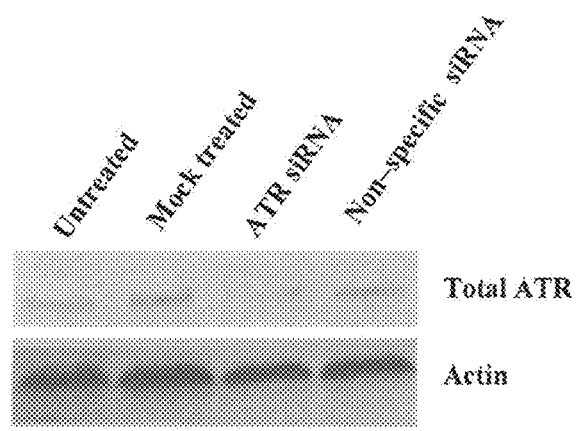
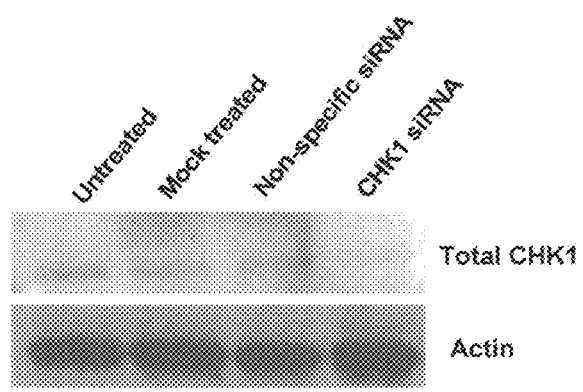

FIGURE 22
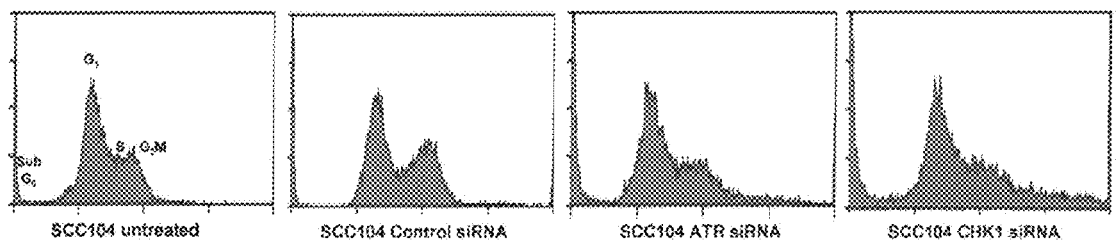
A.
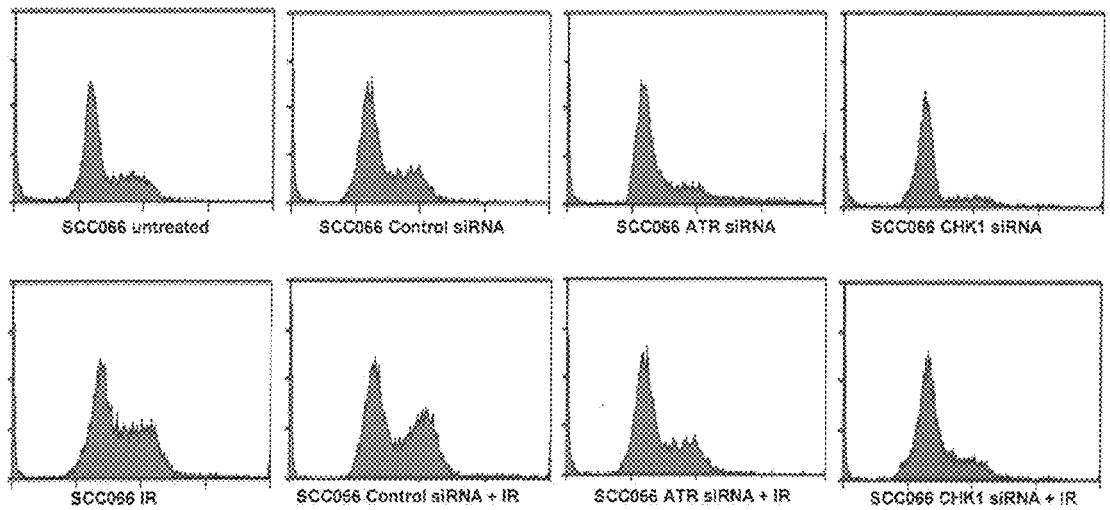
B.

Figure 32:
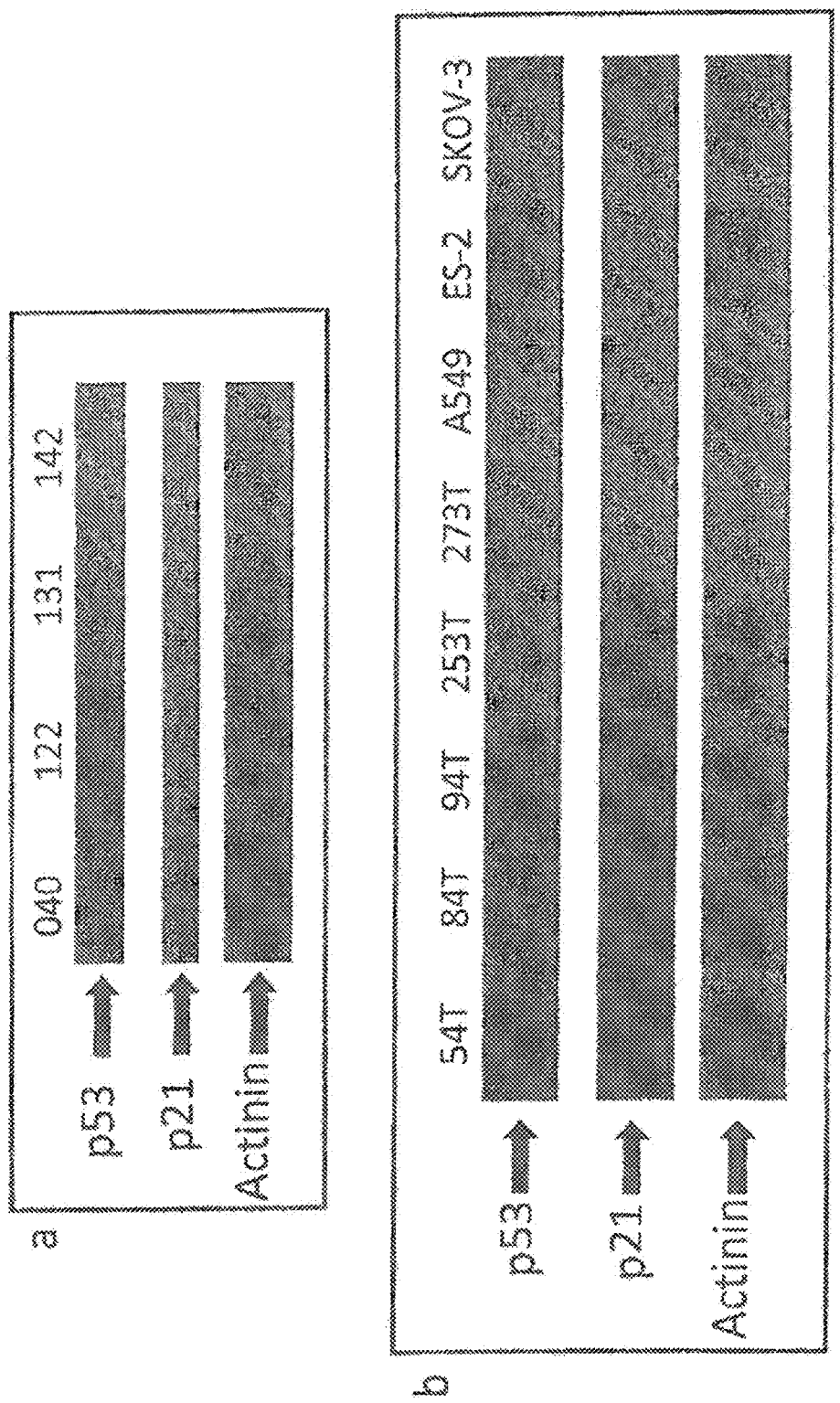

FIGURE 32A-B ined as Sequencelisting.txt, is 6,799 bytes and was created on Apr. 23, 2013. The Sequence Listing does not extend

SEQUENCE LISTING

<160> NUMBER OF SEQ ID NOS: 30

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
ggaattagtg aaataccagt tggaa                                          25

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2
ctctgaaacg acgtacctcc tca                                            23

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
ggcggcagtg ctggagta                                                  18

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
ctctgaaacg acgtacctcc tca                                            23

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 5
cgcccagcag cttgttg                                                   17

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 6
ttttaacttg gttttatgac aattgct                                        27

<210> SEQ ID NO 7
<211> LENGTH: 31
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: unsure
<222> LOCATION: 1
<223> OTHER INFORMATION: 5'-FAM (6-carboxy fluorescein)
<220> FEATURE:
<221> NAME/KEY: unsure
<222> LOCATION: 31
<223> OTHER INFORMATION: TAMRA (6-carboxytetramethylrhodamine)-3'

<400> SEQUENCE: 7
ttcttaaaga acgtcatatt gatgccctcg a                               31

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: unsure
<222> LOCATION: 1
<223> OTHER INFORMATION: 5'-FAM (6-carboxy fluorescein)
<220> FEATURE:
<221> NAME/KEY: unsure
<222> LOCATION: 23
<223> OTHER INFORMATION: TAMRA (6-carboxytetramethylrhodamine)-3'

<400> SEQUENCE: 8
caccgctgag atcctggagc tgg                                        23

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: unsure
<222> LOCATION: 1
<223> OTHER INFORMATION: 5'-FAM (6-carboxy fluorescein)
<220> FEATURE:
<221> NAME/KEY: unsure
<222> LOCATION: 30
<223> OTHER INFORMATION: TAMRA (6-carboxytetramethylrhodamine)-3'

<400> SEQUENCE: 9
ctgctcctaa tccacctcat tttccatcgc                                 30

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tagagatccc gttcgacttg                                            20

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
gctgggtgtt acacaggac                                             19
```

```
<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 12
gtgggcttat tgtggtagta gtc                                          23

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
caagaggagg caggagagtc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tttgtgaaat ctgaagcacc                                              20

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
tccttcatat cctgaatctc tg                                           22

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
cccacataga ttactggcct c                                            21

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
attcctacat tagcagttgg ca                                           22

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 18
ctcctctgta ttcccacaaa ac                                    22

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 19
acctgacatt gtatctaaac ctc                                   23

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
ctacaacctg gatgaaccct a                                     21

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
aaccaacatt ctactttctg tct                                   23

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
atgatgccat atcttgtctt ga                                    22

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 23
aatttaaaga cagatgccaa gc                                    22

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ctagtccctg gaacctggat                                       20

<210> SEQ ID NO 25

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
ggctgatgtg ggctttttca a                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: unsure
<222> LOCATION: 1
<223> OTHER INFORMATION: 5'-FAM (6-carboxy fluorescein)
<220> FEATURE:
<221> NAME/KEY: unsure
<222> LOCATION: 21
<223> OTHER INFORMATION: TAMRA (6-carboxytetramethylrhodamine)-3'

<400> SEQUENCE: 26
tgtgtgtgtg tgtgtgtgtg t                                              21

<210> SEQ ID NO 27
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 27
gaacaacacu gctgguuugg aagucaucug uucauuau                            38

<210> SEQ ID NO 28
<211> LENGTH: 38
<212> TYPE: RNA
<213> ORGANISM: Artificial Sequence
<220> FEATURE:
<223> OTHER INFORMATION: Synthetic oligonucleotide

<400> SEQUENCE: 28
gaaauaaggu agacucaauc aacauaaauc caagaaga                            38

<210> SEQ ID NO 29
<211> LENGTH: 41
<212> TYPE: RNA
<213> ORGANISM: Artificial Sequence
<220> FEATURE:
<223> OTHER INFORMATION: Synthetic oligonucleotide

<400> SEQUENCE: 29
uaaaguacca cacaucuugu uuauuggaua uugccuuucu u                        41

<210> SEQ ID NO 30
<211> LENGTH: 42
<212> TYPE: RNA
<213> ORGANISM: Artificial Sequence
<220> FEATURE:
<223> OTHER INFORMATION: Synthetic oligonucleotide

<400> SEQUENCE: 30
auaugaucag gacauguggu uccauugaua gcccaacuuc uu                       42
```

GENETIC CHANGES IN ATM AND ATR/CHEK1 AS PROGNOSTIC INDICATORS IN CANCER

PRIORITY CLAIM

This application is a continuation of U.S. Ser. No. 13/407, 165, filed Feb. 28, 2012, which is a divisional application of U.S. Ser. No. 12/586,052, now U.S. Pat. No. 8,173,366, filed on Sep. 15, 2009, which is a continuation-in-part of U.S. patent application Ser. No. 12/079,900, filed Mar. 28, 2008, now U.S. Pat. No. 8,263,329, and claims priority to U.S. Provisional Application No. 60/908,891, filed Mar. 29, 2007; U.S. Provisional Application No. 60/912,086, filed Apr. 16, 2007; and U.S. Provisional Application No. 60/912,355, filed Apr. 17, 2007, the contents of each of which are incorporated by reference in their entireties herein.

GRANT INFORMATION

The subject matter of the present invention was developed, at least in part, under National Institutes of Health Grant No. RO1DE14729, P30CA47904, RO1DE016086, R25CA089507 and P50CA097190, so that the United States Government has certain rights herein.

SEQUENCE LISTING

The specification further incorporates by reference the Sequence Listing submitted herein via EFS on Apr. 23, 2013. Pursuant to 37 CFR 1.52(e)(5), the Sequence Listing text file, identified as Sequencelisting.txt, is 6,799 bytes and was created on Apr. 23, 2013. The Sequence Listing does not extend beyond the scope of the specification and thus does not contain new matter.

1. INTRODUCTION

The present invention relates to the discovery that, in human cancer, an 11q deletion of ATM together with an increase in ATR and CHEK1 expression correlates with resistance to ionizing radiation which could be overcome by inhibition of the ATR/CHEK1 pathway. It provides for methods of identifying patients unlikely to exhibit an adequate response to radiation therapy and/or chemotherapy who may benefit from ATR/CHEK1 pathway inhibition, as well as methods of treating said patients.

2. BACKGROUND OF THE INVENTION

2.1 Oral Squamous Cell Carcinoma

Worldwide, head and neck squamous cell carcinoma (HNSCC) is the sixth most common cancer; it is the third most common cancer in developing nations. There were 404, 575 new cases in 2002, constituting 3.7% of the total estimated cancer cases worldwide (PARKIN et al., 2002). According to a recent study by the American Cancer Society, in 2006, there were expected to be approximately 30,990 new cases of HNSCC and 7,430 deaths related to HNSCC (JEMAL et al. 2006).

HNSCC encompass tumors of the tongue, oral cavity, pharynx and larynx. Of these, tumors of the oral cavity and tongue, that is oral squamous cell carcinomas (OSCC) account for more than 90% of all HNSCC (SCHANTZ and YU 2002). Although the elderly population accounts for most of the cases of OSCC, recently there has been a significant increase in OSCC incidence in the younger age group (MARTIN-GRANIZO et al. 1997, SILVERMAN 2001).

Leukoplakia, erythroplakia, nicotine stomatitis, tobacco pouch keratosis and oral submucosal fibrosis are common premalignant lesions which may progress to OSCC (NEVILLE and DAY 2002). Leukoplakia, which is a white discoloration in the lining of the oral cavity, is very common in the elderly population. Nearly 10-15% of leukoplakia lesions progress to OSCC over a period of time (PETTI 2003).

The common risk factors for oral squamous cell carcinoma are tobacco chewing, smoking, alcohol consumption and human papillomavirus (HPV) infection (RHODUS 2005). Vitamins A and C, on account of their antioxidant activity, are shown to be protective against the development of oral leukoplakia and squamous cell carcinoma (NAGAO et al. 2000). The combined effects of tobacco use, alcohol consumption and poor dietary habits account for over 90% of head and neck cancer cases (REICHART 2001).

In addition to tobacco and alcohol consumption, dietary habits, genetic predisposition, and unknown risk factors may play a role in the increased incidence of OSCC observed recently (LLEWELLYN et al. 2004). In spite of better methods of diagnosis and new procedures for treatment, there has not been a significant difference in the five year survival rate for HNSCC over the past 30 years; it was 59% during 1995-2000 and 54% during 1974-1976 (JEMAL et al. 2006). Thus, there is a need to develop new biomarkers for effective screening, and therapeutic strategies for treatment of leukoplakia and OSCC.

2.2 Chromosomal Instability

One hallmark of solid tumors is chromosomal instability, which helps drive cancer growth and progression. As the tumor progresses, its genotype evolves into one that is optimized for proliferation, spread and invasion into surrounding tissues. Thus, over a period of time, genetic alterations that confer a growth advantage are selected (ALBERTSON et al. 2003). Chromosomal instability is a state of continuous, dynamic, propagated changes in chromosome structure and/or number, which is usually seen in solid tumors.

OSCC exhibits a high level of chromosomal instability with near-triploid or tetraploid karyotypes composed of multiple clonal numerical and structural chromosomal abnormalities (VAN DYKE et al. 1994, GOLLIN 2001, JIN et al. 2002). Chromosomal segregational defects, involving multipolar spindles are a common cause of numerical chromosomal instability in OSCC (SAUNDERS et al. 2000, GISSELSSON et al. 2002). The anaphase bridges and micronuclei observed in OSCC may be caused by DNA defects in the damage response and/or dysfunctional telomeres (GOLLIN 2001, GISSELSSON 2003). Anaphase bridges are intermediates in the process of gene amplification (SHUSTER et al. 2000, SAUNDERS et al. 2000).

Changes in DNA ploidy and chromosomal abnormalities can be detected in tumor—adjacent normal tissue and dysplastic tissue and also in premalignant lesions of the oral cavity (SUDBO et al. 2002). Thus, chromosomal instability is a relatively early event in head and neck tumor development. A high degree of chromosomal aneuploidy and changes in DNA ploidy in OSCC are correlated with lymph node metastasis, poor response to treatment and poor prognosis (HOLM 1982, STELL 1991). Even though OSCC exhibits a high degree of cytogenetic heterogeneity, certain chromosomal changes like 11q13 amplification, gains involving 3q21-29, 5p, 8q, 18q and 22q and losses involving 3p, 8p, 9p, 11q, 13q and 21q occur regularly and may play a role in OSCC development and progression (BOCKMUHL and PETERSEN 2002).

Amplification of chromosomal band 11q13, one form of chromosomal instability, is present in nearly 45% of OSCC (GOLLIN 2001). 11q13 amplification is an independent prognostic factor which correlates with higher stage disease, lymph node involvement, shorter time to recurrence, and reduced overall survival (AKERVALL et al. 1997, FRAC-CHIOLLA et al. 1997, MICHALIDES et al. 1997). Gene amplification, the generation of extra copies of a gene or genes, is a common genetic defect in human tumors, including OSCC. Amplification and subsequent overexpression of critical genes has been shown to lead to dysregulation of the cell cycle, resulting in cellular proliferation and tumor formation and/or progression (LUNDBERG et al. 1999).

Chromosomal band 11q13, which harbors the locus for a key cell cycle regulatory gene, cyclin D1 gene (CCND1) and other neighboring genes, is the most frequently amplified genetic segment in OSCC (AKERVALL et al. 1997, GOLLIN 2001, HUANG et al. 2002). 11q13 amplification is also present in a smaller percentage of other carcinomas (SCHRAML et al. 1999). Hittelman and colleagues report that 11q13 amplification occurs early in the pathogenesis of OSCC, in premalignant lesions prior to development of invasive carcinoma (IZZO et al. 1998). 11q13 amplification with cyclin D1 overexpression is a critical event in the pathogenesis of OSCC and is associated with a poor prognosis (AKERVALL et al. 1997).

11q13 amplification in OSCC occurs by the breakage-fusion-bridge (BFB) mechanism, first described in maize by geneticist Barbara McClintock in 1938. The first step in the BFB model of 11q13 amplification is loss of a distal portion of chromosome 11, resulting in an unprotected chromosome end which fuses with its sister chromatid to form a dicentric chromosome. During chromosomal segregation, the two centromeres are pulled to different poles, leading to additional breaks and thus the cycle continues till a derivative chromosome 11 with 11q13 amplification is formed (SHUSTER et al. 2000). During the initial step of 11q13 amplification, a segment of distal 11q harboring important genes involved in DNA damage recognition and repair like MRE11A (11q21), ATM (11q22.3), H2AFX (11q23.2) and CHEK1 (11q24) are lost.

2.3 ATR and CHEK1

CHEK1 and CHEK2 (also referred to as CHK1 and CHK2) are highly conserved effector kinases which transmit signals from ATM and ATR to downstream proteins. This in turn leads to cell cycle checkpoint activation, and DNA repair (BARTEK and LUCAS 2003). CHEK1 mainly acts during the G2 and S phases of the cell cycle to initiate cell cycle checkpoints in response to DNA damage (LIU et al. 2000). The early lethality of CHEK1-deficient embryonic cells (TAKAI et al. 2000) and early embryonic lethality of CHEK1-deficient mice (LIU et al. 2000) suggests that CHEK1 plays a very important role during early development and viability in mammals (KALOGEROPOULOS et al. 2004).

CHEK1 induced G2M arrest is mediated through phosphorylation and inactivation of the Cdc25 phosphatases (SANCHEZ et al. 1997). In addition to CHEK1 and CHEK2, a number of other proteins like p53, MDM2, c-ABL, SMC1, BRCA1, BRCA2, and the Fanconi proteins are phosphorylated and activated by ATM and ATR (SHILOH et al. 2001a, SHILOH et al. 2001b). Thus, perturbation of either ATM or ATR may have a ripple effect and affect the regulation and control of numerous proteins and pathways involved in the DNA damage response.

The aim of the G2 (G2M) checkpoint is to prevent cells with improper DNA replication or DNA damage from entering mitosis. The critical regulator of the G2 checkpoint is the pro-mitotic cyclin B/CDK 1 kinase complex which in turn is regulated by the ATR, CHEK1 and CDC25 phosphatase family of proteins (O'CONNELL et al. 2005). The G2 checkpoint partly relies on p53-dependent mechanisms. However, it has been shown that p53-independent mechanisms are sufficient to sustain G2 arrest. Entry of cells with DNA damage into mitosis results in activation of an M phase-specific, p53-independent pathway that results in mitotic catastrophe and apoptosis (O'CONNELL et al. 2005). It has been shown that knockout of either CHEK1 or ATR results in mitotic catastrophe during embryogenesis or loss of replication checkpoint control in cycling *Xenopus* extracts (HEKMAT-NEJAD et al. 2000).

Since the G1 phase checkpoint is lost in a large number of tumors, there is growing interest in S and G2 phase checkpoint abrogating agents which can sensitize these tumors to chemotherapy and radiotherapy (ZHOU et al. 2003).

3. SUMMARY OF THE INVENTION

The present invention relates to the discovery that, in human cancer, an 11q deletion of ATM together with an increase in ATR and CHEK1 expression correlated with resistance to ionizing radiation which could be overcome by inhibition of the ATR/CHEK1 pathway. It is based, at least in part, on the discovery that both ATR and CHEK1 are overexpressed in a subset of oral squamous cell carcinomas ("OSCCs") with loss of the G1 cell cycle checkpoint, and that non-specific inhibition of ATR or CHEK1 with caffeine or specific inhibition with the respective siRNAs resulted in an increased susceptibility of the OSCCs to DNA damaging agents. It is further based, in part, on the results of FISH evaluation of a variety of cancer cell lines which demonstrated the presence of 11q loss as well as amplification of cyclin D1 (CCND1), a gene in the chromosomal band 11q13 locus, in a substantial percentage of the cancers tested. It is still further based on the discovery that decreased or absent p53 expression and/or activity is associated with resistance to ionizing radiation and susceptibility to inhibition of the CHEK1 pathway, so that p53 is another biomarker that may be used according to the invention.

In one set of non-limiting embodiments, the present invention provides for methods of identifying patients unlikely to exhibit an adequate response to radiation therapy who may benefit from ATR/CHEK1 pathway inhibition, as well as methods of treating said patients. For example, such a patient may be identified by detecting, in a cancer cell of said patient, a loss of 11q together with an increase in the expression of ATM and/or CHEK1, optionally an increase in CCND1 (which may occur with loss of 11q), and optionally a decrease or absence of p53 expression and/or activity.

In further non-limiting embodiments, the present invention provides for kits which may be used to identify patients who may be resistant to radiation therapy and/or may benefit from ATR/CHEK1 pathway inhibition.

4. BRIEF DESCRIPTION OF THE FIGURES
COLOR FIGURES

The patent or application file contains at least one drawing executed in color. Copies of this patent or patent application publication with color drawing(s) will be provided by the Office upon request and payment of the necessary fee.

FIG. 1. QuMA studies to map segmental loss of microsatellite loci on distal 11q. QuMA was performed for each of the OSCC cell lines in the three groups. The cell lines were grouped as (A) "no 11q13 amplification, no distal loss", (B) "11q13 amplification with distal 11q loss" and (C) "distal 11q loss but no 11q13 amplification".

Figure 2:
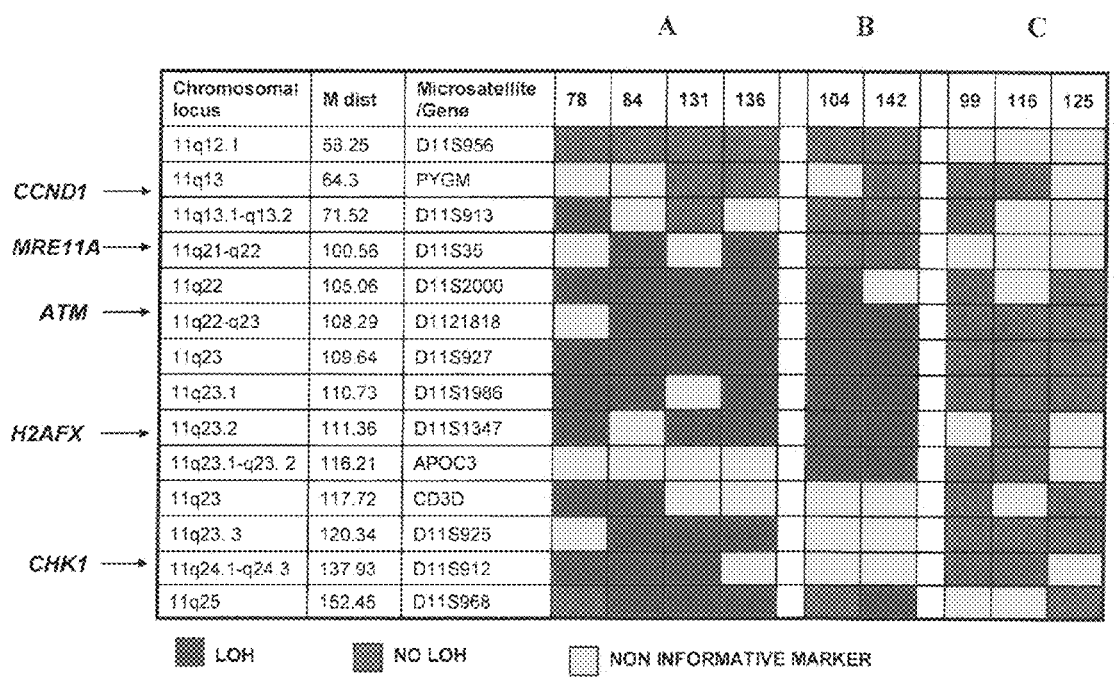

FIG. 2. Loss of heterozygosity ("LOH") studies performed on OSCC for multiple loci on distal 11q. LOH studies for multiple markers on chromosome 11q demonstrate loss of distal loci or genes in cell lines from each of the three groups: A "11q13 amplification with distal 11q loss", B "distal 11q loss but no 11q13 amplification" and C "no 11q13 amplification, no distal loss".

Figure 3:
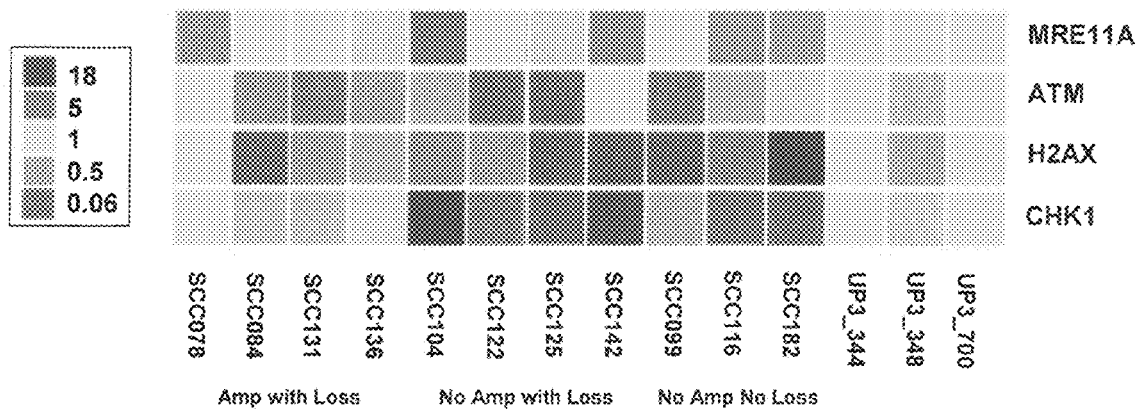

FIG. 3. RNA expression changes for MRE11A, ATM, H2AX and CHEK1 in OSCC. Qualitative Real-Time PCR ("qRT-PCR") was performed for the four genes MRE11A, ATM, H2AX and CHEK1 on distal 11q. Overall genetic loss of ATM and H2AX correlated well with a reduced expression. UPCI:SCC084, 136, 142 and 125 show increased CHEK1 expression in spite of loss at the gene level. UP3_344, 348 and 700 are normal human oral keratinocytes (control cell lines). R=red; O/R=orange red (predominantly red); R/O=red orange; O=orange; Y/O=yellow orange; O/Y=orange yellow; Y=yellow; G/Y=green yellow; Y/G=yellow green; G=green; G/DG=green dark green; DG=dark green.

Figure 4:
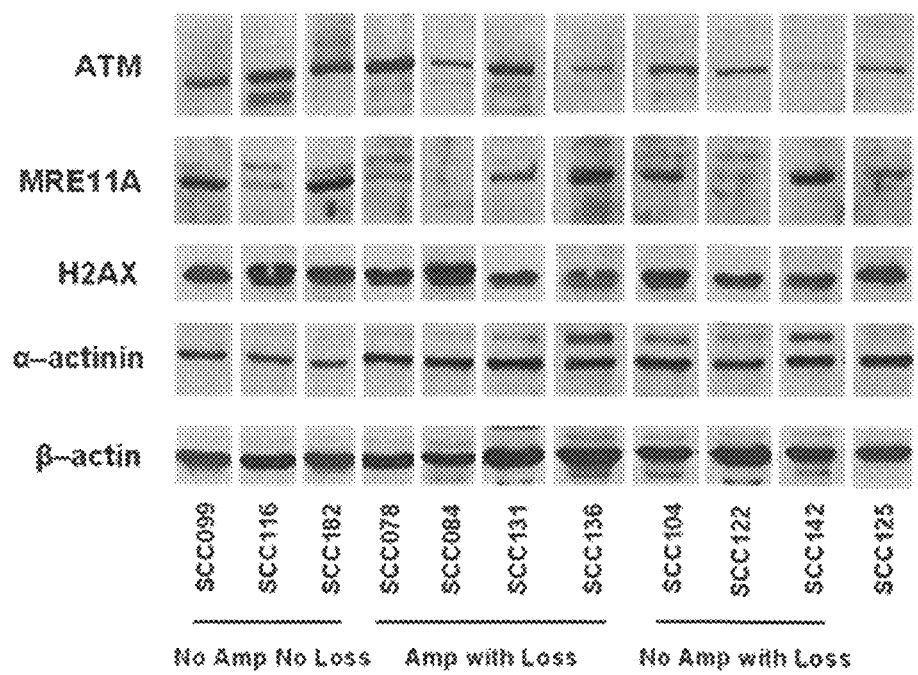

FIG. 4. Protein expression changes for MRE11A, ATM and H2AX in OSCC. Immunoblotting was performed to detect changes in protein expression for MRE11A, ATM and H2AX. We observed reduction in MRE11A, ATM and H2AX protein in most cell lines with loss irrespective of their amplification status.

Figure 5:
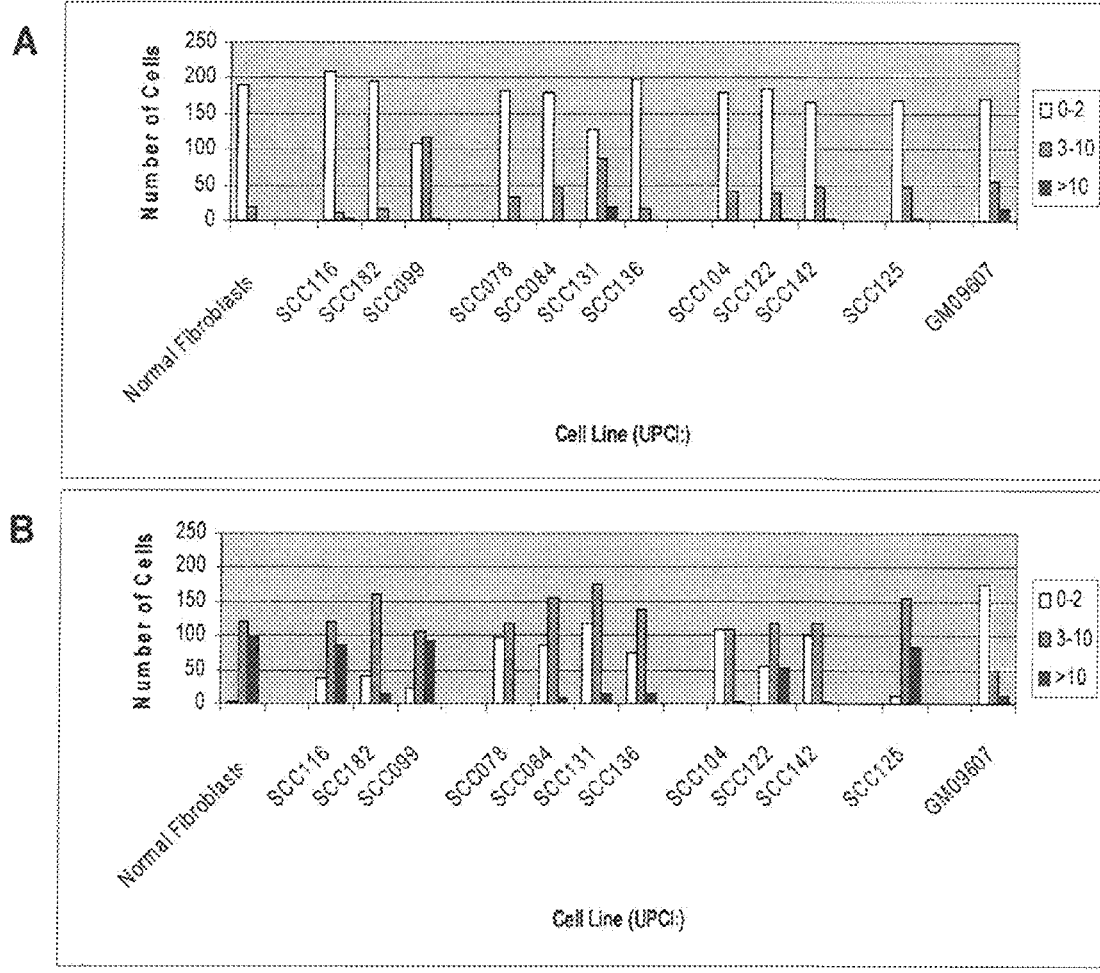

FIG. 5A-B. γ-H2AX focus formation at the end of 1 h following 2.5 Gy IR treatment. The distribution of γ-H2AX focus formation was evaluated in (A) untreated OSCC cell lines, NHOK and an AT cell line (GM09607) and (B) OSCC cell lines, NHOK and an AT cell line treated with 2.5 Gy IR at the end of 1 h.

Figure 6:
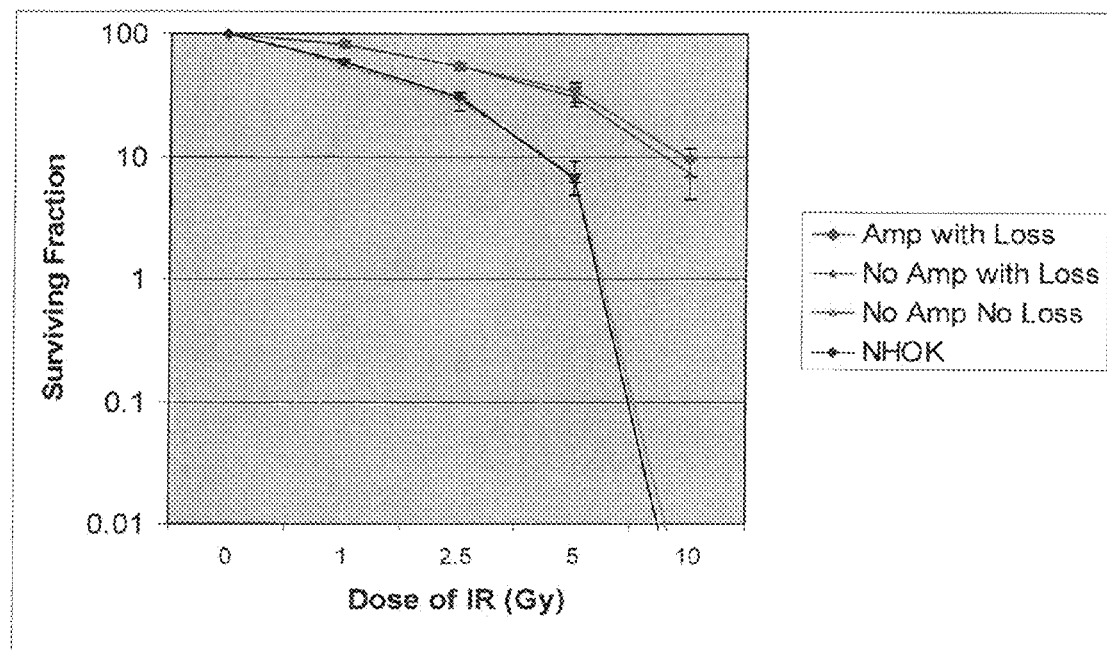

FIG. 6. Clonogenic cell survival of OSCC to IR compared with control NHOK. Grouped analysis for clonogenic cell survival demonstrates that the cell lines with no amplification but with loss (red), and cell lines with amplification and loss (blue) show a similar survival, while cell lines with no amplification and no loss (orange) show survival comparable to the control NHOK. At a very high IR dose of 10 Gy, cell lines with 11q loss irrespective of their amplification status have an average of 9% cells surviving.

FIG. 7A-D. Comprehensive summary of DNA damage-related results in representative cell lines, showing results from the FISH, focus formation and chromosome aberration assays. UPCI:SCC116 has no amplification of 11q13 or loss of distal 11q. UPCI:SCC084 has 11q13 amplification and loss of distal 11q. UPCI:SCC104 has loss of distal 11q, but no 11q13 amplification. In (A), FISH images showing copy number in each of the cell lines. In each FISH image, CEP 11 is labeled red (indicated by an arrow pointing at the image) and H2AFX is labeled green (indicated by a circle around the image). UPCI:SCC116, which is near-triploid, shows the expected complement of three red and three green signals. UPCI:SCC084, which is near-diploid, has two CEP 11 signals and only one green signal. UPCI:SCC104, which is near-triploid, has four copies of the chromosome 11 centromere and only two copies of H2AFX. In (B), γ-H2AX focus formation in control and treated (2.5 Gy IR with 1 h repair) cells. After treatment, UPCI:SCC116 shows a large number of foci, indicating recognition of double-strand breaks. UPCI:SCC084 and UPCI:SCC104 have higher baseline levels of focus formation, and markedly fewer foci in response to equivalent doses of radiation. All focus formation images are composite images of five 0.2 μm z-stacks. Examples of common breakage events are shown for each cell line in (C), as indicated with a green arrow. The metaphase spread for UPCI:SCC116 does not show any breaks two days post-IR, but UPCI:SCC084 and UPCI:SCC104 show numerous breakage events at the same time point. A summary of the total weighted aberrations per cell for representative cell lines are shown in (D). A chromosomal breakage assay was carried out on three cell lines, one with "No Amplification, No Loss" (UPCI:SCC116), another with "Loss, No Amplification" (UPCI:SCC104) and a third with "Amplification with Loss" (UPCI:SCC084). Control, white; IR, gray. Chromosome aberrations are weighted as previously described, and then normalized to a diploid cell. In brief, two-break events including chromosome breaks, radials, giants, rings and dicentrics were assigned twice the weight of other aberrations. The total weighted aberrations were summed, and determined per chromosome and per cell for each treatment. Error bars are provided as the standard error of the sample mean for both control and treated samples.

Figure 8:
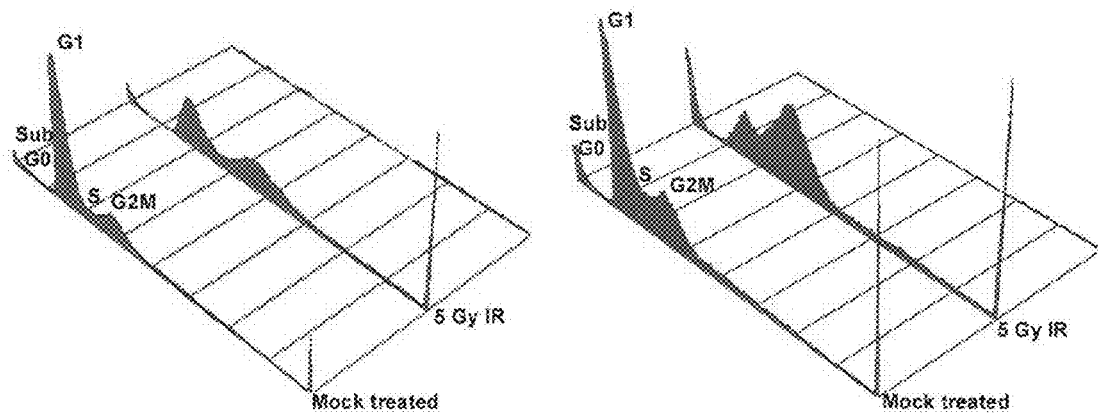

FIG. 8. Comparison of cell cycle profiles of UPCI:SCC066 and 104 in response to IR. UPCI:SCC066 and 104 were either mock treated or treated with 5 Gy IR and allowed to recover for 24 h. At the end of 24 h, flow cytometric analysis show complete loss of the G1 cell cycle checkpoint in UPCI:SCC104 with most cells accumulating in the S and G2M phases, UPCI:SCC066 cells accumulate at both G1 and G2M cell cycle checkpoints.

Figure 9:
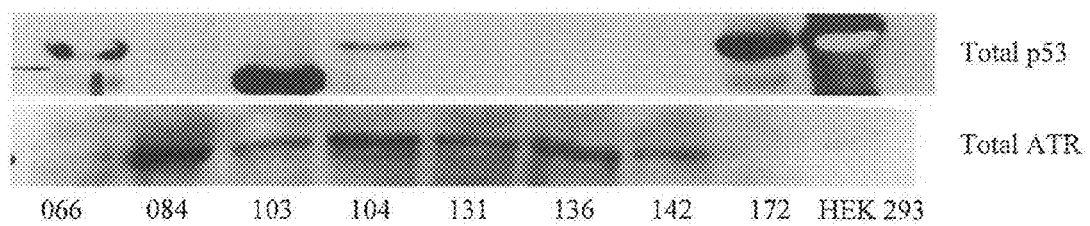
Figure 10A:
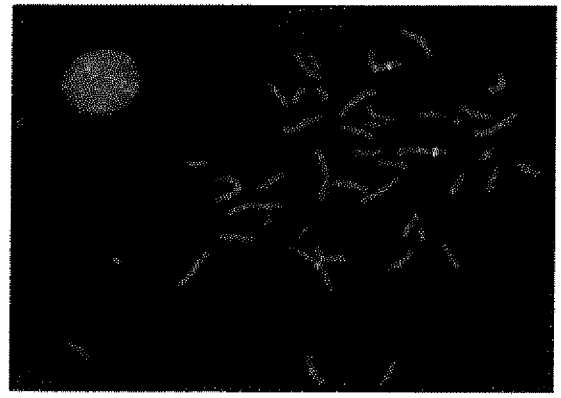
Figure 10B:
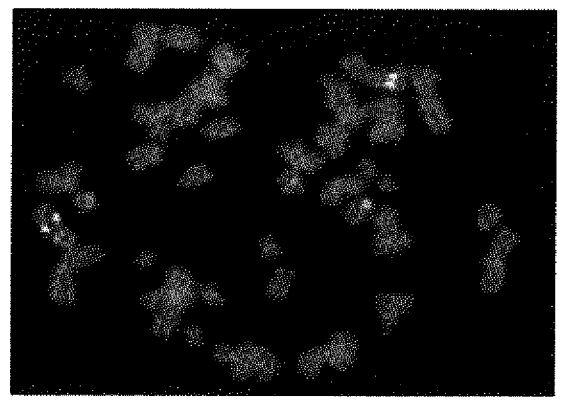
Figure 10C:
Figure 10D:
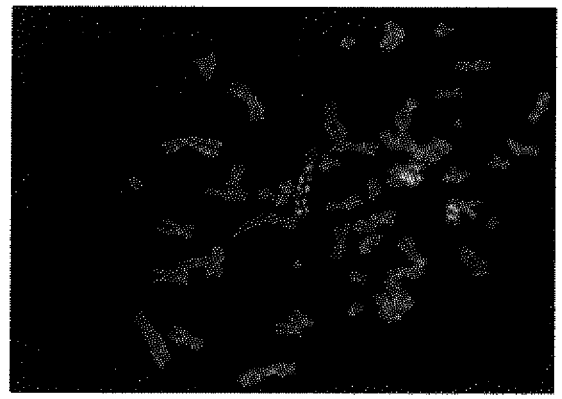
Figure 10E:
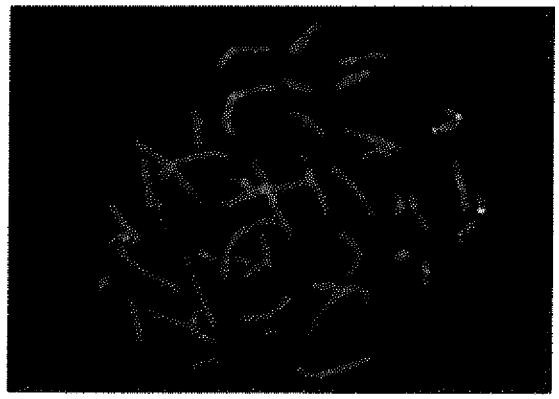
Figure 10F:
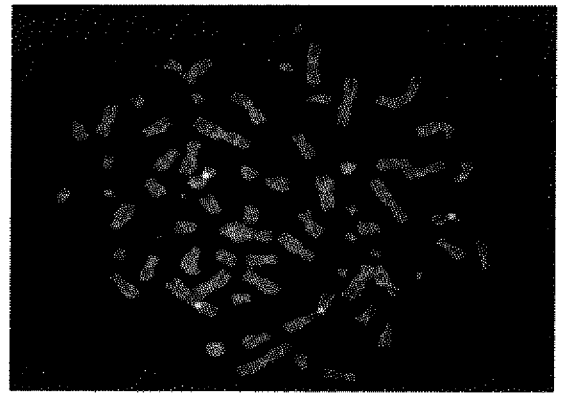

FIG. 9. p53 and ATR expression in a subset of OSCC. Loss of p53 expression correlates with an increased expression of ATR protein in UPCI:SCC084, 104, 131, 131, 136 and 142. UPCI:SCC103, which has a truncated p53 protein also has ATR overexpression. Expression in UPCI:SCC066 and 172 is comparable to that observed in HEK 293 cells.

FIG. 10A-F. Structural and numerical changes in ATR and CHEK1 genes in tumor cell lines. (A) Demonstrates two copies of ATR gene (green) and two CEP 3 (red) signals in normal metaphase. (B) We observed a translocation of the ATR gene (green) in UPCI:SCC084. In UPCI:SCC104 (C) ATR gene (green) is gained with isochromosome 3q formation. In an ovarian tumor cell line, OVCAR-3 (D), we observe amplification of the ATR gene (green) compared to CEP 3 (red). (E) Represents normal metaphase with two CHEK1 (red) and two CEP 11 (green) signals (F) UPCI:SCC131 with loss of the CHEK1 gene (red) compared to CEP 11 (green).

FIG. 11A-F. Results for ATR, CHEK1 and CCND1 FISH in primary head and neck tumors and adjacent normal tissue. (A-B) demonstrate gain in ATR gene (green) copy number compared with CEP 3 (red) in normal (A) and tumor (B); (C-D) show loss of CHEK1 gene (red) compared to CEP 11 (green) in normal (C) and tumor (D); (E-F) demonstrate amplification of CCND1 gene (red) compared to CEP 11 (green) in tumor tissue but not in the adjacent normal tissue.

FIG. 12A-D. ATR translocation in SCC084 and isochromosome 3 formation in SCC104. (A) shows translocation of one copy of ATR gene (green) from chromosome 3 (red), further analysis of UPCI:SCC084; (B) reveals that ATR (green) is translocated to the derivative chromosome 11 (red) with amplified CCND1 (aqua); (C) demonstrates UPCI:SCC104 with an isodicentric chromosome 3 and ATR gain (green); (D) is a magnification of the isodicentric chromosome shown in (C).

Figure 13A:
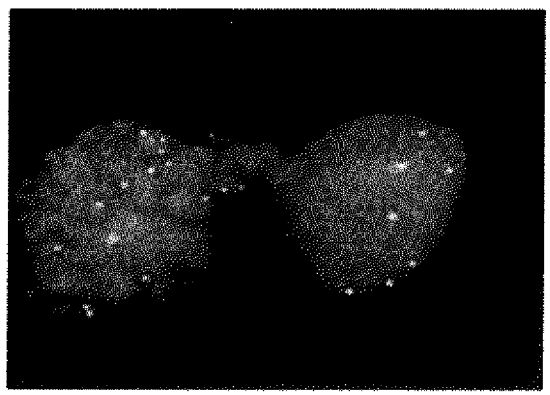
Figure 13B:
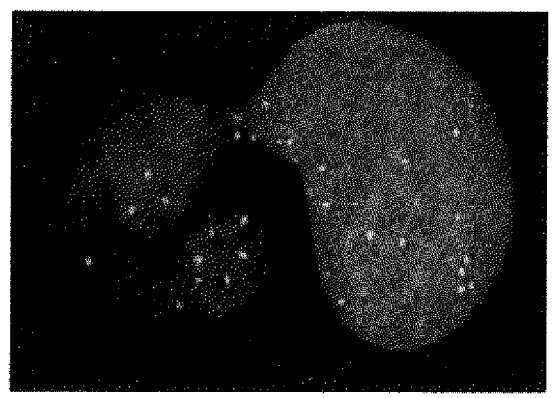

FIG. 13A-B. Presence of ATR (green), CEP11 (aqua) and CEP3 (red) in anaphase bridge. UPCI:SCC104 (Panel A)

demonstrates two ATR copies and two CEP 3 copies in the anaphase bridge. In GM09607 (Panel B), two ATR copies and two CEP 3 copies are present in the anaphase bridge (white arrow) while one CEP 11 copy is present in another anaphase bridge (red color).

Figure 14C:
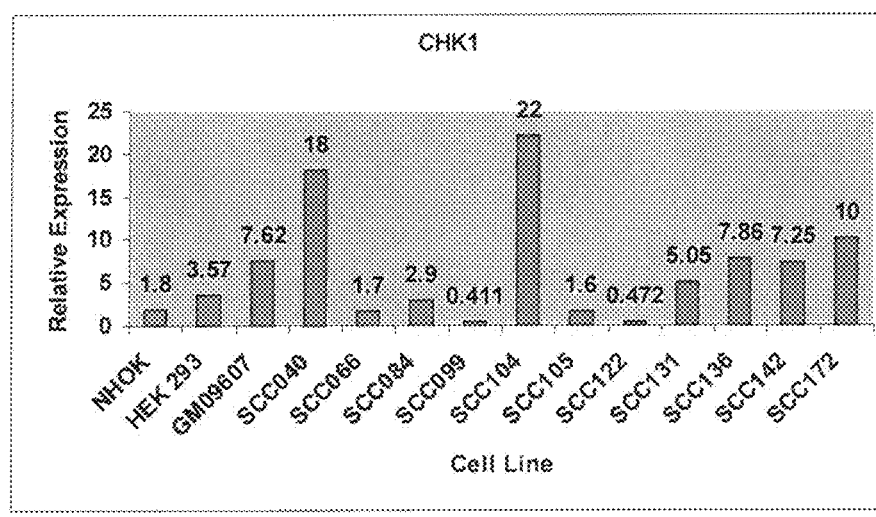

FIG. 14A-C. qRT-PCR analysis for ATR and CHEK1 RNA expression in subset of OSCC. (A) demonstrates heat map of ATR (top row) and CHEK1 (bottom row) expression, (B) Bar graph depicting relative ATR expression (C) Bar graph depicting relative CHEK1 expression.

Figure 15:
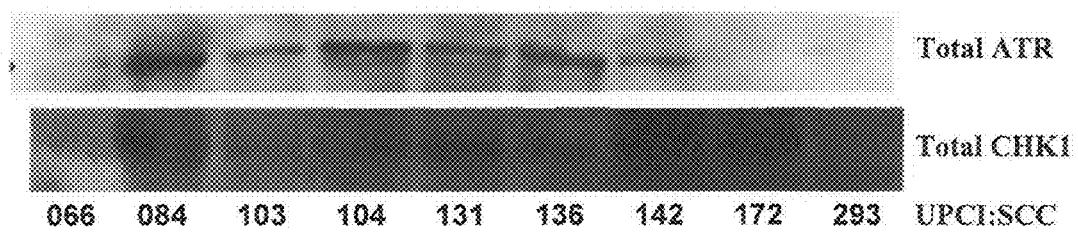

FIG. 15. ATR and CHEK1 protein expression in OSCC detected by immunoblotting. Immunoblotting for ATR and CHEK1 demonstrates high ATR and CHEK1 expression in UPCI:SCC084, 104, 131, 136, 142 and 172.

Figure 16A:
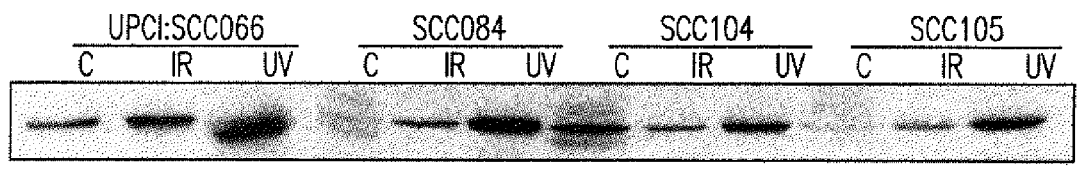
Figure 16B:
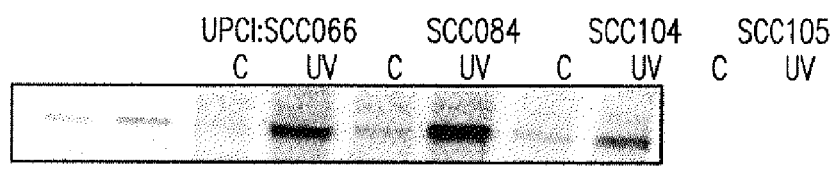
Figure 16C:
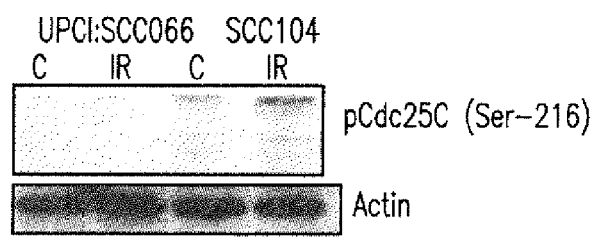

FIG. 16A-C. Activation of downstream effectors of ATR in response to IR and UV. (A) Phosphorylation of CHEK1 on serine-345 was studied in response to 5 Gy IR and 20 J/m2 dose of UV radiation in UPCI:SCC066, 084, 104 and 105. (B) Phosphorylation of SMC1 on serine-957 was studied in response to 20 J/m2 dose of UV radiation in UPCI:SCC066, 084, 104 and 105. (C) Phosphorylation of Cdc25C serine-216 was studied in response to 5 Gy IR UPCI:SCC066 and 104.

FIG. 17. Cell cycle profiles of UPCI:SCC066 and 104 in response to IR and caffeine treatment. UPCI:SCC066 (Panel A) and UPCI:SCC104 (Panel B) were either treated with 5 Gy IR or pretreated with 1 mM caffeine 1 h prior to treatment with 5 Gy IR, or pretreated with 5 mM caffeine 1 h prior to 5 Gy IR and the cell cycle profiles were compared with untreated samples from the same cell line. Compared to SCC066, SCC104 exhibits a loss of G1 checkpoint and predominant G2M accumulation following treatment with IR. SCC104 exhibits a caffeine-dose dependent reduction in G2M accumulation and increase in sub G0 peak (dead cells) suggesting that caffeine sensitizes SCC104 to IR mediated cell death.

Figure 18A:
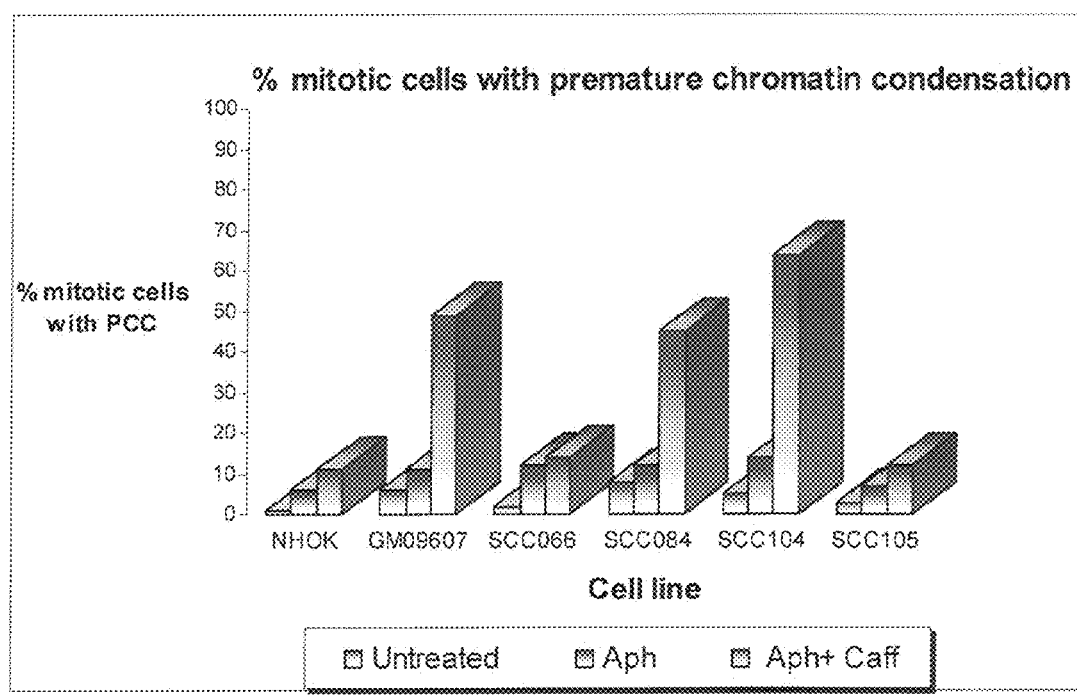

FIG. 18A-C. The frequency of PCC formation (cell death) in untreated cells, in response to aphidicolin with or without 1 mM caffeine pretreatment. (A) Demonstrates the frequency of mitotic cells undergoing PCC/MC in OSCC, NHOK and GM09607. (B,C) Depicts PCC/MC formation in UPCI: SCC104 under the specified conditions.

Figure 19:
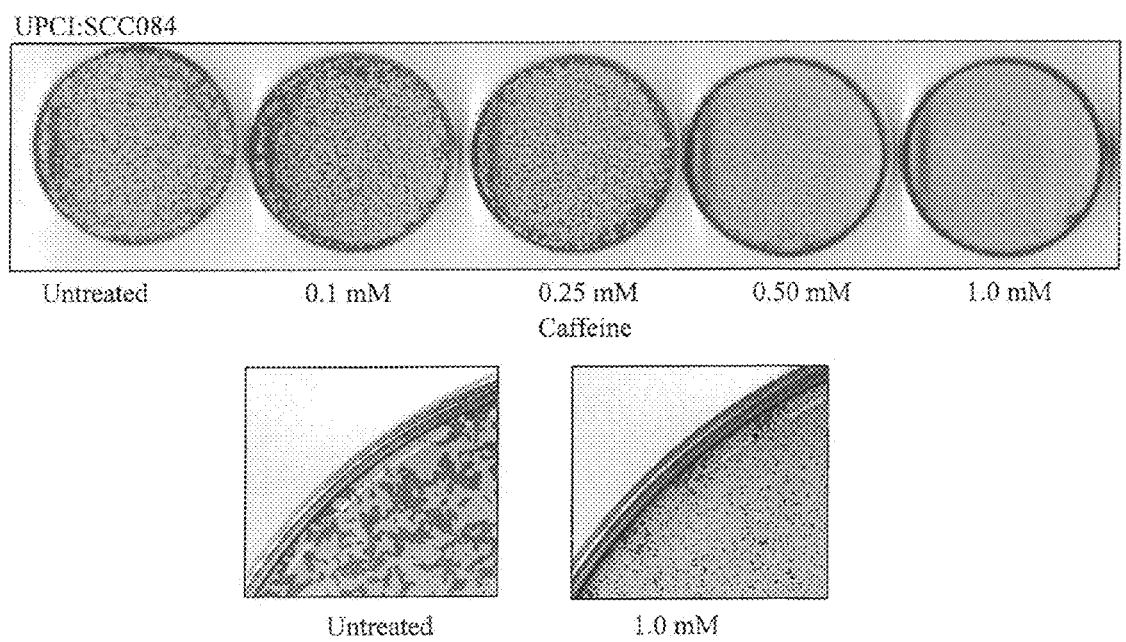

FIG. 19. Clonogenic cell survival of UPCI:SCC084 to different doses of caffeine. Complete inhibition of colony formation in UPCI:SCC084 at a dose of 1 mM caffeine.

Figure 20:
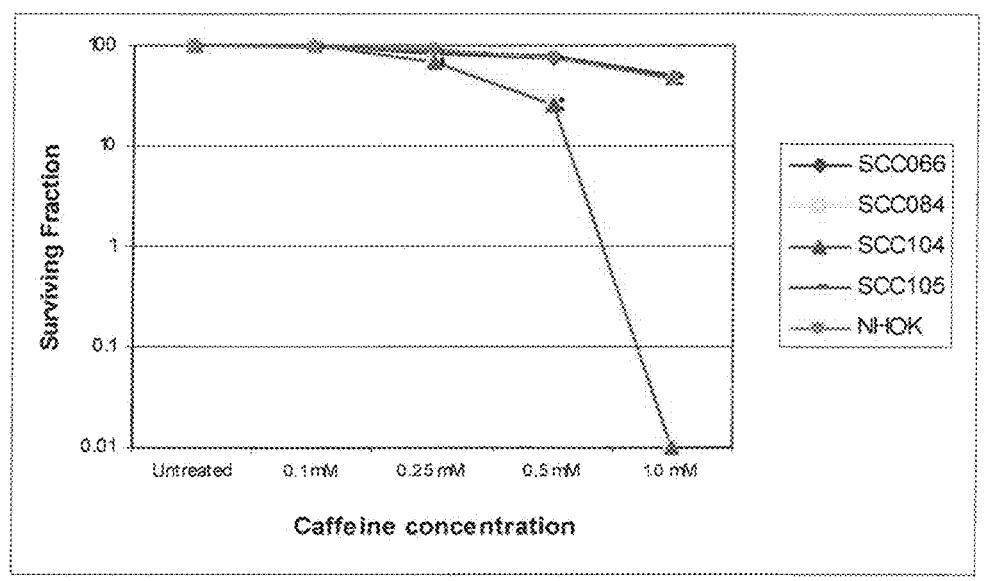

FIG. 20. Clonogenic cell survival of OSCC to different doses of caffeine. UPCI:SCC084 and 104 exhibit increased sensitivity to caffeine compared to UPCI:SCC066, 105 and control NHOK.

FIG. 21. ATR and CHEK1 siRNA mediated protein knockout in UPCI:SCC104. We observed nearly complete loss of ATR and CHEK1 protein expression at the end of 72 h following treatment with ATR and CHEK1 siRNAs respectively.

FIG. 22A-B. Flow cytometric analysis following treatment of ATR and CHEK1 siRNA. Cell cycle profiles of (A) UPCI: SCC104 and (B) UPCI:SCC066 following treatment with non-specific siRNA, ATR siRNA and CHEK1 siRNA in non irradiated cells or cells irradiated with 5 Gy IR are depicted. In comparison to SCC066, SCC104 shows increased accumulation of irradiated cells in the G2M phase. On inhibition of ATR or CHEK1 with the respective siRNAs we observe elimination of the G2M accumulation of irradiated cells and an increase in the sub-G0 dead cell population.

Figure 23:
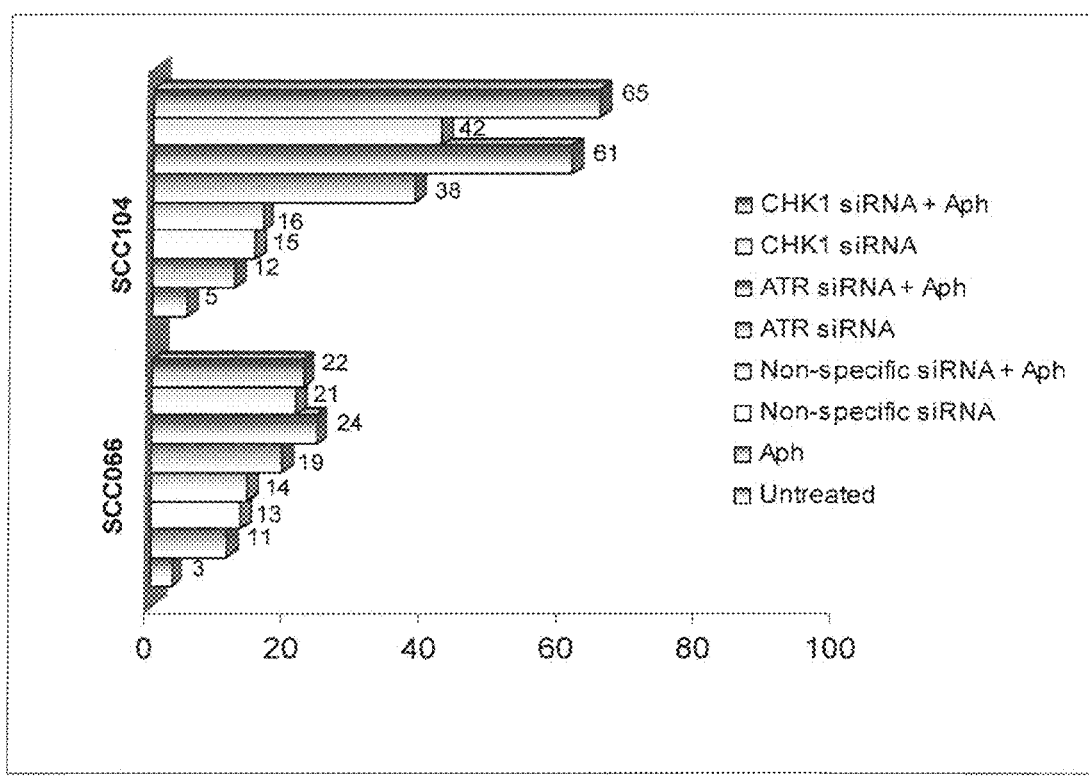

FIG. 23. Induction of premature chromatin condensation and mitotic catastrophe following ATR and CHEK1 siRNA treatment. Frequency of PCC/MC in UPCI:SCC066 and SCC:104 in response to ATR and CHEK1 siRNA treatment with or without aphidicolin (Aph). The numbers next to the bars represent the percentage of mitotic cells undergoing PCC/MC. Bar 1=CHK1 siRNA+Aph; bar 2=CHK1 siRNA; bar 3=ATR siRNA+Aph; bar 4=ATR siRNA; bar 5=non-specific siRNA+Aph; bar 6=non-specific siRNA; bar 7=Aph; and bar 8=untreated.

Figure 24A:
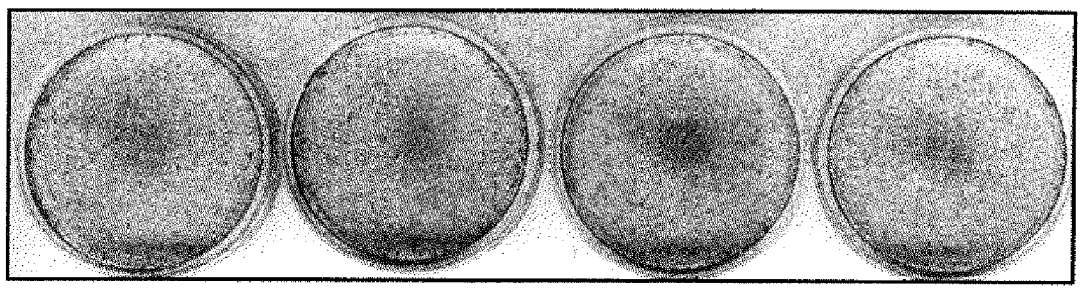
Figure 24B:
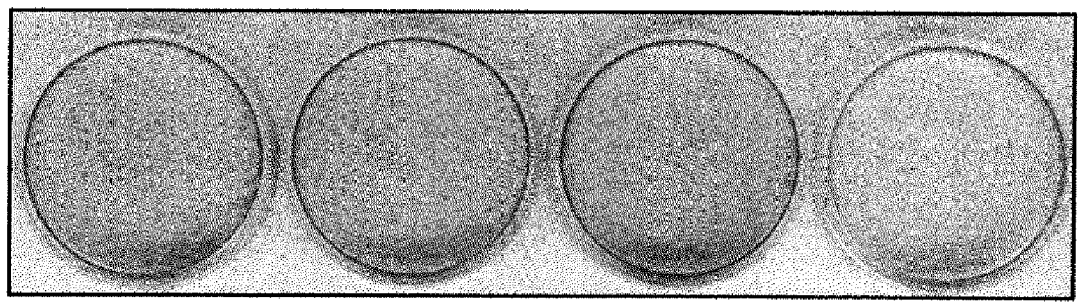

FIG. 24A-B. Clonogenic cell survival of UPCI:SCC066 and 104 to ATR siRNA treatment. UPCI:SCC066 (Panel A) and UPCI:SCC104 (Panel B) cells at 50% confluence were mock treated with empty Lipofectamine or treated with a non-specific scrambled siRNA or treated with ATR siRNA and cell survival was compared to untreated tumor cells for each cell line. A modest reduction in cell survival was observed in UPCI:SCC066, while UPCI:SCC104 cells were highly sensitive to ATR inhibition.

Figure 25:
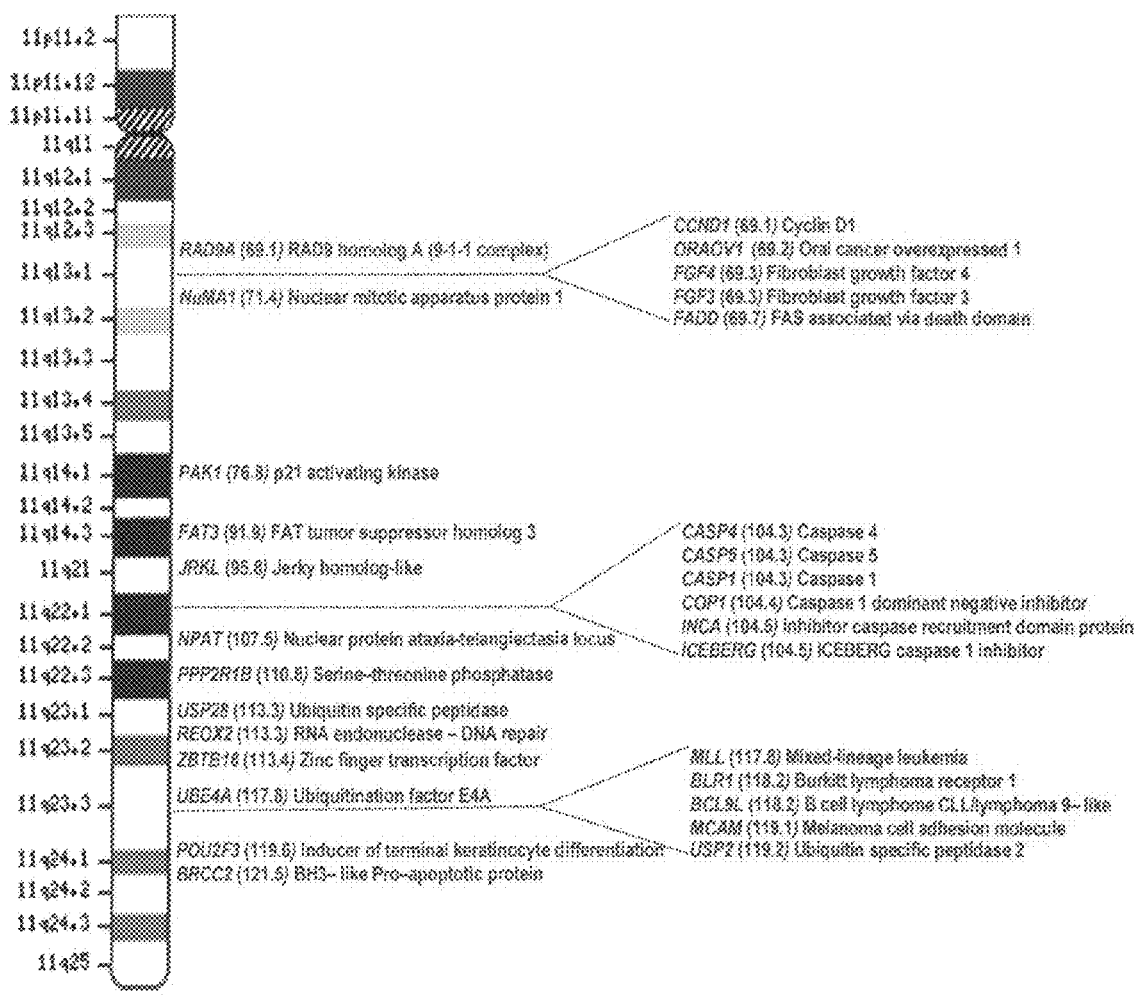

FIG. 25. Important genes that can be amplified or lost on distal 11q.

Figure 26:
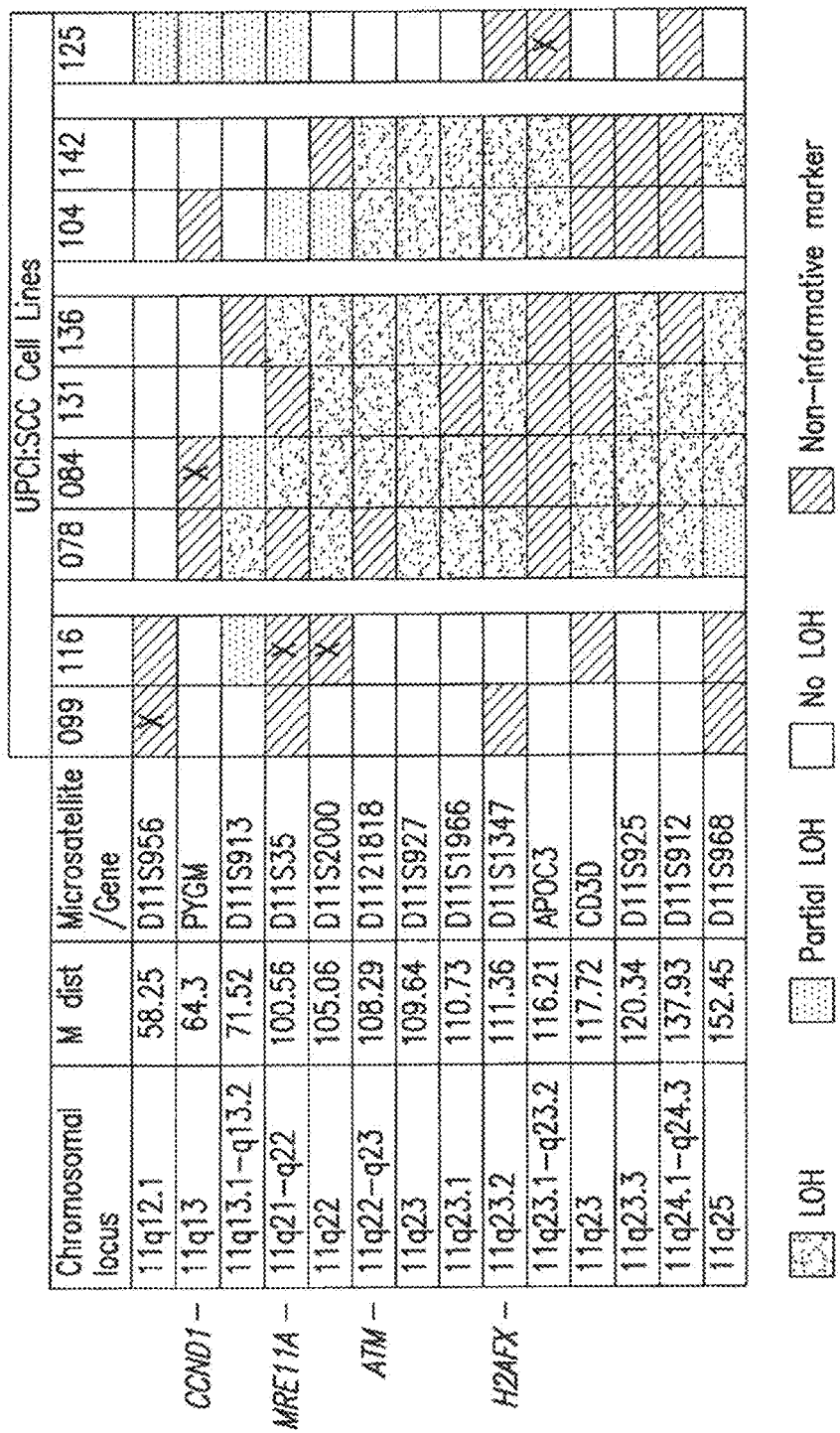

FIG. 26. LOH profiles for a subset of the HNSCC cell lines grouped according to 11q status: "Amplification with Loss" (UPCI:SCC078, 084, 131 and 136), "Loss, No Amplification" (UPCI:SCC104 and 142), "No Amplification, No Loss" (UPCI:SCC099 and 116) and UPCI:SCC125 (heterogeneous, with some tendency toward "distal 11q loss without 11q13 amplification"). The approximate locations of CCND1 in addition to the DNA damage response genes are indicated along the left side of the figure. Also provided, are the map distances from the centromere (in M) and the microsatellite loci or genes that were analyzed for loss of heterozygosity. A key is provided below the figure to indicate the LOH status of each locus in the cell lines. Allelic loss greater than 90% at a given locus was called "LOH," allelic loss greater than 50% was called "partial LOH," and allelic loss less than 50% was considered "no LOH." An "X" indicates an allele mismatch at that particular locus.

Figure 27:
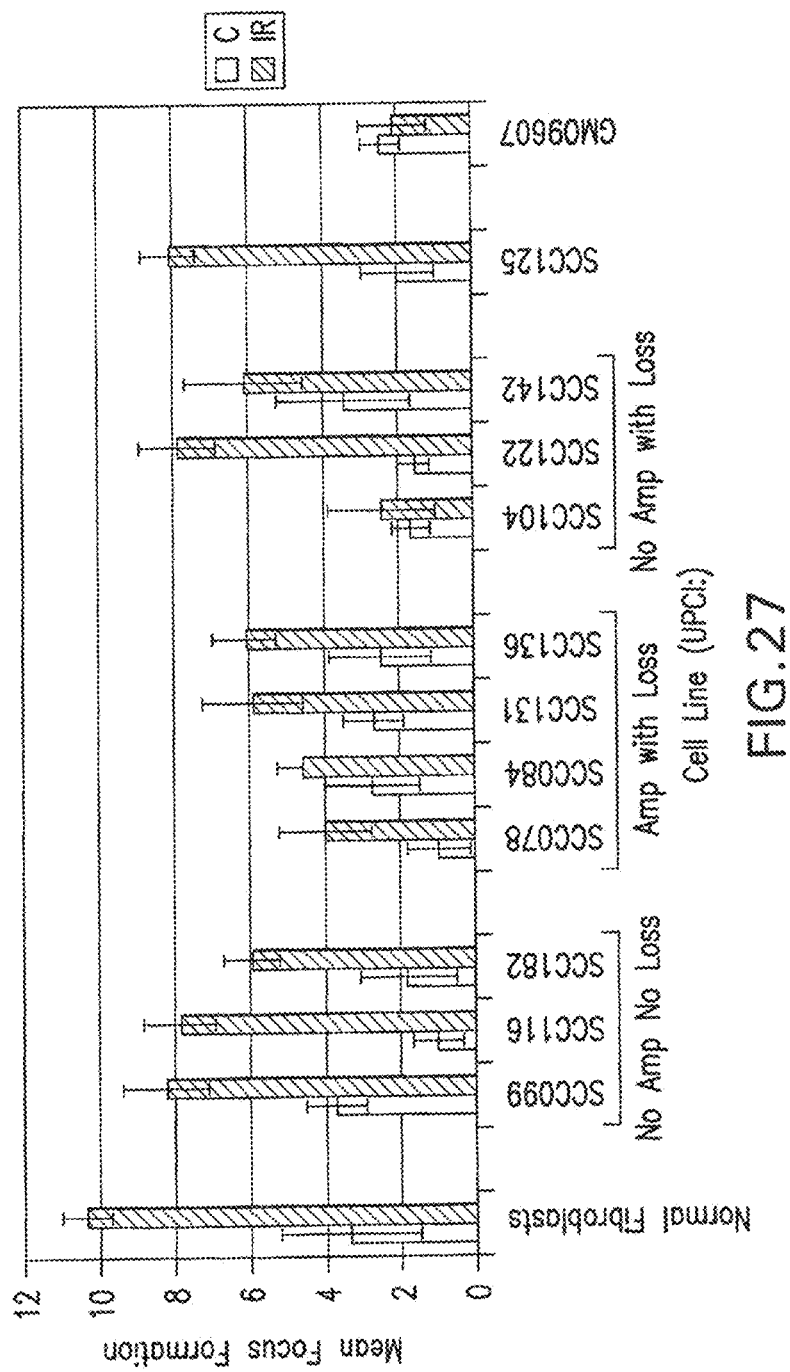

FIG. 27. Phosphorylation of H2AX 1 h after exposure to 2.5 Gy IR. Cell lines are clustered according to 11q status as described previously, with the addition of a normal fibroblast cell line as a positive control and GM09607 as a negative control. The levels of γ-H2AX are shown in mock-treated (C) and after 1 h of repair (IR). Results are derived from a single observer-generated dataset and two independent datasets generated by a spot-counting algorithm on the MetaSystems Metafer scanning system (MetaSystems, Altlussheim, Germany), and displayed as the mean level of focus formation (±95% CI). The mean levels of focus formation after treatment are generally lower in HNSCC cells with loss of distal 11q, irrespective of 11q13 amplification.

Figure 28A:
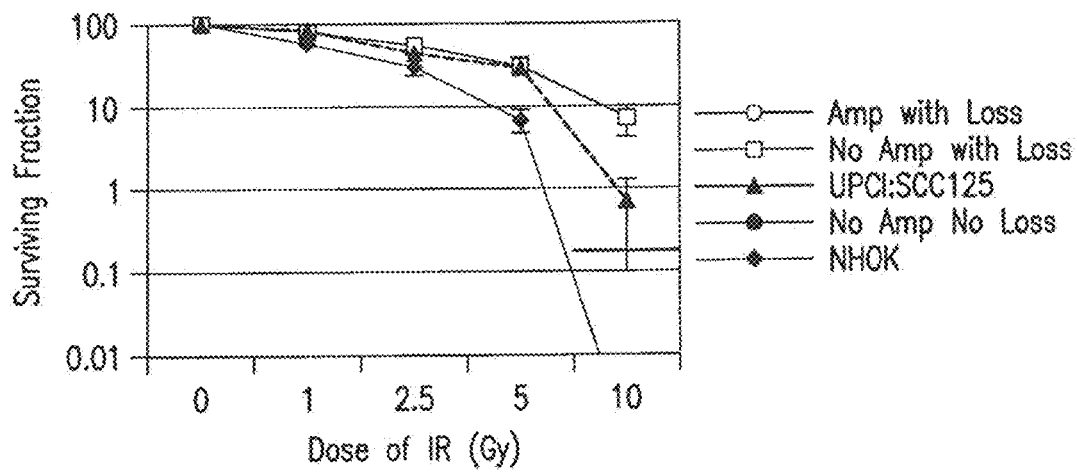
Figure 28B:
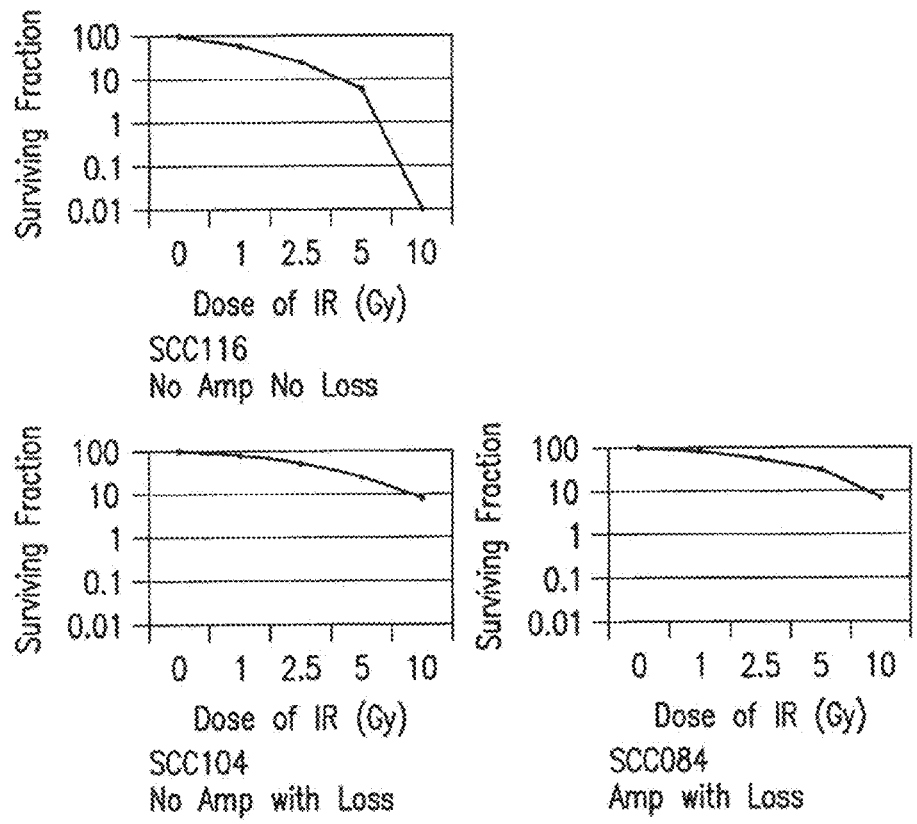

FIG. 28A-B. Results from the clonogenic survival assay. In (A), the surviving fraction of cells at each dose of ionizing radiation is plotted with error bars (±SD) for the HNSCC cell lines sorted by groups. Surviving fraction is plotted on a logarithmic scale. Note that there were no surviving cells remaining for the "No Amplification, No Loss" cell lines or the NHOK cells. HNSCC cells with distal 11q loss show survival at 10 Gy IR, irrespective of 11q13 amplification status. UPCI:SCC125 is seen to have low level survival relative to the cell lines with loss of distal 11q. Individual survival curves (±SD) for the three cell lines are shown in (B). The surviving fraction is plotted on a logarithmic scale. Note that there were no surviving UPCI:SCC116 ("No Amplification, No Loss") cells after 10 Gy IR. In contrast, the two cell lines with distal 11q loss had ~10% of cells surviving 10 Gy IR, irrespective of 11q13 amplification.

Figure 29A:
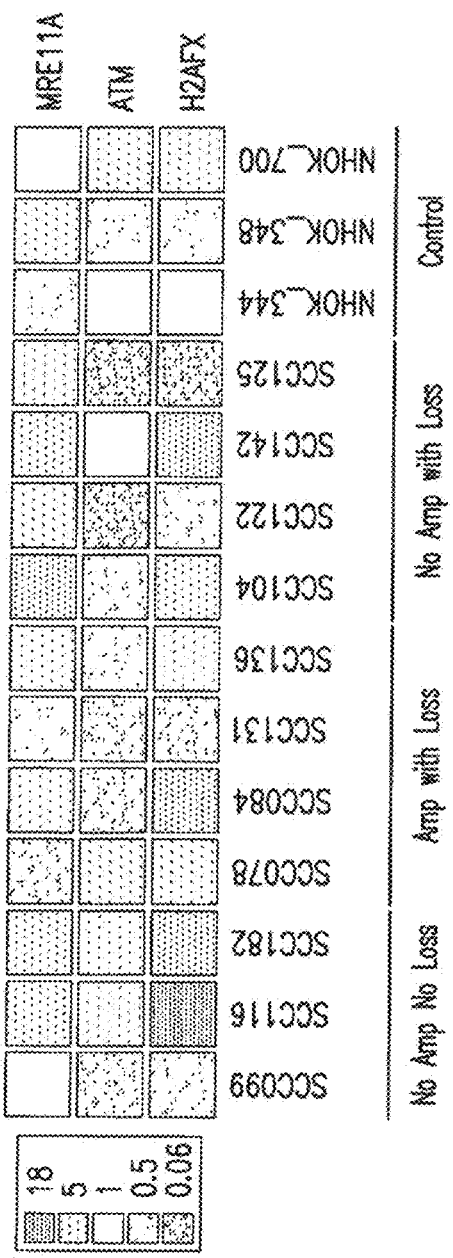
Figure 29B:
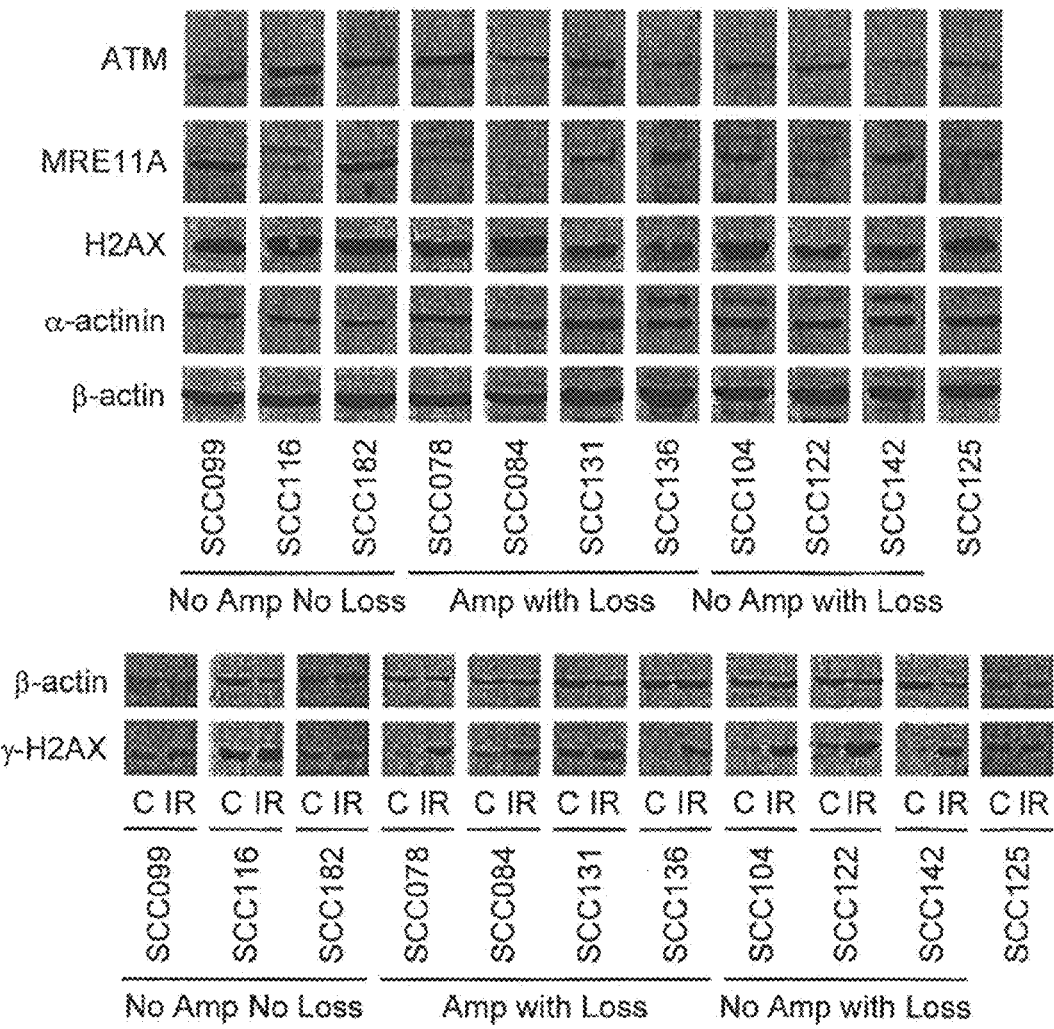

FIG. 29A-B. Expression assays for mRNA and protein. The qRT-PCR expression profiles for the DNA damage response genes assayed in the HNSCC cell lines in (A) Three cell lines with "No Amplification, No Loss," four HNSCC cell lines with "Amplification with Loss," and three cell lines with "No Amplification with Loss." UPCI:SCC125 is included adjacent to the third group, and three NHOK cell lines are provided as controls. A key is provided on the left, indicating the relative fold-changes in expression. (B) The immunoblot data are shown for MRE11A, ATM and H2AX expression in the HNSCC cell lines. Also included is a representation of γ-H2AX induction following 2.5 Gy of IR. MRE11A and ATM were normalized to α-actinin, and H2AX was normalized to α-actin to control for errors in loading prior to a densitometric analysis. The images provided for total protein expression are a composite of two gels, and the images provided for the γ-H2AX expression are a composite of four gels. All protein gels have been truncated to show the band of interest.

Figure 30A:
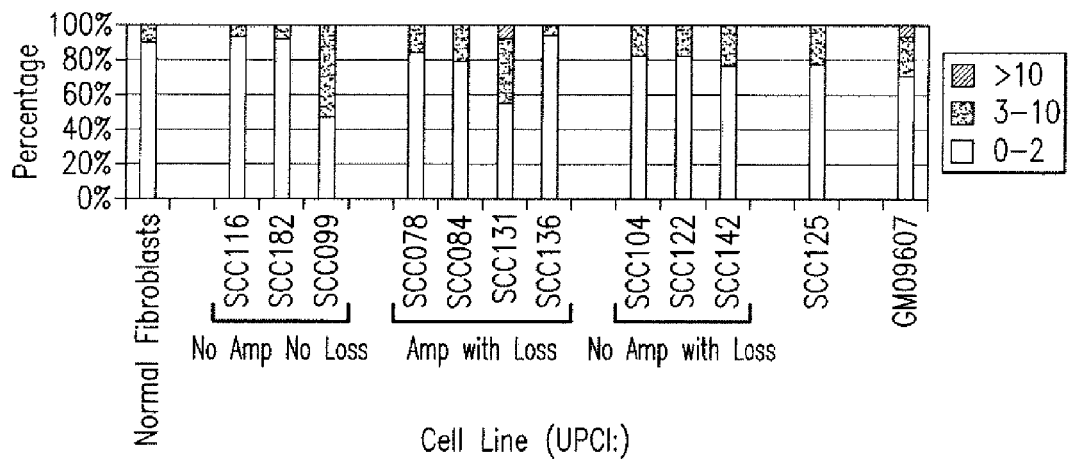
Figure 30B:
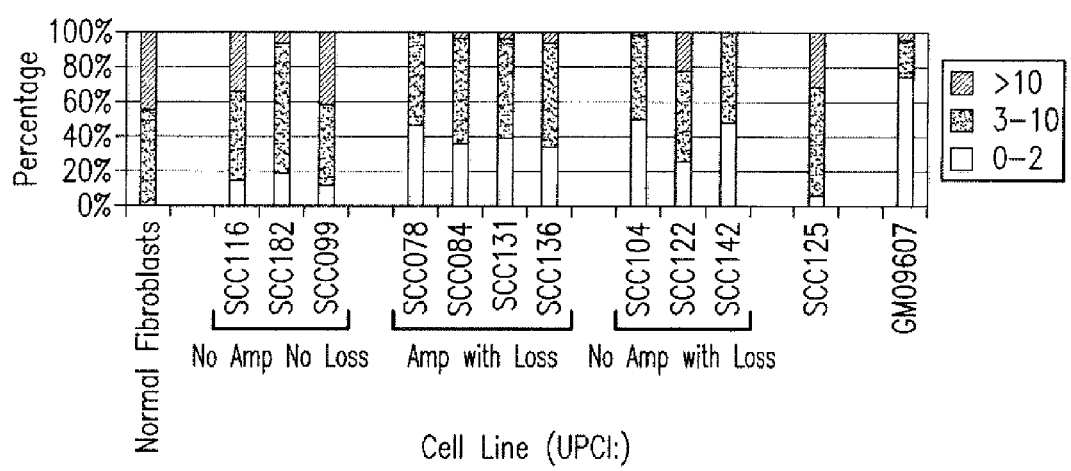

FIG. 30A-B. Stacked column distribution of foci in mock-treated and treated (2.5 Gy) cells. These data are derived from a single experiment, and are intended to complement the mean number of foci per cell. The distribution (0-2, 3-10 and >10 foci) is represented as a percentage contribution to the total number of cells scored in each cell line. In preliminary experiments, 95% of the untreated NHOK had 2 or fewer foci per cell. Therefore, 0-2 foci is the baseline grouping. In (a), the mock-treated populations of cells show primarily 0-2 foci, with some exceptions (UPCI:SCC099 and 131 show slightly high numbers of foci at baseline). In (b), cells treated with 2.5 Gy IR show shifts toward 3-10 or more foci in the population, and fewer cells with 0-2 foci. This shift is most prominent in the normal fibroblasts and "No Amplification, No Loss" HNSCC cell lines as well as UPCI:SCC125. In contrast, the GM09607 cells show little change in focus distribution in mock-treated and treated populations.

Figure 31:
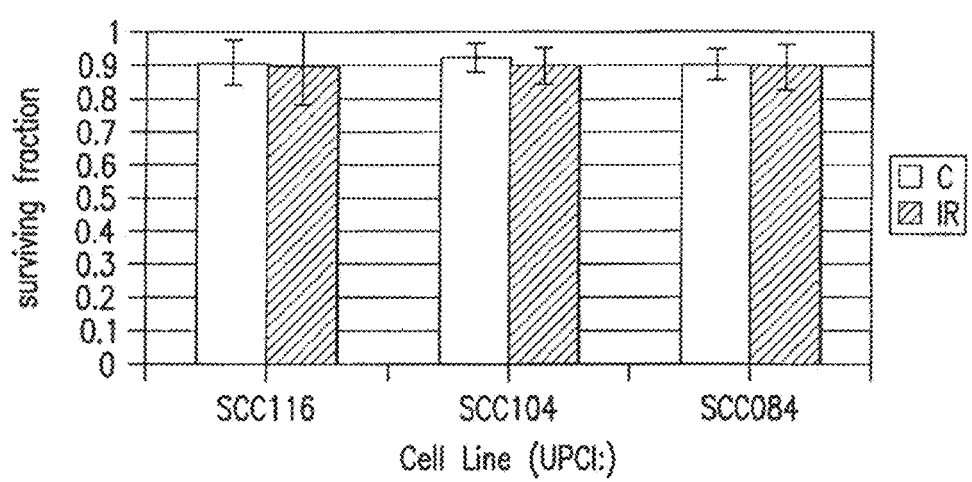

FIG. 31. Results from a viability assay in representative cell lines. Cellular viability was assessed under the same conditions as γ-H2AX immunofluorescence, in order to predict what fraction of cells with foci were not undergoing repair (apoptotic). This viability assay is based on the integrity of the cell membrane. Results for the assay carried out in triplicate are presented as 95% confidence intervals, and indicate that there is equivalent survival in treated and mock-treated populations. Based on these findings, any cell death seen in 1 h is not attributable to the effect of treatment. The implication is that the small numbers of non viable cells encountered during the focus formation assay did not influence the sample mean or distribution of foci representative of DNA double strand breaks.

FIG. 32A-B. Western blots showing p53 status of (a) oral squamous carcinoma and (b) non-small cell lung carcinoma and ovarian carcinoma cell lines as assessed by the presence of p53 and p21 proteins after a 4-hour treatment with adriamycin.

Figure 33:
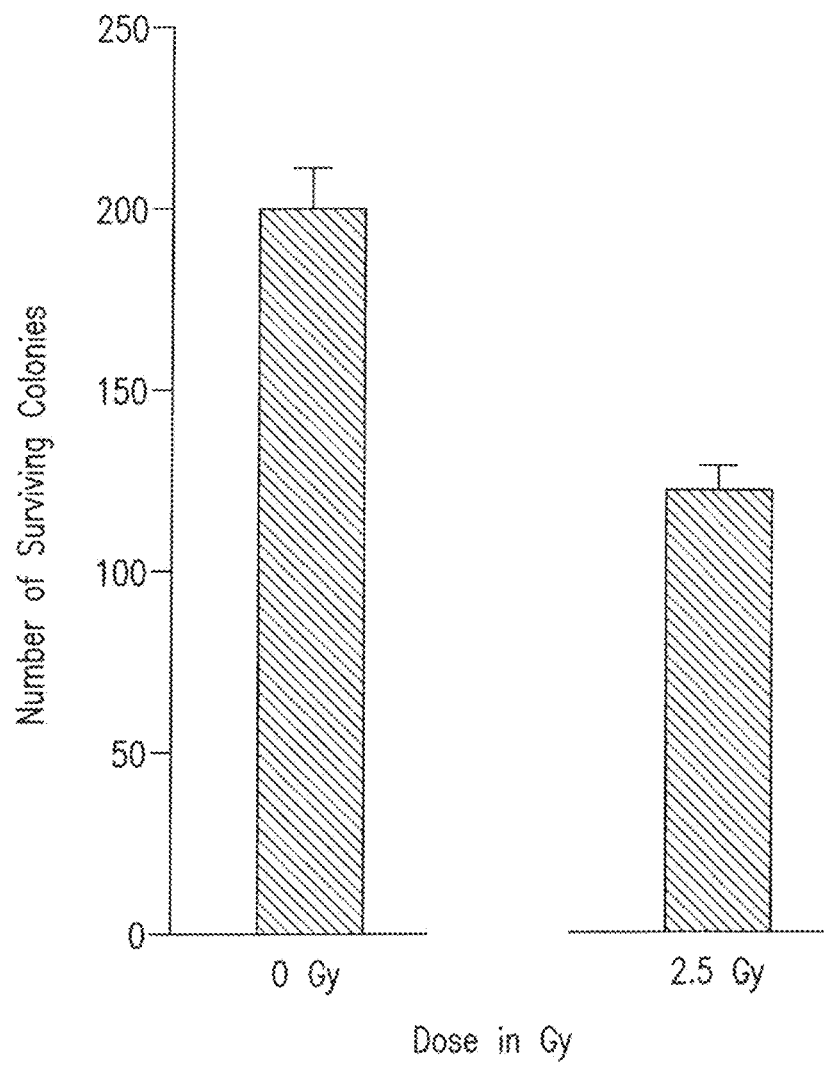

FIG. 33. Clonogenic cell survival of ES-2 (without active p53) ovarian carcinoma cells treated with 2.5 Gy irradiation versus non-irradiated control.

Figure 34:
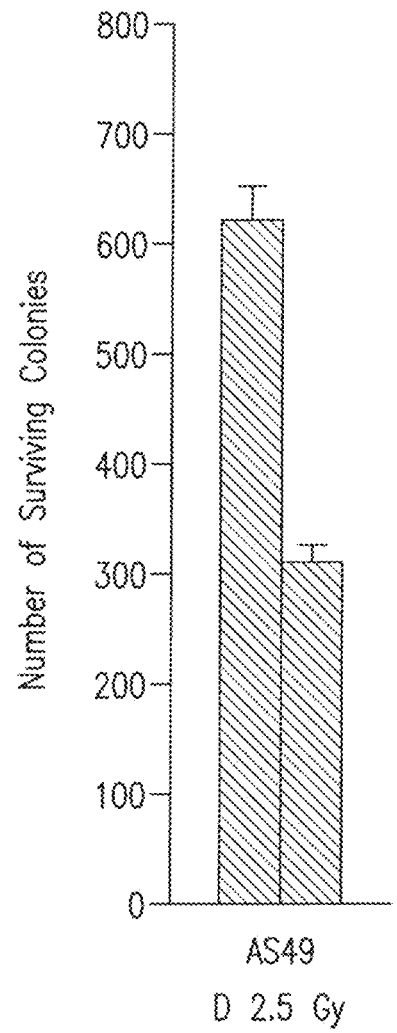

FIG. 34. Clonogenic survival of AS49 (with active p53) cells treated with 2.5 Gy irradiation versus non-irradiated control.

Figure 35:
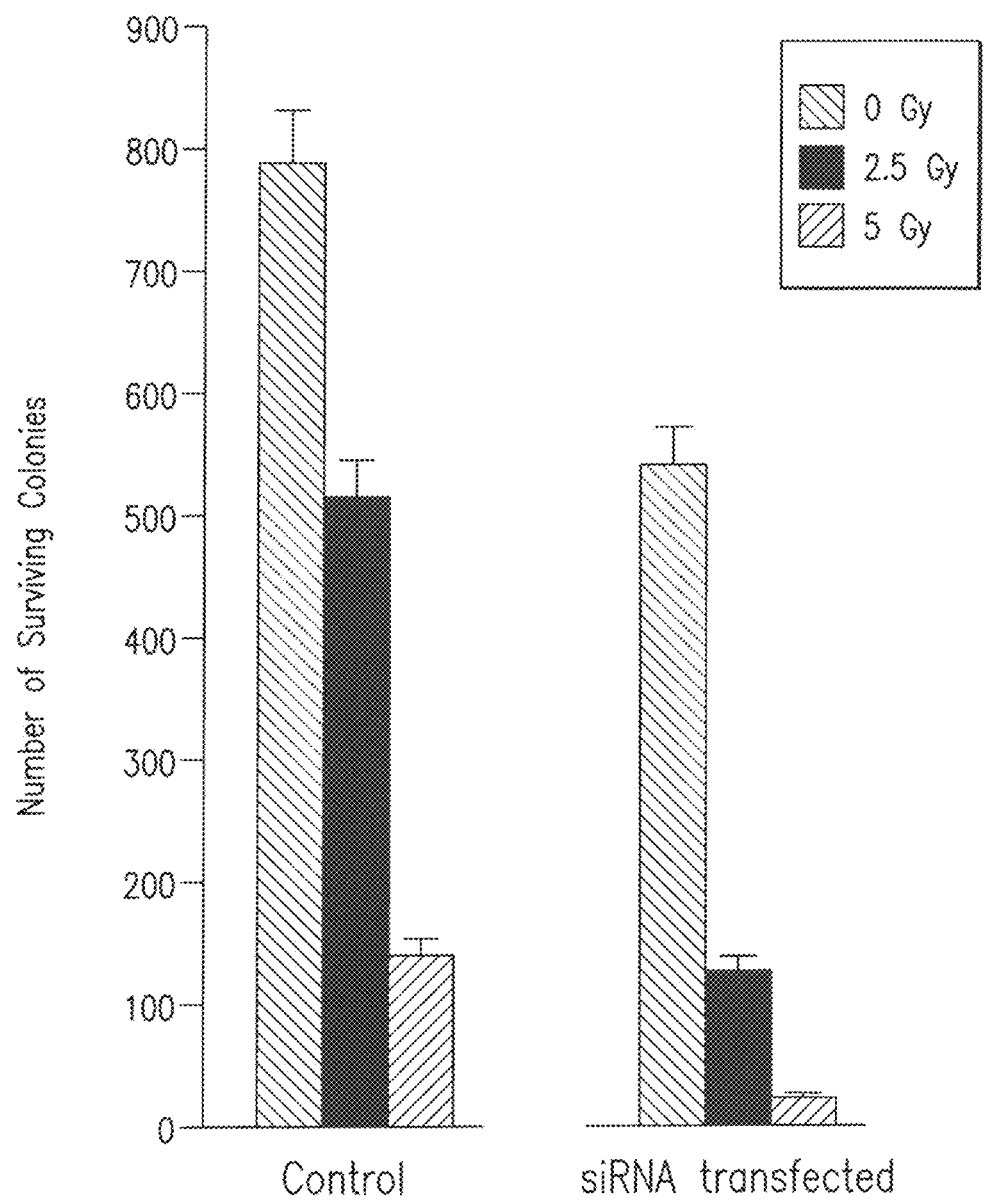

FIG. 35. Clonogenic survival of UPCI:SCC040 (without active p53) cells either non-irradiated or irradiated with either 2.5 or 5 Gy of radiation and either untreated (control) or treated with siRNA to CHEK1.

5. DETAILED DESCRIPTION OF THE INVENTION

For clarity of description, and not by way of limitation, the present invention is divided into the following subsections:

(i) methods of identifying 11q deletion;
(ii) methods of identifying ATR/CHEK1/CCND1/p53 copy number alterations and/or overexpression;
(iii) methods of identifying target patients;
(iv) methods of treating target patients; and
(v) kits.

5.1 Methods of Identifying 11q Deletion

In one non-limiting aspect of the invention, the present invention provides for identifying an 11q deletion in a patient sample.

The term "11q deletion" refers to a deletion in the long arm of human chromosome 11 which comprises at least a part of the ATM gene and may further comprise at least a portion of MRE11A, H2AFX, and/or CHEK1.

A patient sample is a sample that contains genomic material. For example, but not by way of limitation, the sample may be a cell, a tissue, or DNA. In a specific, non-limiting embodiment, the sample comprises a cancer cell.

The deletion in 11q may be identified by any method known in the art. In non-limiting embodiments, it may be detected using a nucleic acid probe representing a gene or non-coding sequence located on 11q, preferably ATM, MRE11A, H2AFX, CHEK1, genes located at 11q21-23 such as, but not limited to, BACE, BLR1, CBL, DDX10, DFNB24, DLAT, DNCH2, FRA11H, FSGS2, G6PT1, HEPHL1, HSPB2, etc. (a list of genes located on 11q may be found at (http://www.gdb.org/gdbreports/GeneByChromosome.11.alpha.html or http://genome.uc-sc.edu) or in other genome databases known the skilled artisan. Sequences from this region preferably lacking a repeated element may also be used. In non-limiting embodiments, single nucleotide polymorphism (SNP) analysis may be used to show copy number loss. The following Table 1 sets forth genes which may be lost with an 11q deletion.

TABLE 1

| Gene name | Location | Distance from centromere | Function |
|---|---|---|---|
| PAK1 | 11q13.5 | 76.8 Mb | P21 activating kinase regulates cell motility and morphology |
| FAT3 | 11q14.3 | 91.9 Mb | Tumor suppressor homolog of *Drosophila* FAT |
| JRKL | 11q21 | 95.8 Mb | Nuclear factor |
| DDI1 | 11q22.3 | 103.4 Mb | Induced in response to DNA damage |
| CASP1, 4, 5 | 11q22.1-22.3 | 104.3 Mb | Effectors of apoptosis |
| INCA | 11q22.3 | 104.5 Mb | Regulates recruitment and activation of procaspase 1 |
| ICEBERG | 11q22.3 | 104.5 Mb | Caspase 1 inhibitor |
| NPAT | 11q22.3 | 107.5 Mb | Nuclear |
| PPP2R1B | 11q23 | 110.8 Mb | Protein phosphatase regulatory subunit |
| REXO2 | 11q23.1 | 113.2 Mb | 3'-5' exonuclease involved in DNA repair |
| USP28 | 11q23.1 | 113.3 Mb | De-ubiquitinating enzyme |
| ZBTB16 | 11q23.1 | 113.4 Mb | Zinc finger transcription factor regulates histone deacetylase and cell cycle progression |
| UBEA | 11q23.3 | 118 Mb | Conjugation factor required for poly- and multi ubiquitination |
| POU2F3 | 11q23.3 | 119.6 Mb | Induces terminal keratinocyte differentiation |
| BRCC2 | 11q24.1 | 121.5 Mb | BH3-like domain containing pro-apoptotic protein |

In non-limiting embodiments of the invention, loss of 11q may correlate with an increase in expression in cyclin D1 (CCND1), so that an increase in expression of CCND1 may be used as an indicator of loss of 11q (an increase in CCND1 expression is consistent with loss of 11q, although loss of 11q does not necessarily result in an increase in expression of CCND1). Further genes which may be lost or amplified are shown in FIG. 25.

The nucleic acid probe may be hybridized to genomic DNA in the form of a chromosome (e.g., by fluorescence in situ hybridization ("FISH")). Quantitative Microsatellite Analysis (QuMA) may be used to detect copy number changes in microsatellite markers along chromosome arm 11q. PCR primers sequences for the microsatellite loci are shown in Appendix D. In a specific non-limiting example, (see Section 7), the TaqMan CA-repeat fluorogenic probe 5'-FAM (6-carboxy fluorescein)-TGTGTGTGTGTGTGT-GTGTGT-TAMRA (6-carboxytetramethylrhodamine)-3' (SEQ ID NO:26) may be used (Integrated DNA Technologies, Coralville, Iowa). Other methods would include quantitative DNA PCR, loss of heterozygosity (LOH) analysis, or array comparative genomic hybridization ("CGH") to identify 11q deletion and gene loss. In each case, it is preferable to include, in the study, a control probe, such as a chromosome 11 centromere probe.

In alternative embodiments, 11q deletion may be identified by karyotype analysis, preferably with attention to the 11q22 region where the ATM gene resides.

In a preferred, non-limiting embodiment, as exemplified in section 6 below, dual-color FISH may be performed along with BAC probes to one or more of MRE11A, ATM, H2AFX and CHEK1 along with a centromere 11 enumeration probe (CEP 11; D11Z1) (Vysis/Abbott Molecular Inc., Des Plaines, Ill.). This working example provides non-limiting examples of probes which may be used. (See also Appendix A).

5.2 Methods of Identifying ATR/CHEK1/CCND1 Copy Number Alterations and/or Overexpression In non-limiting aspects of the invention, the present invention provides for identifying overexpression of ATR and/or CHEK1 and optionally CCND1 and/or p53 (and/or p53 activity) in a patient sample.

Any method known in the art may be used to measure expression of ATR and/or CHEK1 and optionally CCND1 and/or p53.

As one non-limiting example, the location and copy number of ATR and/or CHEK1 and optionally CCND1 and/or p53 may be determined using FISH.

In a specific non-limiting example, ATR may be present in amplified form on chromosome 3 (again, preferably a control probe, such as a chromosome 3 centromere probe, may be included as a control).

As one non-limiting example, quantitative real-time or reverse transcriptase PCR ("qRT-PCR") may be used to measure expression of ATR and/or CHEK1 and optionally CCND1 and/or p53.

As another non-limiting example, a Northern blot may be used to measure expression of ATR and/or CHEK1 and optionally CCND1 and/or p53.

As another non-limiting example, the level of ATR and/or CHEK1 and optionally CCND1 protein and/or p53 may be measured using a method known in the art (e.g. a Western blot or immunohistochemically).

For example, but not by way of limitation, the sequence of ATR may be accessed as Genbank Acc. No. NM_001184; the sequence of CHEK1 may be accessed as Genbank Acc. No. NM_001274; and the sequence of CCND1 may be accessed as Genbank Acc. No. NM_053056.

"Overexpression" as that term is used herein means an increase of at least about two-fold or at least about five-fold, or preferably at least about ten-fold in the RNA or protein level for a particular gene, compared to expression in normal control cells.

Specific non-limiting examples of nucleic acid probes (defined to include hybridization probes as well as primers) may be found in Section 6 and Appendices A and B, below. Specific non-limiting examples of antibodies which may be used to measure protein levels are presented in Appendix C.

Further, the presence of active p53 may be evaluated by determining whether or not a gene downstream of p53 in an induction pathway is induced. One non-limiting example of such a gene is p21 (Lee et al., 200, Proc. Natl. Acad. Sci. U.S.A. 97:8302-8305, incorporated by reference). Induction of a gene may be evaluated using a method of determining protein expression as known in the art, including those methods described above.

5.3. Methods of Identifying Target Patients

A "target patient", as that term is used herein, is a patient who falls within a subset of patients having a cancer which is more likely to be resistant or refractory to radiation (or other free radical based) therapy or chemotherapy and/or which may benefit from a treatment which includes inhibition of the ATR/CHEK1 pathway.

A "target patient" may suffer from any cancer. In preferred non-limiting embodiments of the invention, the cancer is a squamous cell carcinoma, more preferably a squamous cell carcinoma of the head or neck region ("HNSCC"), most preferably oral squamous cell carcinoma ("OSCC"). Other cancers associated with ATM copy number change or mutation which may benefit from the present invention include, but are not limited to, melanoma, ovarian cancer, lung cancer, kidney cancer, leukemia, lymphoma, multiple myeloma, pancreatic cancer, prostate cancer, colon cancer, esophageal cancer, cervical cancer, and breast cancer.

Accordingly, the present invention provides for a method of identifying a patient suffering from a cancer which is likely to be refractory to therapy based on ionizing radiation or other free-radical generating method and/or chemotherapy, and/or which is likely to benefit from (i.e. be treatable by) inhibition of the ATR/CHEK1 pathway, comprising (i) identifying an 11q deletion in a patient sample considered to be representative of the cancer (e.g., a tumor sample, or a tumor cell, or a malignant cell not associated with a solid tumor, or a DNA sample from one of the foregoing, etc.) and/or (ii) identifying, in the patient sample, overexpression of ATR and/or CHEK1 and/or CCND1 and optionally (iii) determining whether p53 expression and/or activity is decreased or absent, wherein an 11q deletion and/or overexpression of ATR and/or CHEK1 and/or CCND1 and/or a decrease in expression and/or activity of p53 indicates that the cancer is likely to be resistant or refractory to therapy based on ionizing radiation or other free-radical generating method and/or is likely to benefit from inhibition of the ATR/CHEK1 pathway.

In a related embodiment, the present invention provides for a method, which may be a further step in the method described in the preceding paragraph, of identifying a patient suffering from a cancer which is likely to be refractory to therapy based on ionizing radiation or other free-radical generating method and/or chemotherapy, and/or which is likely to benefit from inhibition of the ATR/CHEK1 pathway, comprising (i) exposing cells in a patient sample considered to be representative of the cancer to a source of free-radicals such as ionizing radiation; and (ii) determining whether there is a higher percentage of cells in the S and G2M phases relative to control cells (representative of normal tissue); where a higher percentage of cells in the S and G2M phases indicates that the cancer is likely to be refractory to therapy based on ionizing radiation or other free-radical generating method and/or chemotherapy and/or is likely to benefit from inhibition of the ATR/CHEK1 pathway.

5.4 Methods of Treating Target Patients

The present invention provides for a method of treating a target patient in need of such treatment with an effective amount of an inhibitor of the ATR/CHEK1 pathway as part of a treatment regimen that includes at least one DNA-damaging agent. In preferred non-limiting embodiments, the target patient has been identified as likely to benefit from such therapy using a method described in the preceding section.

Inhibitors of the ATR/CHEK1 pathway include inhibitors which specifically inhibit the expression and/or function of ATR and/or CHEK1. Non-limiting examples include siRNA, antisense, and catalytic RNAs which share homology with the ATR or CHEK1 genes, including mixtures thereof. For example, but not by way of limitation, the sequence of ATR may be accessed as Genbank Acc. No. NM_001184; and the sequence of CHEK1 may be accessed as Genbank Acc. No. NM_001274. These RNA inhibitors may be, in non-limiting embodiments, nucleic acids between about 15 and 100 bp, or between about 15 and 50 bp, or between 15 and 30 bp in length, and may contain deoxyribonucleosides or non-natural bases. Small molecule inhibitors, such as chemical inhibitors of the protein, receptor, or specific monoclonal antibodies may be used. Small molecule inhibitors include, but are not limited to CHIR-124, XL844, A-690002, A-641397 and A-901592 (see, e.g., Chen, et al., 2006, Intl. J. Cancer 119: 2784-2794). Said inhibitor(s) may be administered by any suitable route, including, but not limited to, intravenous, intra-arterial, intrathecal, intra-peritoneal, subcutaneous, intranasal, pulmonary inhalation, and direct instillation into the tumor or tumor bed following complete or partial surgical resection.

DNA-damaging agents which may be used according to the invention include, but are not limited to, ionizing radiation, either applied externally or using a radioactive implant, or free radical generators, for example, but not limited to, chemotherapeutic agents (e.g., that bind to DNA) and ultraviolet radiation.

The DNA-damaging agent may be administered to the patient prior to, concurrently with, or subsequent to, administration of the inhibitor of ATR/CHEK1, however, it is desirable to select the timing of administration of both agents so that the effect of the DNA-damaging agent is not suppressed by overexpression of ATR and/or CHEK1 and/or activation of the ATR/CHEK1 pathway. Preferably, but not by way of limitation, the DNA-damaging agent is administered within 24 hours of inhibiting ATR and/or CHEK1.

ATR/CHEK1 inhibitor together with DNA-damaging agent, used according to the invention, may be administered as part of a treatment regimen which includes concurrent or sequential treatment with one or more other anti-cancer agent, including but not limited to conventional chemotherapeutic agents and cytokines, such as cisplatinum, paclitaxel, 5-fluorodeoxyuridine, and/or carboplatinum.

In non-limiting embodiments, the invention provides for a method of treating a patient suffering from a cancer, comprising (i) identifying the patient as being likely to benefit from inhibition of the ATR/CHEK1 pathway by a method comprising (a) identifying an 11q deletion in a patient sample considered to be representative of the cancer and/or (b) identifying, in the patient sample, overexpression of a gene selected from the group consisting of ATR, CHEK1, CCND1 and a combination thereof, wherein an 11q deletion and overexpression of ATR, CHEK1, CCND1 or a combination thereof, indicates that the cancer is likely to benefit from inhibition of the ATR/CHEK1 pathway; and (ii) treating the patient with an inhibitor of the ATR/CHEK1 pathway.

In further non-limiting embodiments, the present invention provides for a method of treating a patient suffering from a cancer, comprising (i) identifying the patient as being likely to benefit from inhibition of the ATR/CHEK1 pathway by a method comprising (a) identifying an 11q deletion in a patient sample considered to be representative of the cancer and/or (b) identifying, in the patient sample, overexpression of a gene selected from the group consisting of ATR, CHEK1, CCND1 and a combination thereof, and (c) identifying, in the patient sample, a decrease in p53 expression and/or activity wherein an 11q deletion and overexpression of ATR, CHEK1, CCND1 or a combination thereof and/or a decrease in p53 expression and/or activity indicates that the cancer is likely to benefit from inhibition of the ATR/CHEK1 pathway; and (ii) treating the patient with an inhibitor of the ATR/CHEK1 pathway.

5.5 Kits

The present invention further provides for kits that comprise elements that may be used to identify a deletion in 11q as well as overexpression of ATR and/or CHEK1 and optionally CCND1. Such a kit may comprise nucleic acid probes for identifying and/or directly or indirectly detecting an ATM gene and one more gene selected from the group consisting of ATR, CHEK1, CCND1, MRE11A and H2AFX.

A "nucleic acid probe" as that term is used herein includes but is not limited probes suitable for hybridization (e.g., for FISH) as well as primers (e.g., for PCR or QRT-PCR); said nucleic acids may be between about 15 and 200, or between about 20 and 100, or between about 15 and 50 nucleotides in length or larger (e.g., 100-200 kb for a FISH probe), and capable of hybridizing to the gene of interest, for example under conditions suitable for FISH or QRT-PCR.

A kit may further optionally comprise one or more antibody directed toward ATM, ATR, CHEK1, MRE11A, H2AFX, CCND1 or CHEK2 protein with or without phosphorylation.

A nucleic acid probe or antibody contained in such a kit may itself be detectably labeled or may be indirectly detectable via a detectable molecule capable of binding to said probe or antibody.

A detectable label provides a signal which may be, for example, but not be way of limitation, fluorescent, radioactive, pigmented, etc.

6. EXAMPLE

The DNA Damage Response Pathway in Oral Squamous Cell Carcinoma

Oral squamous cell carcinomas are a good model system for analyzing genetic alterations relating to chromosome 11, since nearly 45% of OSCC are characterized by amplification of chromosomal band 11q13, which occurs by a breakage-fusion-bridge ("BFB") cycle mechanism. The first step in the BFB cycle involves breakage and loss of distal 11q. Consequently, numerous genes, including critical genes involved in the DNA damage response pathway (e.g., MRE11A, ATM, and H2AFX) are lost in the step preceding 11q13 amplification.

The experiments described herein were designed, in part, to evaluate the effect of loss of genes on distal 11q on the DNA damage response in OSCC, which is representative of other cancers which are associated with distal 11q loss. Characterization of OSCC using FISH revealed partial loss of MRE11A, ATM, and H2AFX in all cell lines with 11q13 amplification and in addition lines lacking this amplification. Quantitative microsatellite analysis and loss of heterozygosity studies confirmed the distal 11q loss. Reverse transcriptase quantitative PCR and immunoblotting revealed reductions in RNA and protein expression of MRE11A, ATM and H2AFX that correlated with genetic loss. All cell lines with distal 11q loss exhibited a decrease in the size and number of γ-H2AX foci and increased chromosomal instability following treatment with ionizing radiation. Surprisingly, distal 11q loss was also correlated with reduced sensitivity to ionizing radiation. Although the literature attributes the poor prognosis in OSCC and other cancers to 11q13 amplification, the results presented herein indicate that distal 11q deletions may be equally if not more significant.

Further, the ATR/CHEK1 pathway was found to be upregulated in a subset of OSCC. The experiments described herein were performed, in part, to determine whether the upregulated ATR/CHEK1 pathway protects OSCC from premature chromatin condensation or mitotic catastrophe (leading to cell death) by enhancing the S phase and G2 phase checkpoints, and to evaluate whether inhibiting this pathway would sensitize OSCC to DNA damaging agents.

As described below, a gain in ATR gene copy number, but a partial loss of CHEK1 at the gene level, was observed in OSCC. However, in a subset of OSCC cells with loss of the G1 cell cycle checkpoint, overexpression of both ATR and CHEK1 was observed. Nonspecific inhibition of ATR or CHEK1 with caffeine or specific inhibition with the respective siRNAs was found to result in increased susceptibility of OSCC to DNA damaging agents, including ionizing radiation.

6.1 Materials and Methods

Subjects and Sample Collection. OSCC cell lines were established from tumors surgically removed from anonymous consenting, previously untreated patients. Normal human keratinocytes (NHOK) were established from uvulopalatopharyngeal tissue obtained from University of Pittsburgh Medical Center. The tissue was collected from anonymous consenting patients with IRB approval. Peripheral blood for FISH was collected from normal anonymous donors. GM09607, AT fibroblast cell line was purchased from Coriell Cell Repositories. The OKF6/TERT-1 cell line was obtained from Dr. Jim Rheinwald.

Cell Culture. Eleven OSCC cell lines were selected for the distal 11q loss study and twenty OSCC cell lines were selected for ATR and CHEK1 studies from the OSCC established in the laboratory. The ATM—deficient, AT cell line (GM09607) was used as a positive control since it is documented to have an upregulated ATR-CHEK1 pathway, and normal human oral keratinocytes (NHOK), OKF6/TERT-1 and/or HEK293 cell line were used as negative controls.

OSCC Cell Lines. SCC were cultured in M10 medium composed of Minimal Essential Medium (Gibco Invitrogen, Grand Island, N.Y.), supplemented with 1% non-essential amino acids, 1% L-glutamine, 0.05 mg/ml gentamicin and 10% fetal bovine serum (FBS) (Gibco Invitrogen). For subculturing OSCC, adherent cells were detached from the flask surface by trypsinizing with 0.05% trypsin and 0.02% EDTA (Irvine Scientific) for 3-5 min at 37° C. in 5% CO2 incubator. Equal amounts of M10 medium were used to inhibit trypsin activity following detachment and cells were replated.

AT Null Cell Line. GM09607 (Coriell Cell Repositories, Camden, N.J.) was cultured using Dulbecco's Modified Eagle Medium (DMEM) (Gibco Invitrogen), supplemented with 1% non-essential amino acids, 0.05 mg/ml penicillin-streptomycin-L-glutamine, and 10% FBS. Subculturing was performed as described for OSCC.

Controls. Anonymous NHOK cells established from uvulopalatopharyngoplasty specimens were used as controls. In brief, NHOK cells were cultured in serum-free KGM-2 medium (Clonetics, Walkersville, Md.), supplemented with bovine pituitary extract (BPE), hEGF, insulin (bovine), hydrocortisone, GA-1000 (Gentamicin, Amphotericin B), epinephrine and transferrin as per the manufacturer's instructions (supplements supplied in the KGM-2 BulletKit™, Clonetics). The hTERT cells were cultured in Keratinocyte-SFM supplemented with 25 µg/ml BPE, 0.2 ng/ml epidermal growth factor, 0.3 mM CaCl2 and penicillin-streptomycin (Gibco Invitrogen). These keratinocytes were expanded to high density in a 1:1 mixture of Keratinocyte-SFM and DMEM-F12. The DMEM-F12 was a 1:1 mixture of calcium-free and glutamine-free DMEM and Ham's F-12 supplemented with 25 µg/ml bovine pituitary extract, 0.2 ng/ml epidermal growth factor, 1.5 mM L-glutamine and penicillin-streptomycin (Gibco Invitrogen).

Preparation of DNA Probes for FISH A single colony of E. coli carrying the individual BAC (mapping to ATR, ATM, CHEK1, CCND1 H2AFX, MRE11A and TP53) (Individual BAC numbers are listed in Appendix A) was incubated overnight at 37° C. in 5 ml of Luria-Bertani (LB) medium with 50 µg/ml Chloramphenicol. The bacteria were centrifuged at 10,000×g for 30 s. The bacteria were resuspended in 100 µl of STET (8% sucrose, 5% Triton X100, 50 mM EDTA, 50 mM Tris pH 8.0). Freshly prepared alkaline SDS (0.2 NaOH, 1% SDS) was added to lyse the bacteria and the solution was incubated at 24° C. for 2 min. Cold ammonium acetate (4° C.) was added and the solution was incubated for 5 min on ice. Following this step, the bacteria were centrifuged at 4° C. for 15 min at 16,000×g. Equal amounts of phenol and chloroform were added to the supernatant to extract the DNA. The top layer of the mixture was treated with 0.6× volume of isopropanol and centrifuged at 4° C. for 15 min at 16,000×g. The supernatant was drained and the pellet washed with 70% ethyl alcohol and air dried. The DNA was resuspended in 100-200 µl of Tris-EDTA (TE) buffer (QIAGEN, Valencia, Calif.) and stored at 4° C.

Fluorescence In Situ Hybridization (FISH). In order to prepare mitotic cells for FISH analyses, HNSCC cells were harvested following 5 h of 0.1 µg/ml Colcemid™ (Irvine Scientific, Santa Ana, Calif.) treatment, hypotonic KCl (0.075M) treatment for 16 min and fixation in 3:1 methanol: glacial acetic acid. All other cells were harvested using the same method, except that 1 h of Colcemid™ was preferred for non-tumor cells. FISH analysis was used to detect copy number changes for the respective genes in the OSCC cell lines. For FISH analysis, cells were harvested, dropped onto slides, treated with RNase/2×SSC, and dehydrated using serial treatments with 70%, 80% and 100% of ethyl alcohol. Chromatin was denatured with 70% formamide and dehydrated in 70%, 80% and 100% of ethyl alcohol. The BAC probes for FISH, described in detail in Appendix A, were obtained from Children's Hospital of Oakland Research Institute (CHORI, San Francisco, Calif.). Using a nick translation kit from Vysis, Inc. (Downers Grove, Ill.), extracted DNA was precipitated with ethyl alcohol, resuspended in hybridization buffer, and allowed to pre-anneal for 1-2 h at 37° C. Each probe was hybridized for 16 h at 37° C., after which slides were washed with SSC/Tween-20. Slides were counterstained with DAPI and mounted with antifade prior to analysis. All FISH analyses were carried out using an Olympus BX-51 epifluorescence microscope (Olympus Microscopes, Melville, N.Y.). An Applied Imaging CytoVision workstation with Genus v3.6 software was used for image capture and analysis (Applied Imaging, San Jose, Calif.).

Paraffin FISH. A 4-5 μM thick slice of paraffin embedded tissue was mounted on a positively charged microscope slide. The slides were aged overnight at 60° C., following which they were deparaffinized with Xylene for 5 min at room temperature. The slides were dehydrated with a series of 70%, 80% and 100% ethyl alcohol washes, each wash lasting 2 min at room temperature. The slides were then treated with 0.5× SKIP Dewax solution at 80° C. for 15 min followed by treatment with pepsin containing protease solution for 15 min at 37° C. After two washes with 2×SSC, each lasting 5 min, the slides were fixed in 10% Formalin for 10 min at room temperature. After 2×SSC washes, the slides were dehydrated with a series of 70%, 80% and 100% ethyl alcohol washes and allowed to dry on slide warmer. The probes for paraffin FISH were prepared as described for regular FISH. The hybridization of the FISH probes and post hybridization treatment of the paraffin slides was carried out as described for regular FISH. Unless specified otherwise, 100 nuclei from tumor tissue and 100 nuclei from normal tissue were analyzed for copy number changes of different genes.

Anaphase Bridge Formation Assay. To check for presence of ATR gene in anaphase bridges, each OSCC cell line was plated in chamber slides and allowed to grow until the cell lines reached 80-90% confluence. 5 ml of Colcemid™ was added to each chamber slide and the slides were incubated at 37° C. in 5% CO2 incubator for a period of 24 h. At the end of 24 h, the media was aspirated and cells were fixed with 3:1 methanol to acetic acid fixative for a period of 45 min. FISH using BAC probe to the ATR gene labeled with Spectrum Green™ CEP3 labeled with Spectrum Orange™ and CEP11 labeled with Spectrum Aqua™ was performed as described above. Fifty anaphase bridges per OSCC or GM09607 were evaluated for the presence of ATR, CEP3 or CEP11.

Clonogenic Cell Survival Assay. To assess cell survival in response to ionizing radiation, clonogenic survival assays were performed. Two thousand cells were seeded in 60 mm Petri dishes and allowed to adhere overnight. Cells were then treated with increasing doses of γ-irradiation at 1, 2.5, 5, and 10 Gy using Gammacell 1000 Elite irradiator (Nordion International, Inc., Ottawa, Canada) with a 137Cs source at a dose rate of 4.42 Gy/min. The culture medium was replaced at the end of 7 days. Untreated cells cultured in parallel were used to determine relative plating efficiency. After 12 days, the cells were fixed with 70% ethyl alcohol and stained with Giemsa (Sigma, St. Louis, Mo.) and the number of colonies was assessed. A colony was defined as a cluster of ≥50 cells, having formed from a single cell. All experiments were performed in triplicate, and the error reported as one standard deviation from the mean.

RNA Extraction and Real-Time PCR. RNA extraction for real time PCR was performed using TRIzol reagent (Invitrogen) according to the manufacturer's instructions. The extracted RNA was purified using the RNeasy Mini kit (QIAGEN) and resuspended in 100 μl RNase free water. The RNA samples were purified of unwanted DNA with the help of DNA-free DNase kit (Ambion, Austin, Tex.) according to the manufacturer's instructions. RNA concentrations were determined using the SmartSpec 3000 (Bio-Rad Laboratories) and normalized to 40 ng/μl. Reverse transcription was carried out with three inputs for each sample: 400 ng of total RNA, 100 ng of total RNA and a negative control with no reverse transcriptase. The RT set up is described in Table 2 below:

TABLE 2

QRT-PCR reagents

| | | Input | | |
|---|---|---|---|---|
| Reagent | Company | 400 ng | 100 ng | No reverse transcriptase |
| 10 × PCR Buffer II | Applied Biosystems | 10 μl | 10 μl | 10 μl |
| MgCl$_2$ (25 Mm) | Applied Biosystems | 30 μl | 30 μl | 30 μl |
| dNTP (25 μM) | Roche Molecular Biochemicals | 4 μl | 4 μl | 4 μl |
| MMLV 10 U/μl | Ambion | 1 μl | 1 μl | 0 μl |
| RNase Inhibitor (40 U/μl) | Applied Biosystems | 1 μl | 1 μl | 1 μl |
| Hex Primer (500 μM) | Applied Biosystems | 2.5 μl | 2.5 μl | 2.5 μl |
| Nuclease free Water | Ambion | 41.5 μl | 49 μl | 42.5 μl |
| RNA (amount) | | 10 μl | 2.5 μl | 10 μl |

The thermocycler conditions were set up as: 25° C. for 10 min, 48° C. for 40 min, 95° C. for 5 min and hold at 10° C. The cDNA was diluted 2.5 times to yield working concentrations of 1.6 ng/μl and 0.4 ng/μl.

For quantitative PCR (qRT-PCR), 5 μM of each primer, 10 μM of probe, 25 mM dNTPs, 25 mM MgCl$_2$, AmpliTaq Gold enzyme (Applied Biosystems) were used. The Taqman primers and probes for ATR, CHEK1 and the control, 18S rRNA were obtained from Applied Biosystems. qRT-PCR was carried out at 95° C. for 10 min followed by 40 cycles of 95° C. for 15 s and 60° C. for 60 s using the 7300 Real-Time PCR System (Applied Biosystems). Each sample was run in triplicate along with the no reverse transcriptase control. For each plate, at least three wells were set up with the master mix but without any cDNA template (no template control). The RNA expression levels were quantified relative to the Universal Reference cDNA obtained from Clontech (Mountain view, Calif.).

Immunoblotting. Immunoblotting was utilized to detect protein expression of MRE11A, ATM and H2AX in HNSCC cell lines, and also to assess the phosphorylation levels of H2AX following exposure to 2.5 Gy IR. Flasks of each cell line were trypsinized, washed with ice cold 1× phosphate-buffered saline (PBS) and lysed on ice with a solution containing 50 mM Tris, 1% Triton X-100 (Sigma), 0.1% sodium dodecyl sulfate (Bio-Rad Laboratories, Hercules, Calif.), 150 mM NaCl (Fisher Chemicals, Fairlawn, N.J.), 1 mM dithiothreitol (DTT) (Fisher Scientific, Inc., Hampton, N.H.), 10 µg/ml leupeptin (Roche Applied Science, Indianapolis, Ind.), 10 µg/ml pepstatin (Roche Applied Science), and 1 nM phenyl methyl sulfonyl fluoride (PMSF) (Santa Cruz Biotechnology, Inc., Santa Cruz, Calif.). The soluble cell lysate was centrifuged at 2000×g for 15 min and transferred to a clean microcentrifuge tube. Histone H2AX was extracted from the remaining pellet containing insoluble protein and chromatin. The pellet was treated with 0.1% HCl for 20 min on ice, and then centrifuged at 10,000×g for 10 min. The supernatant was again transferred to a clean microfuge tube.

Protein concentrations resulting from the standard and acid lysis procedures were determined using the Bio-Rad Quick Start Bradford Protein Assay Kit using a SmartSpec 3000 (Bio-Rad Laboratories). The acid lysate was neutralized with Tris-EDTA (TE) pH 8.0 prior to normalization. Normalized lysates with a protein concentration of 1 µg/µl were resolved by sodium dodecyl sulfate polyacrylamide gel electrophoresis (SDS-PAGE) and transferred onto an Immobilon-P membrane (Millipore Corporation, Billerica, Mass.). After blocking with 5% non-fat dry milk (NFDM) for 1 h, the membrane was incubated overnight with the desired primary antibody (Appendix C) at room temperature. Following three 5 min washes in 1×TBST (Tris-buffered Saline Tween-20), the membrane was incubated with the appropriate secondary antibody (1:3000) for 2 h. Target proteins were visualized using the Western Lighting™ Chemiluminescence Reagent Plus kit (PerkinElmer Life Sciences, Boston, Mass.) according to the manufacturer's instructions.

To verify equal protein loading in the gels, membranes were stripped and re-probed with antibodies against β-tubulin (Santa Cruz), actin (Sigma Immunochemicals, St. Louis, Mo.). Individual antibodies, their concentrations and characteristics are listed in Appendix C.

Cell Cycle Analysis by Flow Cytometry. Following the relevant treatments, mock, IR or aphidicolin, and with or without caffeine or respective siRNAs, floating and adherent cells were collected at the end of 24 h. These cells were washed with phosphate-buffered saline (PBS), and fixed with 70% ethanol. The cells were then treated with 80 µg/ml RNase A and 50 µg/ml propidium iodide (Invitrogen-Molecular Probes, Carlsbad, Calif.) for 45 min at 37° C. The stained cells were analyzed using a Coulter Epics XL Flow Cytometer in the UPCI Flow Cytometry Facility.

Chromosome Breakage Studies. To check for chromosomal damage in OSCC in response to ionizing radiation, the total weighted aberrations per cell were determined for UPCI: SCC084, 104 and 116. Briefly, UPCI:SCC084, 104 and 116 were subjected to 2.5 Gy of IR. The cells were re-seeded and allowed to repair for 48 h prior to being harvested after treatment with 18 nM Calyculin A for 30 min (Calbiochem, San Diego, Calif.). Harvested cells were subjected to a hypotonic treatment before being fixed in Carnoy's fixative. Slides were then prepared from the cell pellets, solid stained for 8 min in 4% Giemsa/PBS solution, and rinsed with distilled water. 50 cells per case (case includes control and IR-treated cells) were scored. Chromosome aberrations documented include: chromosome breaks, chromatid gaps or breaks, radials, giants, rings, minutes, dicentrics, fragments and dots. Chromosome breaks, radials, giants, rings and dicentrics were assigned twice the weight of the other aberrations since they involve two chromatid events. The total weighted aberrations were summed, and determined per chromosome and per cell for each treatment. The standard error of the mean was used as the estimate of error in the sample. A Student's t-test was used to compare the raw distributions of total weighted aberrations between the control and IR-treated samples.

PCC Induction in OSCC. To determine whether inhibition of the ATR-CHEK1 pathway can sensitize OSCC to DNA damaging agents, we treated OSCC cell lines with aphidicolin (Sigma), a DNA polymerase-inhibitor to induce DNA damage, and caffeine (Sigma), a nonspecific kinase inhibitor to inhibit ATR activity. We used AT cell line (GM09607) with a deficient G1 phase checkpoint as our positive control and NHOK cells as negative controls. Briefly 75-80% confluent flasks of cells were pretreated with 1 mM caffeine for 30 min following which 0.4 µM aphidicolin was added. The cell lines were harvested for metaphases 24 h after aphidicolin treatment. A fluorescence microscope was used to count mitotic cells that had characteristic features of either normal mitosis or PCC. Criteria for distinguishing PCC from normal metaphase were adapted from a previous report (NGHEIM et al. 2001). Briefly, interphase cells and cells that with intermediate morphology between normal and PCC were not included in the analysis. Partial metaphases with PCC were also not included in the analysis. The following criteria were used to identify mitoses as PCC or normal: PCC characteristics include well-defined particles by DAPI staining that were round, not oblong, particles with no hazy chromatin material; no chromatid-like pairs present; and borders of the cell's chromatin were irregular and composed of speckles, not smooth or with a hazy appearance (all characteristics must be met). Characteristics of normal mitoses include well-defined chromosomes with a primary constriction; at least 40 such chromosomes should be found in each metaphase spread.

SiRNA Transfection. ATR or CHEK1 inhibitions were carried out using the respective siRNAs for a specific knockout. RNA interference of ATR and CHEK1 was performed using Smartpool ATR and CHEK1 duplexes respectively, obtained from Dharmacon (Lafayette, Colo.). Nonspecific (scrambled) control duplexes (Dharmacon) were used for nonspecific siRNA treatment. The duplexes were reconstituted in 1×DNA-free RNA re-suspension buffer provided by Dharmacon and aliquoted according to the manufacturer's instructions. For transfection, the OSCC cell lines were seeded in 60 mm dishes or T25 flasks and transfected with siRNA duplexes using Lipofectamine 2000 (Invitrogen) according to the manufacturer's instructions. The individual siRNA duplex sequences are enumerated in Appendix B. The final working siRNA concentration achieved was between 90-100 nM. We used cells treated with no vector (untreated), empty vector (mock-treated), cells transfected with a nonspecific siRNA, and a specific ATR or CHEK1 siRNA for all of our experiments. At the end of 48 h post-transfection, appropriate treatments (ionizing radiation or aphidicolin treatment) were carried out as described earlier.

6.2 Results

A Segment of Distal 11q is Partially Lost in a Subset of OSCC. According to the BFB model, the first step in 11q13 amplification is loss of a segment of distal 11q. To determine whether genes located on distal 11q and involved in the DNA damage response are lost in OSCC, we carried out dual-color FISH with BAC probes to MRE11A, ATM, H2AFX and CHEK1 along with a centromere 11 enumeration probe (CEP 11; D11Z1) (Vysis, Downers Grove, Ill.). Table 3 summarizes our FISH results in terms of copy number loss in relation to the ploidy of each cell line, derived from chromosome 11 centromere enumeration and consensus karyotypes. The copy number ratios of the distal 11q genes were normal or lost with respect to CEP 11. The eleven cell lines were grouped based on FISH assessment of 11q13 amplification and distal 11q loss as follows: most cell lines with 11q13 amplification demonstrated partial loss of copies of all four genes, including UPCI:SCC078, 084, 131 and 136 ("11q13 amplified with distal loss"). The OSCC cell lines, UPCI:SCC104, 142 and 122 had loss of one or more genes in the absence of 11q13 amplification ("Distal 11q loss but no 11q13 amplification"). UPCI:SCC099, 116 and 182 did not have 11q13 amplification or distal 11q loss ("no 11q13 amplification, no distal loss"). Interestingly, UPCI:SCC078 and 104 did not demonstrate loss of the CHEK1 gene. UPCI:SCC125 is comprised of a highly heterogeneous cell population, making its analysis less straightforward than the other cell lines. There is no evidence of 11q13 amplification in this cell line. While the copy number ratios seem to show that UPCI:SCC125 is relatively normal in copy number for each of the four distal genes, FISH results indicated that results for MRE11A (31% loss, 44% gain), ATM (52% loss, 1% gain), H2AFX (43% loss, 25% gain) and CHEK1 (45% loss, 30% gain) are more a function of the average than the norm.

TABLE 3

Summary of FISH copy number changes for MRE11A ATM, H2AFX and CHEK1 in OSCC cell lines.

| Cell Line UPCI: | Ploidy | 11q13 amp (+/-) | Distal 11q loss (+/-) | FISH Results | | | |
|---|---|---|---|---|---|---|---|
| | | | | MRE11A[1] | ATM[1] | H2AFX[1] | CHK[1] |
| SCC099 | 2-4 | - | - | 1.00 | 0.98 | 1.02 | 1.00 |
| SCC116 | 3-4 | - | - | 0.96 | 0.97 | 0.96 | 0.94 |
| SCC182 | 3 | - | - | 1.01 | 0.97 | 0.98 | 1.01 |
| SCC078 | 3-4 | + | + | 0.38 | 0.54 | 0.84 | 1.05 |
| SCC084 | 2 | + | + | 0.51 | 0.52 | 0.52 | 0.52 |
| SCC131 | 4 | + | + | 0.56 | 0.59 | 0.53 | 0.44 |
| SCC136 | 4 | + | + | 0.57 | 0.60 | 0.56 | 0.53 |
| SCC104 | 4 | - | + | 0.98 | 0.51 | 0.50 | 0.96 |
| SCC122 | 3 | - | + | 0.69 | 0.68 | 0.71 | 0.71 |
| SCC142 | 3 | - | + | 0.93 | 0.67 | 0.79 | 0.67 |
| SCC125[2] | 3 | - | +/- | 1.08 | 0.79 | 0.97 | 0.93 |

[1]Shading indicates partial loss or haploinsufficiency.
[2]UPCI:SCC125 is a highly heterogeneous cell line with respect to copy number showing comparable number of cells with gain, loss or normal copy number for any given gene.

Confirmation of physical loss on distal 11q was carried out using quantitative microsatellite analysis or QuMA. QuMA was used to map the DNA copy number of segmental microsatellite loci along 11q (FIG. 1). The microsatellites, D11S1358, D11S917 and D11S1893 are the most relevant as they map near the genes of interest on chromosome 11. The results, which demonstrate a loss in copy number of each of these microsatellites confirm the findings of our FISH experiments. A number of the tumor cell lines have near-triploid or near-tetraploid karyotypes, thus DNA copy number of 1 or 2 on the polyploid background reflects a loss of copy number.

LOH analysis was performed as an independent test to validate our FISH and QuMA results. Results were available for nine of the eleven OSCC cell lines studied by FISH and QuMA. The results of LOH analysis, summarized in FIG. 2, substantiate the loss patterns we observed for distal 11q using FISH and QuMA, as extended segments of 11q were shown to have complete or partial LOH in the "distal 11q loss without 11q13 amplification" and "11q13 amplified with distal loss" OSCC cell line groupings. The cell lines with "no 11q13 amplification, no distal loss" do not demonstrate LOH along 11q.

Distal 11q Loss Results in Chances in Expression of MRE11A, ATM, H2AX and CHEK1. Taqman quantitative reverse transcriptase PCR (qRT-PCR) and immunoblotting were performed to assess whether loss of one or more copies of the MRE11A, ATM, H2AFX and CHEK1 genes translates into a reduction in their expression (FIG. 3). UP3_344, 348 and 700 were the NHOK controls used for the study. Overall, we observed that cell lines with distal 11q loss generally exhibit a reduction on ATM and H2AFX expression relative to control NHOK cell line and cell lines with no distal 11q loss.

Protein expression in OSCC cell lines and various controls was assessed by immunoblotting (FIG. 4). Cell lines with distal 11q loss tend to have an overall lower expression level of the MRE11A, ATM and H2AX proteins compared to those without distal 11q loss. Further, the relative trends in protein expression correlated with the quantitative RT-PCR analysis. Thus, a genetic loss of distal 11q leads to reduction on the RNA and protein expression for ATM, MRE11A and H2AX in a subset of OSCC.

Distal 11q Loss is Associated with Aberrant γ-H2AX Focus Formation. Using phosphorylation of H2AX as a surrogate marker for a proficient DNA damage response, Dr. Jason White evaluated the competency of OSCC cell lines to detect double strand breaks and initiate repair by formation of γ-H2AX foci after treatment with 2.5 Gy IR. Constitutive phosphorylation patterns were observed in some of the cell lines (UPCI:SCC099 and 116) in the absence of any apparent overt or exogenous genetic insult. Hence, deficiencies in focus formation were assayed by several measurements, including the mean number of foci per cell, the distribution of foci in 200 cells, and the percent of focus-positive cells. Fewer focus-positive cells, coupled with a reduced mean number of foci per cell relative to control, are indicative of a deficient DNA damage response. The distribution of foci also shows a deficient response when the distribution is skewed toward fewer signals as shown in FIG. 5A-B. The highest mean numbers of foci were seen in the cells with "no 11q13 amplification, no distal loss" (min=5.40; max=9.45), and these were similar to those of the control fibroblast cell line. The cell lines that are "11q13 amplified with distal loss" showed the lowest mean levels of H2AX foci. When treated with IR, the mean number of foci was more than two-fold lower than cell lines without 11q alteration (min=3.02; max=4.64). Cell lines with "distal 11q loss without 11q13 amplification" showed low to intermediate levels of γ-H2AX focus formation after IR (min=3.09; max=6.83). While there was focus formation in the untreated AT cell line (GM09607), there was essentially no difference between the untreated and treated cells one hour following treatment, showing that the cells do not respond normally to IR.

Distal 11q Loss is Associated with Chromosomal Instability. The total number of weighted aberrations per chromosome were determined for UPCI:SCC084, 104 and 116. Examples of metaphase spreads from each of these cell lines are shown in FIG. 9. Breakage was assessed 48 h post-IR, and breaks were evident in the cell lines with loss of distal 11q, irrespective of 11q13 status. Complete results are summarized in Table 4. We determined the 95% confidence intervals for each of the cell lines evaluated for IR-induced breakage. There was no significant difference in the total number of weighted aberrations per cell between the control (2.52±0.97%) and treated (2.94±0.62%) populations of UPCI:SCC116, which represents the "no 11q13 amplification, no distal loss" group. There is substantial agreement in the results for UPCI:SCC084 (C=1.43±0.51%; IR=6.68±1.40%; p<0.001) and UPCI:SCC104 (C=3.15±0.76%; IR=6.68±1.05%, p<0.001), both of which have distal 11q loss. An insignificant increase in chromosomal breaks in UPCI:SCC116 in response to ionizing radiation could be caused due to a highly efficient DNA damage repair pathway or may be as a result of cells with increased breaks undergoing apoptosis. Thus, UPCI:SCC084 (11q13 amplified with distal loss) and UPCI:SCC104 (distal 11q loss without 11q13 amplification) demonstrated elevated levels of chromosomal aberrations in response to ionizing radiation when compared to UPCI:SCC116 (no 11q13 amplification, no distal loss).

TABLE 4

Summary of chromosomal aberrations in OSCC in response to IR.

| Cell Line UPCI: | 11q13 Amp | Distal 11q Loss | Treatment | Total Weighted Aberrations per Chromosome ± 95% CI | Total Weighted Aberrations per Cell ± 95% CI |
|---|---|---|---|---|---|
| SCC116 | - | - | Control | 0.05 ± 0.02 | 2.52 ± 0.97 |
|  |  |  | 2.5 Gy IR | 0.06 ± 0.01 | 2.94 ± 0.62 |
| SCC084 | + | + | Control | 0.03 ± 0.01 | 1.43 ± 0.51 |
|  |  |  | 2.5 Gy IR | 0.15 ± 0.03 | 6.68 ± 1.40 |
| SCC104 | - | + | Control | 0.07 ± 0.02 | 3.15 ± 0.76 |
|  |  |  | 2.5 Gy IR | 0.15 ± 0.02 | 6.68 ± 1.05 |

Shaded areas indicate statistically significant results with 'p' value <0.001.

The frequency of anaphase bridges in five hundred cells was determined and used an indicator of baseline chromosomal instability in OSCC. The frequencies of anaphase bridges in each cell line are summarized as percentages in Table 4. Overall, the lowest frequency was seen in normal male lymphocytes (0.7%). The lowest frequency among all OSCC cell lines was seen in UPCI:SCC116 (0.96%), and the highest frequency was seen in UPCI:SCC142 (5.63%). In cell lines with no 11q13 amplification and no distal loss, the maximum frequency (1.31%; UPCI:SCC099) was lower than any of the frequencies observed in the "11q13 amplified with distal loss" and "distal 11q loss without 11q13 amplification" groups. In a comparison of proportions, most cell lines with distal 11q loss, irrespective of 11q13 amplification, have significantly elevated levels of anaphase bridges (p<0.05). The comparison was made relative to normal male lymphocytes. For two of the cell lines, UPCI:SCC078 and 122, the p-value is less than 0.1. Since all anaphase bridge frequencies were measured in untreated cell populations, the intrinsic level of chromosomal instability appears to be higher in cell lines with 11q loss.

TABLE 5

Baseline anaphase bridge formation in OSCC.

| Cell Line | 11q13 Amplification | Distal 11q Loss | Anaphase bridge frequency |
|---|---|---|---|
| SCC099 | - | - | 0.96 |
| SCC116 | - | - | 1.27 |
| SCC182 | - | - | 1.31 |
| SCC078 | + | + | 1.86 |
| SCC084 | + | + | 2.65 |
| SCC131 | + | + | 3.08 |
| SCC136 | + | + | 3.58 |
| SCC104 | - | + | 4.14 |
| SCC122 | - | + | 1.87 |
| SCC142 | - | + | 5.63 |
| SCC125 | - | + | 3.1 |

Anaphase bridge formation was determined in eleven OSCC by Dr. Jason White. All OSCC cell lines with significantly high (p value <0.05) anaphase bridge formation at rest are highlighted in grey.

Distal 11q Loss is Associated with Radioresistance. Clonogenic survival assays were used to detect sensitivity of OSCC to survival after DNA damage induced by ionizing radiation (FIG. 6 and Table 6). Results for the assay in triplicate, were grouped as "no 11q13 amplification, no distal loss" (UPCI:SCC099, 116 and 182), "11q13 amplified with distal loss" (UPCI:SCC078, 084, 131 and 136), and "distal 11q loss without 11q13 amplification" (UPCI:SCC104, 122 and 142). Also included were normal human oral keratinocyte (NHOK) cells as normal controls and UPCI:SCC125 (separated due to its heterogeneity in copy number by FISH). In the grouped analysis, nearly 60% of NHOKs survived a single unfractionated dose of 1 Gy, and none survived a dose of 10 Gy. Similarly, the OSCC cells with "no 11q13 amplification, no distal loss" showed 56% survival at 1 Gy, and no survival at 10 Gy IR. Conversely, the OSCC cell lines grouped as "11q13 amplified with distal loss" had nearly 83% survival at 1 Gy, and 9% survival at 10 Gy IR. The "distal 11q loss without 11q13 amplification" cells had 80% survival at 1 Gy and 7% survival after exposure to 10 Gy IR. The UPCI:SCC125 cells had a high surviving fraction after 1 Gy (83.3±5.0%), and a small, but visible surviving fraction at 10 Gy (0.7±0.6%). Thus, cell lines with 11q13 amplification and distal 11q loss (UPCI:SCC078, 084, 131 and 136) and cell lines with distal 11q loss without 11q13 amplification (UPCI:SCC104, 122 and 142) demonstrate similar resistance to ionizing radiation. In contrast, normal human oral keratinocytes (NHOK) and cell lines without distal 11q loss are sensitive to ionizing radiation.

TABLE 6

Results of clonogenic cell survival in OSCC in response to ionizing radiation.

| Cell line | 11q13 Amp | Distal 11q loss | Mock treated | 1 Gy | 2.5 Gy | 5 Gy | 10 Gy |
|---|---|---|---|---|---|---|---|
| NHOK | - | - | 100 ± 0.0 | 59.7 ± 2.1 | 30.3 ± 0.6 | 6.7 ± 0.6 | 0.0 ± 0.0 |
| SCC099 | - | - | 100 ± 0.0 | 58.0 ± 1.0 | 29.7 ± 1.5 | 5.7 ± 1.2 | 0.0 ± 0.0 |
| SCC116 | - | - | 100 ± 0.0 | 55.0 ± 4.4 | 23.0 ± 2.6 | 6.0 ± 1.0 | 0.0 ± 0.0 |
| SCC182 | - | - | 100 ± 0.0 | 56.0 ± 5.2 | 32.7 ± 4.0 | 9.3 ± 2.1 | 0.0 ± 0.0 |
| SCC104 | - | + | 100 ± 0.0 | 82.3 ± 4.7 | 55.3 ± 2.1 | 33.7 ± 1.2 | 7.7 ± 0.6 |

TABLE 6-continued

Results of clonogenic cell survival in OSCC in response to ionizing radiation.

| Cell line | 11q13 Amp | Distal 11q loss | Mock treated | 1 Gy | 2.5 Gy | 5 Gy | 10 Gy |
|---|---|---|---|---|---|---|---|
| SCC122 | − | + | 100 ± 0.0 | 77.0 ± 1.0 | 54.7 ± 0.6 | 24.0 ± 1.7 | 4.0 ± 1.0 |
| SCC142 | − | + | 100 ± 0.0 | 81.0 ± 4.0 | 51.7 ± 4.6 | 35.3 ± 1.5 | 9.7 ± 0.6 |
| SCC078 | + | + | 100 ± 0.0 | 83.0 ± 2.6 | 56.7 ± 0.6 | 38.0 ± 1.7 | 7.0 ± 0.0 |
| SCC084 | + | + | 100 ± 0.0 | 80.7 ± 4.6 | 52.3 ± 5.0 | 24.7 ± 2.1 | 7.7 ± 0.6 |
| SCC131 | + | + | 100 ± 0.0 | 86.7 ± 2.5 | 51.7 ± 3.8 | 37.3 ± 2.1 | 11.3 ± 2.5 |
| SCC136 | + | + | 100 ± 0.0 | 81.7 ± 3.5 | 55.0 ± 4.6 | 34.7 ± 2.5 | 11.0 ± 1.0 |
| SCC125 | − | + | 100 ± 0.0 | 83.3 ± 5.0 | 40.3 ± 3.2 | 27.7 ± 0.6 | 0.7 ± 0.6 |

FIG. 7A-D presents a summary of the results for distal 11q loss and its effects in representative OSCC.

Loss of the G1 Checkpoint in a Subset of OSCC. OSCC were treated with ionizing radiation and performed flow cytometry in order to study the cell cycle profiles of OSCC in response to DNA damaging agents. The cell cycle profiles of different cell lines to IR are summarized in Table 7. FIG. 8 demonstrates the cell cycle profiles of two cell lines, UPCI: SCC066 and 104 in response to 5 Gy IR. We observed that even in untreated cells, UPCI:SCC104 has a considerably high percentage of cells in the S and G2M phases. Following IR, SCC066 shows accumulation of cells in both the G1 and G2M phases while, UPCI:SCC104 shows a predominant accumulation of cells in the S and G2M phases. Thus, UPCI: SCC104 demonstrates a loss of G1 phase cell cycle checkpoint in response to IR.

function. Carcinomas with loss of the G1 checkpoint express loss of p53 protein expression and ATR/CHEK1 overexpression at the RNA and protein levels p53 activity and/or expression varies among cancer cell lines. FIGS. 32A and B show respectively, the expression of these proteins in oral squamous carcinoma and non-small cell lung carcinoma and ovarian carcinoma cell lines, respectively. Active p53 results in induction of p21 expression. The extent of radiosensitivity of cancer cells expressing active p53 (for example, A549 (FIG. 32B), which shows induction of p21) was observed to be somewhat greater than that of cells that did not contain active p53 (for example, ES-2 (FIG. 32B) and UPCI:SCC040); compare the results shown in FIG. 34 (active p53) with FIGS. 33 and 35 (no active p53). As shown in FIG. 35, cells lacking active p53, although somewhat less sensitive to radiation, responded dramatically to a combina-

TABLE 7

Results of cell cycle analysis in OSCC in response to ionizing radiation.

| | Untreated | | | | 5 Gy IR (24 h) | | | |
|---|---|---|---|---|---|---|---|---|
| UPCI: Cell Line | Sub $G_0$ | $G_1$ | S | $G_2M$ | Sub $G_0$ | $G_1$ | S | $G_2M$ |
| NHOK | 0.1% | 71% | 13% | 15.9% | 3% | 75% | 2% | 20% |
| GM09607 | 2% | 52.2% | 6.8% | 39% | 6% | 34% | 8.9% | 51.1% |
| SCC066 | 1.2% | 70% | 13.3% | 15.5% | 1.9% | 50.3% | 16.1% | 31.7% |
| SCC084 | 0.7% | 60% | 10% | 29..3% | 2.4% | 32% | 12% | 53.6% |
| SCC104 | 0.9% | 53% | 16% | 30.1% | 2.8% | 22% | 18% | 57.2% |
| SCC105 | 0.7% | 67% | 13% | 19.3% | 4% | 51% | 15% | 30% |
| SCC116 | 1.1% | 61.9% | 15% | 22% | 4% | 49% | 15% | 32% |
| SCC131 | 1% | 66.5% | 15.5% | 15% | 2.5% | 32% | 11% | 55.5% |
| SCC136 | 1% | 59.9% | 10% | 29.1% | 1.9% | 31.6 | 25.5 | 41% |
| SCC142 | 1.3% | 62.2% | 14.2% | 22.3% | 2.6% | 31% | 16% | 40.4% |

Thus a loss of G1 checkpoint was observed in response to IR in 5 out of 8 OSCC studied. Even UPCI:SCC066, 105 and 116 with an intact G1 checkpoint, had an increased accumulation of cells in the G2M phase compared to NHOK. This may be either due to higher number of cells in the G2M checkpoint at the time of DNA damage or due to cell line/tumor heterogeneity wherein a fraction of cells in UPCI:SCC066, 105 and 116 lack p53 and are deficient in their G1 checkpoint. A loss of G1 checkpoint in OSCC leads to increased number of cells with unrepaired DNA damage entering the S and the G2M phases of the cell cycle. Thus, OSCC with an enhanced S and G2M phase cell cycle checkpoints are able to avoid p53-independent cell death (PCC/MC) and have a growth advantage.

p53 and ATR Expression. It was observed that loss of p53 protein expression is associated with overexpression of ATR in a larger panel of OSCC cell lines (FIG. 9). Thus, it is possible that either loss of p53 leads to ATR upregulation, or overexpressed ATR in OSCC may affect p53 regulation and tion of irradiation and inhibition of CHEK1 by CHEK1 siRNA, cell survival being drastically reduced Copy Number and Structural Changes Involving the ATR and CHEK1 Genes.

To determine if there are structural or numerical changes in the ATR and CHEK1 genes in OSCC, dual-color FISH with BAC probes to ATR was performed along with a centromere 3 enumeration probe (CEP 3) and BAC probes to CHEK1 and compared it to centromere 11 enumeration probe (CEP 11; D11Z1) (Vysis, Downers Grove, Ill.). Table 8 summarizes the FISH results in terms of copy number gain in relation to the ploidy of each cell line, which was derived from chromosome 3 centromere enumeration and consensus karyotypes. Copy number gains were observed in the ATR gene in all cell lines with distal 11q loss. In addition, it was observed that in a number of cell lines depicted in FIG. 10A-F and Table 8 that copy number gains were associated with isochromosome 3q formation. In UPCI:SCC084, copy number gain in the ATR gene was not observed. However, by metaphase FISH, a translocation of one copy of the ATR gene was detected. On further evaluation of UPCI:SCC084, the ATR gene was translocated to a derivative chromosome 11 with 11q13 amplification. In addition to OSCC, low level amplification (8-10 copies per cell) was observed in an ovarian tumor cell line, Ovcar-3. It was observed that CHEK1 was partially lost in all OSCC cell lines with 11q13 amplification. Loss of CHEK1 was also seen in UPCI:SCC122 and 142 which did not demonstrate 11q13 amplification. Of the twenty OSCC cell lines studied, ATR gain was observed in ten OSCC and CHEK1 loss in fifteen OSCC suggesting that both these events occur frequently in OSCC.

Five primary squamous cell carcinomas of the oral cavity were tested for ATR and CHEK1 copy number alterations (Table 9, FIG. 11A-F). A gain in copy number for the ATR gene was detected in the tumor tissue in all five tumors while the surrounding normal tissue exhibited normal copy number for the ATR gene and CEP 3. Similarly, CHEK1 was partially lost in 35% to 65% of cells in the tumor tissue, while the adjacent normal tissue showed no loss of the gene. High level CCND1 amplification was found in 65% to 100% of the tumor cells suggesting that 11q13 amplification may be an early change. Thus, ATR gain and CHEK1 loss are present not only in OSCC cell lines but also in the head and neck primary tumors.

TABLE 8

Results of FISH analysis for the ATR and CHEK1 genes.

| Cell line | 11q13 Amp | ATM loss | ATR % cells with gain | ATR % cells with loss | ATR % cells with no change | ATR:CEP3 ratio | Iso 3q | CHEK1 % cells with gain | CHEK1 % cells with loss | CHEK1 % cells with no change | CHEK1:CEP11 ratio |
|---|---|---|---|---|---|---|---|---|---|---|---|
| Normal | | | — | — | 100% | 1.0 | — | — | — | 100% | 1.0 |
| SCC003 | + | + | 53% | 1% | 46% | 1.6 | — | 1% | 93% | 6% | 0.71 |
| SCC029B | + | + | 89% | 2% | 9% | 1.4 | — | — | 99% | 1% | 0.61 |
| SCC032 | + | + | 57% | — | 43% | 1.3 | — | 1% | 99% | — | 0.67 |
| SCC040 | + | + | 53% | — | 47% | 1.6 | — | 5% | 94% | 1% | 0.56 |
| SCC066 | − | − | 2% | 3% | 95% | 1.0 | — | 1% | 1% | 98% | 1.01 |
| SCC070 | + | + | 89% | 1% | 10% | 2.1 | + | — | 98% | 2% | 0.57 |
| SCC077 | + | + | 85% | 1% | 14% | 2.2 | + | 2% | 31% | 67% | 0.67 |
| SCC078 | + | + | 9% | 3% | 88% | 1.0 | — | — | 94% | 6% | 1.05 |
| SCC084 | + | + | 7% | — | 93% | 1.0 | — | 2% | 98% | — | 0.52 |
| SCC099 | − | − | 3% | 6% | 91% | 1.0 | — | — | 100% | — | 1.0 |
| SCC103 | + | + | 91% | 1% | 8% | 1.1 | — | 2% | 94% | 4% | 0.74 |
| SCC104 | + | + | 98% | — | 2% | 2.2 | + | 1% | 11% | 88% | 0.97 |
| SCC105 | − | + | 2.5% | 0.5% | 97% | 1.1 | — | 12% | 32% | 56% | 0.85 |
| SCC116 | − | − | 3% | 2% | 95% | 1.0 | — | 3% | 10% | 87% | 0.94 |
| SCC122 | − | + | 1% | 9% | 90% | 1.0 | — | 1% | 82% | 17% | 0.71 |
| SCC131 | + | + | 92.5% | — | 7.5% | 2.1 | + | — | 98% | 2% | 0.44 |
| SCC136 | + | + | 78.5% | — | 21.5% | 1.3 | — | — | 96% | 4% | 0.53 |
| SCC142 | − | + | 98.5% | — | 1.5% | 2.1 | + | — | 91% | 9% | 0.67 |
| SCC172 | + | + | 3% | 5% | 92% | 1.1 | — | 5% | 90% | 5% | 0.71 |
| SCC182 | − | − | 1% | 1% | 98% | 1.0 | — | 3% | — | 97% | 1.01 |
| MDA231 | | | 6% | 4% | 90% | 1.0 | — | 5% | 1% | 94% | 1.1 |
| MCF7 | | | — | 1% | 99% | 1.0 | — | — | 3% | 97% | 1.0 |
| SK-OV3 | | | 4% | 3% | 93% | 1.1 | — | 1% | — | 99% | 1.0 |
| OVCAR3 | | | 99% | — | 1% | 9 | — | 8% | — | 92% | 1.1 |

TABLE 9

ATR, CHEK1 and CCND1 FISH in primary head and neck tumors.
'T' represents the head and neck primary tumor and 'N' represents surrounding normal tissue.
Figures in each column represent % cells with gain, % cells with loss or % cells with no change.

| Sample I D: | | ATR Amp/Gain | ATR Normal | ATR Loss | CHEK1 Amp/Gain | CHEK1 Normal | CHEK1 Loss | CCND1 Amp/Gain | CCND1 Normal | CCND1 Loss |
|---|---|---|---|---|---|---|---|---|---|---|
| 0402584 | N | 2% | 98% | — | — | 99% | 1% | 2% | 98% | — |
| | T | 54% | 46% | — | — | 35% | 65% | 100% | — | — |
| 3L621340 | N | 1% | 99% | — | — | 98% | 2% | 1% | 99% | — |
| | T | 58% | 42% | — | — | 65% | 35% | 99% | 1% | — |
| 1H620781 | N | 2% | 98% | — | — | 98% | 2% | 3% | 94% | 3% |
| | T | 32% | 66% | 2% | — | 51% | 49% | 65% | 34% | 1% |
| 3G040281 | N | 1% | 98% | 1% | 1% | 98% | 1% | — | 100% | — |
| | T | 42% | 58% | — | — | 44% | 56% | 100% | — | — |
| 1F620600 | N | — | 98% | 2% | — | 99% | 1% | 3% | 95% | 2% |
| | T | 42% | 57% | 1% | — | 37% | 63% | 68% | 32% | — |

Mechanism of ATR Gain and ATR Translocations. It has been previously reported that in OSCC, translocations of chromosome 3 are commonly associated with 11q13 amplification and frequently, chromosome 3 fragments cap the amplified chromosome 11. It was observed that three of 20 OSCC cell lines studied (UPCI:SCC078, 084 and 172) had a translocation between the derivative chromosome 11 der(11) with 11q13 amplification and segments of 3q along with the ATR gene (FIG. 12A, B). Similar translocations between chromosome 3 and der(11) with 11q13 amplification in OSCC were also reported by another group, suggesting that this event may be common in head and neck tumors (JIN et al. 2002). In all three OSCC cell lines, UPCI:SCC078, 084 and 172, this t(3;11) translocation was present in all twenty metaphases studied.

Isochromosome 3q formation was found in five of 20 OSCC cell lines (UPCI: SCC070, 077, 104, 131 and 142) studied. Isochromosome 3q formation is a common mechanism of 3q and ATR gain in OSCC. Isochromosome formation can occur either through centromere splitting or by fusion of two chromosome 3 with breaks at 3p resulting in an iso-dicentric chromosome 3. Isodicentric chromosomes 3q was observed in SCC070, 077, 104, 131 and 142, suggesting that centromere splitting is not the mechanism by which isochromosome formation occurs in OSCC (FIG. 12, C).

Dicentric chromosomes are prone to being pulled to opposite centromeres during cell division resulting in an anaphase bridge between the two daughter cells. The formation of a dicentric chromosome 11 is also an intermediate in the process of 11q13 amplification and its presence in anaphase bridges may indicate a stage of ongoing amplification and chromosomal instability. The frequency of ATR gene and CEP 3 presence was observed in anaphase bridges and compared it to the presence of CEP 11 in anaphase bridges in a subset of four OSCC cell lines and GM09607 (AT cell line). The results for 50 anaphase bridges analyzed for each cell line are summarized in Table 10 (see also FIG. 13A-B). An increased frequency of ATR gene was observed in anaphase bridges in UPCI:SCC104 and 131, both of which have gain for chromosome 3, but not in UPCI:SCC066 and 105 which have normal copy numbers for the ATR gene. Surprisingly, an increase in the frequency of ATR gene present was detected in anaphase bridges in GM09607, which does not have 3q and ATR gain. Since GM09607 relies heavily on the upregulated ATR-CHEK1 pathway for survival, anaphase bridges may serve as a mechanism for formation of isodicenteric 3q leading to ATR and 3q gain. Thus, the high frequency of ATR and CEP3 in anaphase bridges may represent ongoing selection for 3q gain. On the other hand, chromosome 3, on account of its large size may be prone to be present in anaphase bridges at an increased frequency.

TABLE 10

Frequency of ATR, CEP 3 and CEP11 in anaphase bridges in OSCC and GM09607.

| Cell Line | 11q13 amplification | ATR gain | Frequency of ATR in bridges | Frequency of CEP3 in bridges | Frequency of CEP11 in bridges |
|---|---|---|---|---|---|
| SCC066 | − | − | 4% | 4% | 6% |
| SCC104 | − | + | 26% | 26% | 14% |
| SCC105 | − | − | 6% | 6% | 22% |
| SCC131 | + | + | 28% | 28% | 24% |
| GM09607 | − | − | 16% | 16% | 10% |

ATR and CHEK1 are Overexpressed in a Subset of OSCC. To evaluate if changes in copy number for ATR and CHEK1 genes in OSCC lead to changes in expression, ATR and CHEK1 RNA expression was studied using qRT-PCR and protein expression by immunoblotting. Our qRT-PCR results are summarized in FIG. 14A-C. Since the RNA expression was measured relative to universal reference with diploid chromosomal constitution, a relative expression <1.5 in OSCC (with near-triploid to tetraploid karyotypes) can be considered as a reduction in relative RNA expression.

RNA expression was evaluated by qRT-PCR in eleven OSCC cell lines, GM09607 (AT cell line). NHOK and HEK 293 cells were used as control cell lines. UPCI:SCC066, 099, 105 and 122 showed ATR and CHEK1 expression equal to or lower than the NHOK and HEK293 control cell lines. GM09607 which has been shown to have an upregulated ATR-CHEK1 pathway demonstrated 4-fold increase in ATR expression and 8-fold increase in CHEK1 expression. Six out of eleven cell lines including UPCI:SCC040, 104, 131, 136, 142 and 172 demonstrated an increase in both ATR and CHEK1 expression. Around 8-fold increase in ATR expression and 18-20 fold increase in CHEK1 expression were observed in two OSCC cell lines: UPCI:SCC040 and 104. It should be noted that all cell lines with ATM loss (UPCI:SCC 104, 131, 136 and 142) other than UPCI:SCC122 demonstrated a significant increase in ATR and CHEK1 RNA expression.

Immunoblotting for ATR and CHEK1 proteins shown in FIG. 15 confirmed the qRT-PCR results. An increase in the expression for ATR was found in all the cell lines with copy number gain for the ATR gene. Though UPCI:SCC084, the cell line with the highest basal expression of ATR did not have any gain of the ATR gene, it had a translocation of one of its copies of the ATR gene which may account for the increased expression.

Earlier reports suggested that kinase-dead ATR can inhibit serine15-p53 phosphorylation in response to DNA damage and thus, block p53 activation in response to IR and UV radiation (TIBBETTS et al. 1999). To check whether the overexpressed ATR in UPCI:SCC084 and 104 was kinase-dead, CHEK1 phosphorylation on serine-345 was assayed following treatment with IR and ultra-violet radiation (UV). Since CHEK1 s345 phosphorylation following UV radiation is preferentially mediated through ATR kinase, it appears that ATR kinase activity is not lost in any of the four cell lines studied (FIG. 16A-C). On studying ATR mediated phosphorylation of SMC1 on serine 957, in response to 20 J/m2 UV radiation, UPCI:SCC084 and 104 were found to have much higher levels of SMC1 phosphorylation. Since SMC 1 phosphorylation occurs during the S and G2M phases, these results confirm findings that the G1 is compromised in SCC084 and 104. Increased phosphorylation of Cdc25C on serine-216 was observed in response to 5 Gy IR in UPCI:SCC104 compared to SCC066. These observations suggest that an overactive ATR-CHEK1 response is present in UPCI:SCC084 and 104 and that a higher number of cells with DNA damage enter the S and G2M phases in response to DNA damage.

An Upregulated ATR-CHEK1 Pathway is Associated with Radioresistance.

It was observed that all cell lines with an upregulated ATR-CHEK1 pathway demonstrate increased resistance to ionizing resistance (Table 11). Since loss of p53 was also observed in these cell lines, the resistance to ionizing radiation could be as a result of loss of p53-mediated apoptotic pathways and an upregulated ATR-CHEK1 pathway which promotes G2M accumulation and HRR after DNA damage.

TABLE 11

Clonogenic cell survival of OSCC to different doses of IR

| Cell line | ATR, CHEK1 overexpression | Mock treated | 1Gy | 2.5Gy | 5Gy | 10Gy |
|---|---|---|---|---|---|---|
| NHOK | − | 100 ± 0.0 | 59.7 ± 2.1 | 30.3 ± 0.6 | 6.7 ± 0.6 | 0.0 ± 0.0 |
| SCC084 | + | 100 ± 0.0 | 80.7 ± 4.6 | 52.3 ± 5.0 | 24.7 ± 2.1 | 7.7 ± 0.6 |
| SCC104 | + | 100 ± 0.0 | 82.3 ± 4.7 | 55.3 ± 2.1 | 33.7 ± 1.2 | 7.7 ± 0.6 |
| SCC142 | + | 100 ± 0.0 | 81.0 ± 4.0 | 51.7 ± 4.6 | 35.3 ± 1.5 | 9.7 ± 0.6 |
| SCC131 | + | 100 ± 0.0 | 86.7 ± 2.5 | 51.7 ± 3.8 | 37.3 ± 2.1 | 11.3 ± 2.5 |
| SCC136 | + | 100 ± 0.0 | 81.7 ± 3.5 | 55.0 ± 4.6 | 34.7 ± 2.5 | 11.0 ± 1.0 |
| SCC066 | − | 100 ± 0.0 | 56.7 ± 1.1 | 29.5 ± 2.2 | 5.5 ± 1.0 | 0.0 ± 0.0 |
| SCC105 | − | 100 ± 0.0 | 60.1 ± 2.1 | 32.3 ± 1.5 | 7.9 ± 2.6 | 0.0 ± 0.0 |

Caffeine a Non-Specific Kinase Inhibitor Sensitizes OSCC to IR Induced DNA Damage. In order to study the relative contribution of ATR and CHEK1 overexpression to the radioresistance observed in a subset of OSCC, we determined the sensitivity of OSCC to caffeine which is a non-specific inhibitor of ATM and ATR. OSCC were treated with caffeine in combination with DNA damaging agents (IR or aphidicolin). The following tests were performed to estimate the sensitivity of OSCC to caffeine: the sub-G0 population in flow cytometeric studies, the surviving fraction using clonogenic cell survival assay and PCC/MC formation in response to caffeine.

A prolonged S phase and G2M accumulation were observed in a subset of irradiated OSCC cells which suggests that the S and G2M checkpoint are enhanced in IR treated OSCC. One possible explanation for this observation would be that the G2M accumulation in irradiated OSCC was mediated through the ATR-CHEK1 pathway, as seen in irradiated AT cells (WANG et al. 2004). OSCC was treated with caffeine, a non-specific inhibitor of ATM and ATR kinases and evaluated their cell cycle profiles following irradiation (FIG. 17). It was found that caffeine clearly reduced accumulation of cells in the S and G2M phases and increased the sub-G0 population (dead cells) in cells lines with an upregulated ATR-CHEK1 pathway including GM09607 (AT cells). In comparison, cell lines with an intact G1 checkpoint and normal ATR-CHEK1 expression did not demonstrate any sensitivity to caffeine.

To detect the mechanism of caffeine-induced cell death, 'S' phase PCC and MC formation was evaluated in response to only aphidicolin (0.4 µM), or in cells pretreated with 1 mM caffeine 1 h before aphidicolin treatment (FIG. 18A-C). Criteria for distinguishing PCC/MC from normal metaphase were adapted from a previous report (NGHEIM et al. 2001). A very high percentage of mitotic cells with PCC/MC in UPCI:SCC084 and 104 were observed if pretreated with 1 mM caffeine (FIG. 18A). This high percentage was comparable with GM0607 (AT cells), which was used as a positive control. In comparison, UPCI:SCC066 and 105 with an intact G1 checkpoint demonstrate low levels of PCC/MC formation even after caffeine pretreatment. The morphology of PCC/MC is depicted in FIG. 18B. Thus, caffeine mediated elimination of the G2M peak is caused due to increased death (by PCC/MC) of these cells by entering premature S phase or premature mitosis.

It was found that cell lines with upregulated ATR-CHEK1 pathway had prolonged G2M accumulation following irradiation and a reduced sensitivity to IR-induced cell death. However, the exact mechanism of how an enhanced G2M checkpoint can promote radioresistance is not known. It is likely that prolonged G2M accumulation may allow adequate time for repair and thus promote cell survival. Since caffeine eliminates the G2M accumulation observed in OSCC, the sensitivity of OSCC to different doses of caffeine was studied by clonogenic cell survival. It was observed that caffeine enhances cell sensitivity to ionizing radiation, especially in OSCC with upregulated ATR-CHEK1 pathway (FIGS. 19, 20). UPCI:SCC084 and 104 showed a significant (>50%) reduction in colony survival at a dose of 0.5 mM caffeine and complete absence of survival at 1 mM caffeine. Thus, OSCC with an upregulated ATR-CHEK1 pathway (UPCI:SCC084 and 104) exhibit increased sensitivity to caffeine in the absence of any DNA damaging agents.

ATR and CHEK1 siRNA Sensitize a Subset of OSCC to Ionizing Radiation and Aphidicolin Induced DNA Damage. Small inhibitory RNA (siRNA) are composed of 21-25 nucleotides which are complimentary to a known 'target' mRNA (ELBASHIR et al. 2001). Usually a pool of two or more siRNA duplexes is used to specifically bind to and degrade the 'target' mRNA. Usually peak siRNA transfection is seen at the end of 48-72 hrs and the mRNA knockout lasts for 1-3 weeks depending on the type and stability of the siRNAs. Recently, there is growing interest to use siRNA mediated gene targeting to inhibit specific genes involved in cancer and other diseases (WALL and SHI 2003).

In the following experiments, siRNA specific to ATR and CHEK1 was used to reduce their expression in UPCI:SCC066 and 104. Transfection efficiency was calculated using a non specific siRNA labeled with a fluorescent tagged siGLO (Dharmacon). Reduction in ATR and CHEK1 expression was determined by checking protein levels by immunoblotting at the end of 72 h. The results of these experiments were a high level of ATR and CHEK1 knockout by their specific siRNAs while a scrambled non-specific siRNA did not inhibit ATR and CHEK1 protein expression (FIG. 21).

The cell cycle profiles of UPCI:SCC066 and 104 were analyzed after ATR and CHEK1 knockout using the respective siRNAs (FIG. 22A-B). Even in the untreated sample, there were a very high number of cells in the S (18%) and G2M (29%) phases in SCC104. Following treatment with 5 Gy IR, at the end of 24 h, a very high percentage of cells (nearly 55%) accumulated in the G2M phase in SCC104 compared to 31% in SCC066. Following treatment with ATR siRNA, in irradiated SCC104, there was a significant reduction in the G2M accumulation of cells from 55% to 18% and an increase in the sub-G0 population (dead cells) from 1% to nearly 18%. Since a corresponding increase occurred in the sub-G0 population, the reduction of the G2M peak observed in SCC104 appears to be due to cell death and not due to a reduction in the number of cells that enter G2M. Even in un-irradiated SCC104 cells, there was a reduction in the G2M accumulation and an increased sub-G0 population (15%). In comparison, un-irradiated as well as irradiated SCC066 cells demonstrated a modest reduction in G2M accumulation following treatment with ATR siRNA but no corresponding increase in the dead (sub-G0) cell population. A similar sensitization of UPCI:SCC104 but not UPCI:SCC066 was observed following treatment with CHEK1 siRNA. Following treatment with a non-specific scrambled siRNA, SCC104 does not exhibit any reduction in the G2M accumulation or increase in the sub-G0 population. This suggests that the effects observed were specific for ATR and CHEK1 inhibition.

Thus, UPCI:SCC104 was highly sensitized to IR following inhibition of the upregulated ATR-CHEK1 pathway with the respective siRNAs. These results suggest that SCC104 with ATR and CHEK1 overexpression is highly susceptible to IR, following treatment with ATR or CHEK1 siRNA.

To determine if the PCC/MC formation associated with caffeine treatment was mediated through its inhibition of the ATR-CHEK1 pathway, ATR and CHEK1 siRNAs were used to produce a specific knockout. A very high level of PCC/MC in UPCI:SCC104 was detected following treatment with either ATR or CHEK1 siRNA (FIG. 23). In comparison UPCI:SCC066 had a modest increase in the number of cells undergoing PCC/MC in response to inhibition of the ATR-CHEK1 pathway.

Finally, cell survival of UPCI:SCC066 and 104 after treatment with ATR siRNA was studied in the absence of any DNA damaging agents (FIG. 24A-B). Complete inhibition of colony formation was observed in SCC104 treated with ATR siRNA at the end of 12 days. In comparison, UPCI:SCC066 did not demonstrate a significant reduction in cell survival.

Thus, these results suggest that the ATR-CHEK1 pathway is upregulated in a subset of OSCC and ATR and/or CHEK1 may be potential targets to sensitize a subset of OSCC to DNA damaging agents.

7. EXAMPLE

Loss of Distal 11q is Associated with DNA Repair Deficiency and Reduced Sensitivity to Ionizing Radiation

7.1 Materials and Methods

Cell Culture. HNSCC cell lines, normal human oral keratinocytes (NHOK), and normal human fibroblasts were established in the inventors' laboratory. hTERT-transfected human oral keratinocytes were OKF6/TERT-1 from the laboratory of Dr. James G. Rheinwald; Dickson et al., 2000. GM09607, an ATM null cell line, was from Coriell Cell Repositories, Camden, N.J. The HNSCC cell lines were grown in Minimal Essential Medium (Gibco Invitrogen, Grand Island, N.Y.), supplemented with 1% non-essential amino acids, 1% L-glutamine, 0.05 mg/ml Gentamicin and 10% FBS) (all supplements from Gibco Invitrogen) (White et al., 2006). NHOK established from uvulopalatopharyngoplasty specimens were cultured in serum-free KGM-2 medium (Clonetics, Walkersville, Md.), supplemented with BPE (bovine pituitary extract), hEGF, insulin (bovine), hydrocortisone, GA-1000 (Gentamicin, Amphotericin B), epinephrine and transferrin as per the manufacturer's instructions (supplements supplied in the KGM-2 BulletKit™ from Clonetics). Finite passage normal human fibroblasts established from uvulopalatopharyngoplasty tissue were cultured in Minimal Essential Medium (Gibco Invitrogen), supplemented with 1% non-essential amino acids, 1% L-glutamine, 0.05 mg/ml Gentamicin and 10% FBS) (Gibco Invitrogen). The OKF6/TERT-1 cells were initially cultured in Keratinocyte-SFM supplemented with 25 µg/ml bovine pituitary extract, 0.2 ng/ml epidermal growth factor, 0.3 mM CaCl2 and penicillin-streptomycin (Gibco Invitrogen). These keratinocytes were expanded to high density in a 1:1 mixture of Keratinocyte-SFM and DMEM-F12. The DMEM-F12 was a 1:1 mixture of calcium-free and glutamine-free DMEM and Ham's F-12 supplemented with 25 µg/ml bovine pituitary extract, 0.2 ng/ml epidermal growth factor, 1.5 mM L-glutamine and penicillin-streptomycin (Gibco Invitrogen). GM09607 (Coriell Cell Repositories, Camden, N.J.) was cultured in Dulbecco's Modified Eagle Medium (DMEM), supplemented with 1% non-essential amino acids, 0.05 mg/ml penicillin-streptomycin-L-glutamine, and 10% FBS (Gibco Invitrogen).

Fluorescence In Situ Hybridization (FISH). To prepare mitotic cells for FISH analyses, HNSCC cells were harvested following a 5 h treatment with 0.1 µg/ml Colcemid™ (Irvine Scientific, Santa Ana, Calif.), hypotonic KCl (0.075M) treatment for 16 min, and fixation in 3:1 methanol:glacial acetic acid. All other cells were harvested using the same method, except that 1 h of Colcemid™ was preferred for non-tumor cells. FISH analysis was used to detect copy number changes in the CCND1, MRE11A, ATM and H2AFX genes in the HNSCC cell lines. For FISH analysis, cells were harvested, dropped onto slides, treated with RNase/2×SSC, and dehydrated using a graded series (70%, 80% and 100%) of ethanol washes. Chromatin was denatured with 70% formamide and the cells were dehydrated in a second graded series of ethanol washes. The CCND1, ATM, MRE11A and H2AFX probes for FISH were prepared following DNA extraction from BACs purchased from Children's Hospital of Oakland Research Institute (CHORI, Oakland, Calif.). The BAC DNA was isolated and labeled using a nick translation kit from Vysis/Abbott Molecular Inc. (Des Plaines, Ill.). The labeled DNA was precipitated with ethanol, resuspended in hybridization buffer, denatured for 5 min at 75° C., and preannealed for 15-30 min at 37° C. Each probe was hybridized for 16 h at 37° C., after which slides were washed with SSC/Tween-20. Slides were counterstained with DAPI and mounted with antifade prior to analysis. All FISH analyses were carried out using an Olympus BX-61 epifluorescence microscope (Olympus Microscopes, Melville, N.Y.). An Applied Imaging CytoVision workstation with Genus v3.6 software was used for image capture and analysis (Applied Imaging, San Jose, Calif.).

Paraffin and Frozen Section FISH. Anonymous frozen sections of breast carcinomas and paraffin sections of the stage III ovarian carcinomas were obtained from the Magee-Womens Hospital Tissue Procurement Program. The paraffin sections of anonymous HNSCC were obtained from the Head and Neck SPORE Tissue Bank at the University of Pittsburgh. 4-5 µM thick sections of formalin-fixed, paraffin-embedded tissue were mounted on positively charged microscope slides. The slides were aged overnight at 60° C., following which they were deparaffinized twice with xylene for 5 min each at room temperature. The slides were dehydrated in two 100% ethanol washes, 2 min each at room temperature. The slides were then treated with 0.5×SkipDewax solution (Insitus Biotechnologies, Albuquerque, N. Mex.) at 80° C. for 15 min followed by a wash in distilled water for one min at room temperature, treatment in 0.2N HCl for 20 min at room temperature, pretreatment with 1 M sodium thiocyanate at 80° C.

for 30 min, a wash in distilled water for one min at room temperature, two washes with 2×SSC 5 min each, and then treatment with protease (pepsin) solution for 15 min at 37° C. Next, the slides were fixed in 10% Formalin for 10 min at room temperature. After two 2×SSC washes at room temperature, the slides were dehydrated with a graded series of ethanol washes at room temperature, and allowed to dry on slide warmer. Next, slides were denatured at 75° C. in 70% formamide, followed by a cold series of ethanol washes. The probes for paraffin FISH were prepared as described for FISH above. The hybridization of the FISH probes and post-hybridization treatment of the paraffin sections was carried out as described for FISH above.

4-5 µM thick sections of OCT-embedded, fresh frozen breast carcinomas were mounted on positively charged microscope slides. The slides were placed in 0.8% sodium citrate for 20 min, fixed in 3:1 methanol acetic acid, and air dried. The slides were aged at 90° C. for 10 min, digested in 0.005% pepsin in 0.2N HCl at 37° C. for 60 sec, incubated in 70% ethanol for 30 sec, pretreated in 2×SSC at 37° C. for 60 min, dehydrated in a graded series of ethanol, denatured and hybridized as for FISH above.

Quantitative Microsatellite Analysis (QuMA). QuMA analysis to detect copy number changes in microsatellite markers along chromosome arm 11q was carried out as described in Huang et al., 2002, 2006. PCR primer sequences for the microsatellite loci are shown in Appendix D. The TaqMan CA-repeat fluorogenic probe used for all loci consisted of the following sequence: 5'-FAM (6-carboxy fluorescein)-TGTGTGTGTGTGTGTGTGTGTGT-TAMRA (6-carboxytetramethylrhodamine)-3' (SEQ ID NO:26). All of the probes and primers for QuMA were purchased from Integrated DNA Technologies (Coralville, Iowa).

Loss of Heterozygosity. For the LOH studies, DNA was isolated from HNSCC cell lines by standard SDS/proteinase K/phenol-chloroform extraction methods. Genotypes of the cell lines were compared to constitutional DNA isolated from the patient's blood. Microsatellite loci for chromosome arm 11q were chosen from published maps, and samples were PCR-amplified using standard 32P techniques. Standard cycling conditions for LOH were as follows: following denaturation at 94° C. for 5 min, samples were subjected to 35 cycles of 94° C. for 45 sec, 55° C. for 45 sec and 72° C. for 45 sec. Amplified products were electrophoresed through a 6% denaturing polyacrylamide gel with appropriate size standards, before exposure to x-ray film. Complete or nearly complete loss (≥90%) of an allele at a given locus was called "LOH." Allelic loss greater than 50% was called "partial LOH," and allele loss less than 50% was not considered ("no LOH").

Quantitative Reverse Transcriptase PCR(RT-PCR). RT-PCR was performed to detect expression of MRE11A, ATM and H2AFX in HNSCC. Taqman primers and probes were designed with Primer Express V.2.0.0 (Applied Biosystems, Foster City, Calif.). The reverse transcriptions were carried out as previously in Huang et al., 2002. Quantitative PCR (QPCR) was performed on the cDNA using the ABI 7700 Sequence Detection Instrument (Applied Biosystems) and analyzed using the relative quantitation method (User Bulletin, PE Applied Biosystems) as in Huang et al. (2002). QPCR was carried out for MRE11A, ATM, H2AFX and ribosomal 18S RNA (endogenous control) with primers and probes listed in Appendix D. For the QPCR, the final concentrations of the reaction components were as follows: PCR buffer A (Applied Biosystems), 300 nM each dNTP, 3.5 mM MgCl2, 0.06 units/µl Amplitaq Gold (Applied Biosystems), 500 nM (100 nM for 18S RNA) primers, and 200 nM (100 nM for 18S RNA) probe. The thermocycler conditions were 95° C. Taq activation for 12 min and 40 cycles (30 cycles for 18S RNA) of 95° C. denaturation for 15 sec followed by 60° C. anneal/extend (64° C. for MRE11A and H2AFX) for 60 sec.

Immunoblotting. Immunoblotting was utilized to detect protein expression of MRE11A, ATM and H2AX in HNSCC cell lines, and also to assess the phosphorylation levels of H2AX following exposure to 2.5 Gy IR. Flasks of each cell line were trypsinized, washed with ice cold 1×PBS and lysed on ice with a solution containing 50 mM Tris, 1% Triton X-100 (Sigma), 0.1% sodium dodecyl sulfate (Bio-Rad Laboratories, Hercules, Calif.), 150 mM NaCl (Fisher Chemicals, Fairlawn, N.J.), 1 mM dithiothreitol (DTT) (Fisher Scientific, Inc., Hampton, N.H.), 10 µg/ml leupeptin (Roche Applied Science, Indianapolis, Ind.), 10 µg/ml pepstatin (Roche Applied Science) and 1 nM phenyl methyl sulfonyl fluoride (PMSF) (Santa Cruz Biotechnology, Inc., Santa Cruz, Calif.). The soluble cell lysate was centrifuged at 2000×g for 15 min, and transferred to a clean microfuge tube. Histone H2AX was extracted from the remaining pellet containing insoluble protein and chromatin. The pellet was treated with 0.1N (3.65 g/L) HCl for 20 min on ice, and then centrifuged at 10,000×g for 10 min.

Protein concentrations were determined using the Bio-Rad Quick Start Bradford Protein Assay Kit and the SmartSpec 3000 (Bio-Rad Laboratories). The acid lysate was neutralized with Tris-EDTA (TE) pH 8.0 prior to normalization. Normalized lysates were resolved by sodium dodecyl sulfate polyacrylamide gel electrophoresis (SDS-PAGE) and transferred onto an Immobilon-P membrane (Millipore Corporation, Billerica, Mass.). After blocking with 5% non-fat dry milk (NFDM) for 1 h, the membrane was incubated overnight with antibodies for ATM (5C2, used at 1:1000), MRE11A (C-16, used at 1:1000), total H2AX (used at 1:1000) or mouse anti-phospho-Histone H2AX (Ser139, clone JBW301, used at 1:1000) at room temperature (ATM and MRE11A from Santa Cruz Biotechnology, Inc.; total H2AX from Cell Signaling Technology, Inc., Danvers, Mass.; γ-H2AX from Upstate Technology, Inc., Lake Placid, N.Y.). Following three 5 min washes in 1×TBST (Tris-buffered Saline Tween-20), the membrane was incubated with the appropriate secondary antibody (1:3000) for 2 h. Target proteins were visualized using the Western Lightning™ Chemiluminescence Reagent Plus kit (PerkinElmer Life Sciences, Boston, Mass.) according to the manufacturer's instructions. To verify equal protein loading in the gels, membranes were stripped and re-probed with antibodies against β-actin (Sigma Immunochemicals, St. Louis, Mo.) or α-actinin (Sigma Immunochemicals) (all at a 1:1000 dilution). A densitometric analysis was carried out using Un-Scan-It Gel™ (Silk Scientific, Inc., Orem, Utah).

Immunofluorescence. Changes in γ-H2AX focus formation after exposure to 2.5 Gy IR were determined using Gammacell 1000 Elite irradiator (Nordion International, Inc., Ottawa, Canada) with a 137Cs source at a dose rate of 4.42 Gy/min. Each cell line was passaged into single-well chamber slides (Nalge Nunc International, Rochester, N.Y.) one day prior to treatment with ionizing radiation. A parallel set of slides was mock-treated (medium change only) as a control. Following exposure to IR, the cells were washed with 1×HBSS (Irvine Scientific), the medium was replaced, and the chamber slides were incubated under standard culture conditions for 1 h to allow for repair. After repair, the cells were washed with 1×PBS, fixed with 4% paraformaldehyde (PFA) (Sigma) for 30 min and permeabilized with 0.2% triton/1×PBS. Following permeabilization, cells were blocked with 5% goat serum/1×PBS and incubated with anti-phospho-H2AX primary antibody (Upstate Technology, Inc.) for 2 h. The primary antibody was detected with a goat anti-mouse Alexa 488 (Molecular Probes, Eugene, Oreg.) for 1 h. Cells were then washed, counterstained with DAPI, mounted using antifade and analyzed under an epifluorescence microscope as previously described. A minimum of 100 cells were scored from control and IR-treated chamber slides for each of the cell lines by two independent observers for a total of at least 200 cells. An additional two datasets, each including a minimum of 200 cells, were accumulated using a spot-counting algorithm on a MetaSystems Metafer scanning system (trial use courtesy of MetaSystems, Altlussheim, Germany). The mean level of focus formation was calculated using the three independent samples, and 95% confidence intervals were generated to illustrate the distribution in the data.

Viability Assay. To assay the fraction of cells undergoing apoptosis at the time of treatment, the Reduced Biohazard Cell Viability/Toxicity Kit (Molecular Probes) was used on chamber slides (Nalge Nunc International) set up in parallel with slides made for immunofluorescence visualization of foci. In brief, slides were treated with identical doses of IR, and allowed to repair for 1 h before being washed in HEPES buffer (Irvine Scientific), and incubated in 1:500 dilutions each of SYTO 10 green fluorescent nucleic acid stain and DEAD Red ethidium homodimer-2 in HEPES buffer for 15 min. Slides were mounted in 1×PBS and visualized using an Olympus epifluorescence microscope at 100× magnification. Viability was determined by cellular staining, wherein membrane-competent cells appeared green, and the cells with compromised cellular membranes appeared red. Results for the assay, carried out in triplicate, are reported as mean percentage of surviving cells with 95% confidence intervals.

Anaphase Bridges

Anaphase bridging was analyzed in HNSCC cell lines and OKF6/TERT-1 cells grown on chamber slides (Nalge Nunc International) after treatment with Colcemid™ (Irvine Scientific); cells were otherwise untreated. Cells were arrested in metaphase with 0.1 g ml Colcemid™ for 5 h, washed in 1×HBSS, and allowed to resume their respective cell cycles for 3-4 h prior to fixation in Carnoy's fixative (3:1 methanol: glacial acetic acid). Chamber slides were stained with DAPI. A minimum of 500 cells were analyzed for each cell line, and the frequencies of anaphase bridging and nucleoplasmic bridging were recorded. A test of proportions was used to compare the frequencies in each of the HNSCC cell lines relative to the frequency observed in the OKF6/TERT-1 cells (0.74), and p-values were reported.

Chromosome Aberration Analysis. Flasks of UPCI: SCC084, 104 and 116 were trypsinized and then subjected to 2.5Gy of IR. The cells were re-seeded into T-25 flasks, and allowed to repair for 48 h prior to being harvested with a final concentration of 0.1 µg/ml Colcemid™ and 18 nM Calyculin A for 30 min (Calbiochem, San Diego, Calif.). Since cells lacking a G1 phase cell cycle checkpoint and those with a defective DNA damage response are often blocked in G2, to avoid skewing of the data, we analyzed the chromosomes from G2 cells after premature chromosome condensation with Calyculin A. Harvested cells were subjected to a hypotonic treatment before being fixation in Carnoy's fixative. Slides were then prepared from the cell pellets and dried overnight, solid stained for 8 min in 4% Giemsa/PBS solution, and rinsed with distilled water. Two researchers independently scored 25 cells each per cell line, per treatment. Chromosome aberrations included: chromosome breaks, chromatid gaps or breaks, quadriradials, triradials, rings, dicentrics, and fragments. Chromosome breaks, radials, rings and dicentrics were assigned twice the weight of the other aberrations, as they involve two chromatid breakage events. The total weighted aberrations were summed, and determined per chromosome and per cell for each treatment. The standard error of the mean was used as the estimate of error in the sample. A Student's t-test was used to compare the raw distributions of total weighted aberrations between the control and IR-treated samples.

Clonogenic Survival Assay. To assess cell survival in response to ionizing radiation, a clonogenic survival assay was performed. Two thousand cells were seeded in 60 mm Petri dishes and allowed to attach overnight. Cells were then treated with increasing doses of γ-irradiation at 1, 2.5, 5, and 10 Gy. The cell culture medium was changed at the end of seven days. Mock-treated cells, cultured in parallel, were used to determine relative plating efficiency. After 12 days, the colonies were stained with Giemsa (Sigma) and counted. A colony was defined as a cluster of ≥50 cells, presumably having formed from a single cell. All experiments were performed in triplicate, and error is reported as one standard deviation from the mean.

7.2 Results

Partial Loss of MRE11A, ATM and H2AFX in HNSCC. Dual-color FISH was performed with BAC probes to MRE11A, ATM and H2AFX along with a centromere 11 enumeration probe in HNSCC (CEP 11; D11Z1) (Vysis/Abbott Molecular Inc.). Table 12 summarizes these FISH results. The copy number ratios of the distal 11q genes were determined to be either lost or normal with respect to CEP. Based on these results, the eleven cell lines were grouped as follows. All cell lines with 11q13 amplification were haploinsufficient for MRE11A, ATM and H2AFX, including UPCI:SCC078, 084, 131 and 136 ("Amplification with Loss"). The HNSCC cell lines, UPCI:SCC104, 142 and 122 were haploinsufficient for either MRE11A, ATM and/or H2AFX in the absence of 11q13 amplification ("No Amplification with Loss"). UPCI:SCC099, 116 and 182 had neither 11q13 amplification nor distal 11q loss ("No Amplification, No Loss"). UPCI:SCC125 is comprised of a highly heterogeneous cell population, making its analysis less straightforward than the other cell lines. There is no evidence for 11q13 amplification in this cell line. While the copy number ratios would suggest that UPCI:SCC125 is normal in copy number for MRE11A, ATM and H2AFX, FISH results indicated that MRE11A (31% loss, 44% gain), ATM (52% loss, 1% gain), H2AFX (43% loss, 25% gain) gene copy numbers are more a function of the average than the norm. Thus, for the purposes of this study, this cell line is expected to respond somewhere between cell lines with "No Amplification with Loss" and those with "No Amplification, No Loss," given the absence of 11q13 amplification.

TABLE 12

Summary of 11 HNSCC Cell Lines, Including FISH Copy Number Results Expressed as Ratios Relative to the Chromosome 11 Centromere

| Cell Line UPCI: | TP53 status Exons 5-9 | Ploidy | 11q13 amp (+/-) | Distal 11q loss (+/-) | FISH Results MRE11A[a] | ATM[a] | H2AFX[a] |
|---|---|---|---|---|---|---|---|
| SCC099 | WT | 2-4 | - | - | 1.00 | 0.98 | 1.02 |
| SCC116 | mut | 3-4 | - | - | 0.96 | 0.97 | 0.96 |
| SCC182 | mut | 3 | - | - | 1.01 | 0.97 | 0.98 |
| SCC078 | mut | 3-4 | + | + | 0.38 | 0.54 | 0.84 |
| SCC084 | mut | 2 | + | + | 0.51 | 0.52 | 0.52 |
| SCC131 | WT | 4 | + | + | 0.56 | 0.59 | 0.53 |
| SCC136 | mut | 4 | + | + | 0.57 | 0.60 | 0.56 |
| SCC104 | WT | 4 | - | + | 0.98 | 0.51 | 0.50 |
| SCC122 | mut | 3 | - | + | 0.69 | 0.68 | 0.71 |
| SCC142 | WT | 3 | - | + | 0.93 | 0.67 | 0.79 |
| SCC125[b] | mut | 3 | - | +/- | 1.08 | 0.79 | 0.97 |

[a]Dark shading indicates partial loss or haploinsufficiency.
[b]UPCI:SCC125 is distinguished from the cell lines with "no 11q13 amp, distal 11q loss" because it is heterogeneous with respect to copy number, as evidenced by the mixture of cells showing gain or loss for any given gene in a single slide preparation.

Confirmation of Physical Loss of Distal 11q was Carried Out by Two Additional Methods. Quantitative microsatellite analysis, or QuMA, was used to map DNA copy number of sequential microsatellite loci along 11q. The resulting profiles were grouped according to the FISH data for relative copy number loss of MRE11A, ATM and H2AFX along 11q. The results, which demonstrate reduction in copy number of each of these markers, support the findings of our FISH experiments. LOH analysis was performed as an independent test to validate our FISH and QuMA results, and results were available for nine of the eleven cell lines. The results of LOH analysis, summarized in FIG. 26 substantiate the loss patterns observed for distal 11q using FISH and QuMA, as extended segments of 11q were shown to have complete or partial LOH in the "No Amplification with Loss" and "Amplification with Loss" HNSCC cell line groupings. The cell lines with "No Amplification, No Loss" do not have significant LOH along 11q. Thus, the results from FISH, QuMA and LOH studies corroborate the 11q loss in the HNSCC cell lines.

TABLE 13

Summary of FISH Copy Number Changes in CCND1 and ATM in Ovarian Tumors, Head and Neck Squamous Cell Carcinomas, and Primary Breast Tumors.

| Tumor | | CCND1 | | | | ATM | | | |
|---|---|---|---|---|---|---|---|---|---|
| | | Amp | Gain | Normal | Loss | Amp | Gain | Normal | Loss |
| Ovarian cancer | | | | | | | | | |
| TP 02-349 | N[a] | 0 | 0 | 100 | 0 | 0 | 0 | 99 | 1 |
| | T[a] | 25 | 11 | 64 | 0 | 0 | 3 | 95 | 2 |
| TP 02-255 | N | 0 | 0 | 100 | 0 | 0 | 0 | 100 | 0 |
| | T | 4 | 12 | 84 | 0 | 0 | 0 | 85 | 15 |
| TP 02-217 | N | 0 | 0 | 100 | 0 | 0 | 2 | 96 | 2 |
| | T | 2 | 5 | 93 | 0 | 0 | 0 | 97 | 3 |
| TP 02-238 | N | 0 | 0 | 100 | 0 | 0 | 0 | 100 | 0 |
| | T | 4 | 8 | 88 | 0 | 0 | 5 | 41 | 54 |
| TP 02-500 | N | 0 | 2 | 98 | 0 | 0 | 2 | 96 | 2 |
| | T | 16 | 16 | 66 | 0 | 0 | 5 | 53 | 42 |
| TP 02-545 | N | 0 | 3 | 97 | 0 | 0 | 2 | 96 | 2 |
| | T | 22 | 12 | 66 | 0 | 6 | 10 | 79 | 5 |
| TP 02-528 | N | 0 | 3 | 95 | 2 | 0 | 0 | 98 | 2 |
| | T | 6 | 12 | 82 | 0 | 0 | 7 | 51 | 42 |
| TP 02-539 | N | 0 | 1 | 97 | 2 | 0 | 0 | 100 | 0 |
| | T | 16 | 31 | 53 | 0 | 0 | 11 | 87 | 2 |
| TP 02-505 | N | 0 | 0 | 100 | 0 | 0 | 0 | 100 | 0 |
| | T | 81 | 14 | 5 | 0 | 0 | 0 | 93 | 7 |
| TP 02-236 | N | 0 | 2 | 98 | 0 | 0 | 2 | 98 | 0 |
| | T | 13 | 17 | 70 | 0 | 89 | 0 | 11 | 0 |
| HNSCC | | | | | | | | | |
| 62102-3 | N | 0 | 2 | 97 | 1 | 0 | 0 | 95 | 5 |
| | T | 58 | 23 | 19 | 0 | 0 | 0 | 54 | 46 |
| 62009-5 | N | 1 | 1 | 98 | 0 | 0 | 0 | 97 | 3 |
| | T | 11 | 36 | 51 | 2 | 0 | 0 | 34 | 66 |
| 62134-0 | N | 0 | 1 | 99 | 0 | 0 | 0 | 100 | 0 |
| | T | 98 | 1 | 1 | 0 | 0 | 0 | 47 | 53 |
| 62004-0 | N | 0 | 0 | 100 | 0 | 0 | 0 | 98 | 2 |
| | T | 4 | 0 | 94 | 2 | 0 | 2 | 42 | 56 |
| 61936-7 | N | 0 | 1 | 99 | 0 | 0 | 1 | 98 | 1 |
| | T | 99 | 1 | 0 | 0 | 0 | 0 | 41 | 59 |
| Breast cancer | | | | | | | | | |
| TP 98-279 | T | 90 | 6 | 4 | 0 | 0 | 0 | 77 | 23 |
| TP 98-323 | T | 0 | 62 | 38 | 0 | 0 | 0 | 43 | 57 |
| TP 98-350 | T | 0 | 6 | 94 | 0 | 0 | 1 | 89 | 10 |
| TP 98-410 | T | 0 | 10 | 90 | 0 | 0 | 0 | 91 | 9 |
| TP 98-015 | T | 0 | 7 | 91 | 2 | 0 | 2 | 90 | 8 |
| TP 99-051 | T | 91 | 4 | 5 | 0 | 0 | 0 | 70 | 30 |
| TP 99-060 | T | 0 | 16 | 81 | 3 | 0 | 4 | 88 | 8 |
| TP 99-084 | T | 0 | 5 | 93 | 2 | 0 | 0 | 96 | 4 |
| TP 99-110 | T | 0 | 12 | 84 | 4 | 0 | 1 | 88 | 11 |
| TP 99-117 | T | 1 | 7 | 93 | 0 | 0 | 0 | 93 | 7 |

[a]T represents tumor tissue and N represents surrounding normal tissue as demarcated by histological and pathological studies. A minimum of 50 cells were counted for each tumor and normal tissue studied.

Partial Loss of ATM in Primary Head and Neck, Ovarian and Breast Tumors. Paraffin FISH was used to study copy number changes in ATM and CCND1 in primary head and neck squamous cell carcinomas, ovarian and breast carcinomas. Table 13, above, summarizes these results (see also Section 8, below). It was found that three of five primary head and neck tumors showed CCND1 amplification, whereas all five primary head and neck tumors showed partial loss of ATM compared to CEP 11. Partial ATM loss was also seen in four of ten ovarian tumors studied and three of ten breast carcinomas studied. For the primary head and neck and ovarian tumors, the changes in CCND1 and ATM copy number were also studied in the tumor adjoining normal tissue. Thus, these results indicate that partial loss of ATM is associated with tumor types in addition to HNSCC.

Distal 11q Loss is Associated with Chances in Expression of MRE11A, ATM and H2AFX. Taqman quantitative reverse transcriptase PCR (RT-PCR) and immunoblotting were performed to assess whether loss of MRE11A, ATM and H2AFX led to a reduction in their expression (FIG. 29A). The detectable expression of ATM and H2AX in the HNSCC generally correlated with gene copy number, especially for the ATM gene. The "Amplification with Loss" cell lines are haploinsufficient based on physical loss of distal loci, and generally exhibit reduced RNA expression relative to controls. SCCHN cell lines are heterogenous for loss of distal 11q and not all cells within a cell line show this loss. This heterogeneity is reflected in the relative RNA and protein expression in our studies.

Protein expression in HNSCC cell lines and various controls was assessed by immunoblotting (FIG. 29B). The results show that cell lines with distal 11q loss tend to have an overall lower expression level of MRE11, ATM and H2AX in comparison to those cell lines without distal 11q loss. The relative protein expression data correlate with the quantitative RT-PCR analysis. The results also show that untreated HNSCC cell lines have low levels of γ-H2AX, and nearly uniform increases in H2AX phosphorylation one hour after treatment with 2.5 Gy IR. These results are not particularly correlated with γ-H2AX focus formation, which is a widely accepted measure of the DNA damage response. Changes in H2AX protein phosphorylation may not be detectable by immunoblotting in our HNSCC cell lines.

Decreased Expression of MRE11A, ATM and H2AFX Correlates with Aberrant γ-H2AX Foci. γ-H2AX focus formation was evaluated after treatment with 2.5 Gy IR. Constitutive γ-H2AX foci were seen in some of the cell lines (UPCI: SCC099 and 116, among others) in the absence of exogenous genetic insult. Hence, γ-H2AX focus formation following IR was assayed by several measurements, including the mean number of foci per cell, the distribution of foci in 200 cells, and the percent of focus-positive cells. Comparison of the mean number of foci per cell in mock-treated and IR-exposed cells is shown in FIG. 27. The highest mean numbers of foci were seen in the cell lines "No Amplification, No Loss" (min=5.93±0.75; max=8.20±1.16), and these were similar to those of the control fibroblast cell line (10.34±0.65). The cell lines with "Amplification with Loss" showed the lowest mean levels of γ-H2AX foci. When treated with IR, the mean number of γ-H2AX foci was more than two-fold lower in the cell lines with amplification and loss than cell lines without 11q loss (min=3.93±1.23; max=6.05±0.87). "No Amplification with Loss" cell lines also showed low levels of γ-H2AX focus formation after IR (min=2.38±1.46; max=7.81±1.03). While there was γ-H2AX focus formation in the mock-treated ATM−/− control cell line, there was essentially no difference between the mock-treated and IR-treated cells after one hour, thereby serving as a negative control. Cell lines that have fewer focus-positive cells and have a reduced mean number of foci per cell following IR are considered defective in γ-H2AX focus formation. The distribution of focus-positive cells also reveals a deficient response when the data are categorized as 0-2, 3-10 and >10 foci (FIG. 30A-B). Following IR, the distribution of focus-positive cells with "No Amplification, No Loss" closely resembles the distribution seen in normal fibroblasts. The "Amplification with Loss" and "No Amplification with Loss" cell lines tend to show more deficient responses than the "No Amplification, No Loss" or normal fibroblasts, as small proportions of these cells have more than 10 foci. The signal distribution in the ATM null cell line is essentially unchanged following IR.

Since H2AX phosphorylation and formation of γ-H2AX foci occurs in response to double strand breaks or apoptotic DNA fragmentation, late-appearing foci may represent irreparable damage to the cell (Rogakou et al., 2000). To evaluate if the γ-H2AX foci we observed were in response to double strand breaks or as a precursor to apoptosis, a cell viability assay was performed. Significant cell death was not expected to occur within 1 h as a result of a 2.5 Gy IR treatment. In UPCI:SCC116, 94.0±0.05% of the control population and 92.6±0.15% of the treated cells remained viable (FIG. 31). In UPCI:SCC084, 90.7±0.07% of the control population and 91.7±0.09% of the treated population were viable. In UPCI:SCC104, 94.1±0.04% of the control cells and 91.1±0.08% of the treated cells remained viable. As expected, the control and treated confidence intervals overlap in all three cases, indicating that there was no difference between the cell lines with respect to survival and confirming that cell death did not significantly skew the focus formation assay results.

Loss of Distal 11q is Associated with Increased Chromosomal Instability.

Figure 7:
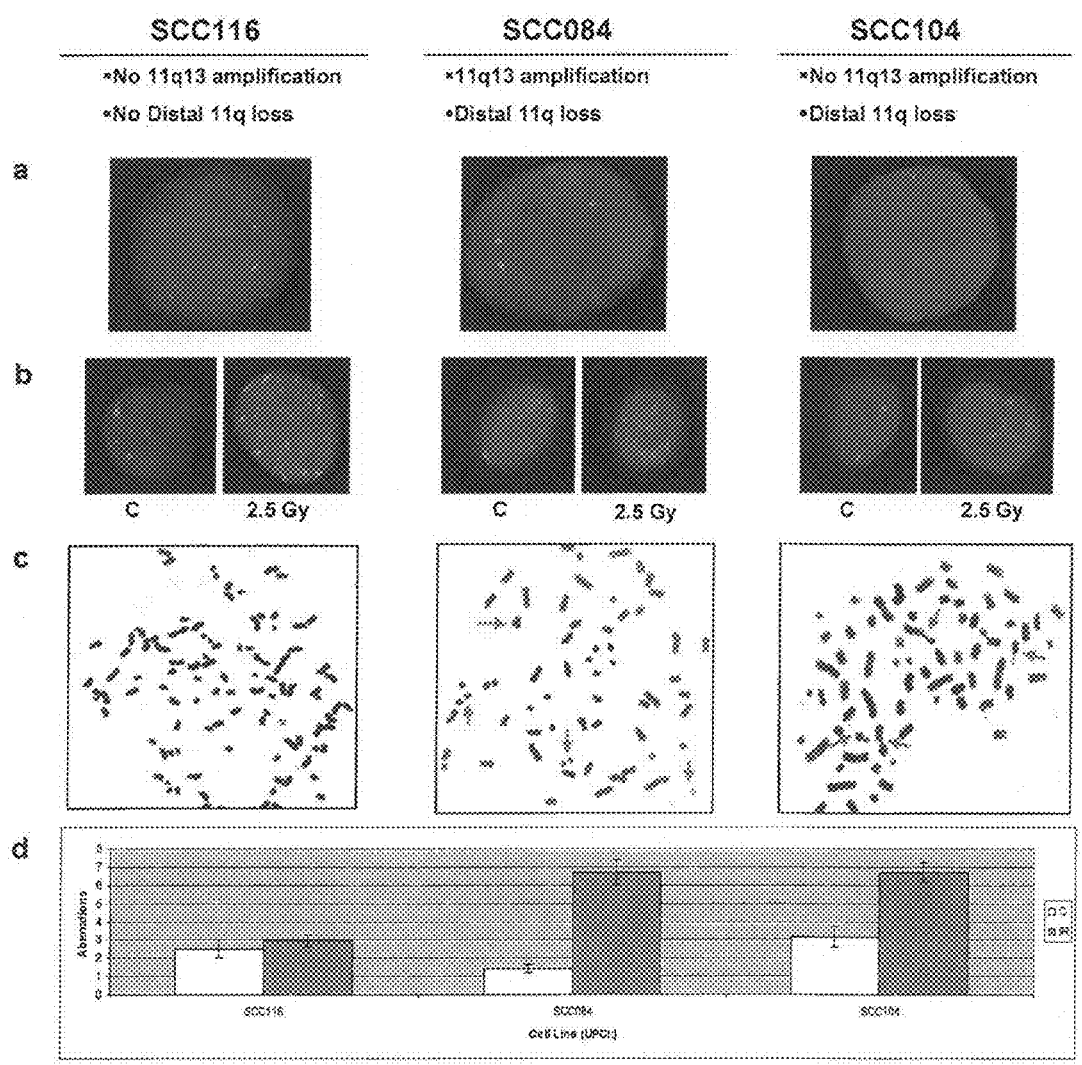

The number of weighted aberrations per chromosome 48 h after IR was determined for UPCI:SCC084, 104 and 116 by using Calyculin A to prematurely condense chromatin for analysis of G2 and mitotic phase chromosomes (FIG. 7D and Table 14A). Breaks were evident in the cell lines with loss of distal 11q, irrespective of 11q13 status. Complete results are summarized in Table 13a. There is no significant difference in the total chromosomal aberrations per cell between the control (2.52±0.97%) and IR-treated (2.94±0.62%) populations in UPCI:SCC116, which is from the "No Amplification, No Loss" grouping. There is substantial agreement between the results for UPCI:SCC084 (C=1.43±0.51%; IR=6.68±1.40%; p<0.001) and UPCI:SCC104 (C=3.15±0.76%; IR=6.68±1.05%, p<0.001), both of which have loss of distal 11q. Thus, the cell lines with distal 11q loss, regardless of amplification status (UPCI:SCC084 (Amplification with Loss) and UPCI:SCC104 (Loss, No Amplification)) demonstrated significantly higher levels of chromosomal aberrations in response to ionizing radiation when compared to a cell line without distal 11q loss (UPCI:SCC116; No Amplification, No Loss).

The frequency of anaphase bridges in 500 cells was used an indicator of chromosomal instability. The frequency of anaphase bridges in each cell line is summarized as a percentage in Table 14B. Overall, the lowest frequency was seen in OKF6/TERT-1 cells (0.74%). The lowest frequency among all HNSCC cell lines was seen in UPCI:SCC116 (0.96%), and the highest frequency was seen in UPCI:SCC142 (5.63%). In cell lines without 11q loss, the maximum frequency (1.31%; UPCI:SCC099) was lower than any of the frequencies observed in cell lines with 11q loss (in the "Amplification with Loss" and "Loss, No Amplification" groups). In a comparison of proportions, all cell lines with distal 11q loss, irrespective of 11q13 amplification, have significantly elevated frequencies of anaphase bridges relative to the immortalized oral keratinocytes and "No Amplification, No Loss" cell lines. For two of the cell lines, UPCI:SCC078 and 122, the p-value is less than 0.1. For all other cell lines with distal 11q loss, the p-value is less than 0.05. Since the frequency of anaphase bridges was measured in untreated cell lines, the intrinsic level of chromosomal instability is higher in cell lines with 11q loss.

TABLE 14A

Results from the Chromosomal Aberration Assay for Representative Cell Lines

| Cell Line UPCI: | SCC116 | | SCC084 | | SCC104 | |
|---|---|---|---|---|---|---|
| 11q13 Amplification (+/−) | − | | + | | − | |
| Distal 11q Loss (+/−) | − | | + | | + | |
| Exposure | C | 2.5Gy IR | C | 2.5Gy IR | C | 2.5Gy IR |
| Total Weighted Aberrations per Chromosome ± 95% CI | 0.05 ± 0.02 | 0.06 ± 0.01 | 0.03 ± 0.01 | 0.15 ± 0.03 | 0.07 ± 0.02 | 0.15 ± 0.02 |
| Total Weighted Aberrations per Cell ± 95% CI[a] | 2.52 ± 0.97 | 2.94 ± 0.62 | 1.43 ± 0.51 | 6.68 ± 1.40 | 3.15 ± 0.76 | 6.68 ± 1.05 |

[a]Dark shading indicates a significant result for the Student's t-test (p<0.001).

TABLE 14B

Frequency of Anaphase Bridges in Untreated HNSCC Cell Lines

| Cell Line UPCI: | SCC116 | SCC182 | SCC099 | SCC078 | SCC084 | SCC131 | SCC136 | SCC104 | SCC122 | SCC142 | SCC125 |
|---|---|---|---|---|---|---|---|---|---|---|---|
| 11q13 Amplification (+/−) | − | − | − | + | + | + | + | − | − | − | − |
| Distal 11q Loss (+/−) | − | − | − | + | + | + | + | + | + | + | +/− |
| Anaphase Bridges (%)[a] | 0.96 | 1.27 | 1.31 | 1.86 | 2.65 | 3.08 | 3.58 | 4.14 | 1.87 | 5.53 | 3.1 |

[a]Test of proportions to compare the frequency of anaphase bridges in each cell line to the frequency observed in immortalized oral keratinocytes (0.74%). Shading indicates a significant difference; light gray shading denotes p<0.1, and dark gray shading indicates values where p<0.05.

TABLE 15

| Cell Line | Dose of IR Gy) | Individual Mean ± SD | Grouped Mean ± SD |
|---|---|---|---|
| NHOK | 0 | 100.0 ± 0.0 | |
| | 1 | 59.7 ± 2.1 | |
| | 2.5 | 30.3 ± 0.6 | |
| | 5 | 6.7 ± 0.6 | |
| | 10 | 0.0 ± 0.0 | |
| UPCI:SCC | | | |
| SCC099 | 0 | 100.0 ± 0.0 | |
| | 1 | 58.0 ± 1.0 | |
| | 2.5 | 29.7 ± 1.5 | |
| | 5 | 5.7 ± 1.2 | |
| | 10 | 0.0 ± 0.0 | |
| SCC116 | 0 | 100 ± 0.0 | |
| | 1 | 55.0 ± 4.4 | |
| | 2.5 | 23.0 ± 2.6 | |
| | 5 | 6.0 ± 1.0 | |
| | 10 | 0.0 ± 0.0 | |
| SCC182 | 0 | 100 ± 0.0 | |
| | 1 | 56.0 ± 5.2 | |
| | 2.5 | 32.7 ± 4.0 | |
| | 5 | 9.3 ± 2.1 | |
| | 10 | 0.0 ± 0.0 | |
| No Amp No Loss | | | 100.0 ± 0.0 |
| | | | 56.3 ± 3.7 |
| | | | 28.4 ± 5.0 |
| | | | 7.0 ± 2.2 |
| | | | 0.0 ± 0.0 |
| SCC078 | 0 | 100 ± 0.0 | |
| | 1 | 83.0 ± 2.6 | |
| | 2.5 | 56.7 ± 0.6 | |
| | 5 | 38.0 ± 1.7 | |
| | 10 | 7.0 ± 0.0 | |
| SCC084 | 0 | 100 ± 0.0 | |
| | 1 | 80.7 ± 4.6 | |
| | 2.5 | 52.3 ± 5.0 | |
| | 5 | 24.7 ± 2.1 | |
| | 10 | 7.7 ± 0.6 | |
| SCC131 | 0 | 100 ± 0.0 | |
| | 1 | 86.7 ± 2.5 | |
| | 2.5 | 51.7 ± 3.8 | |
| | 5 | 37.3 ± 2.1 | |
| | 10 | 11.3 ± 2.5 | |
| SCC136 | 0 | 100 ± 0.0 | |
| | 1 | 81.7 ± 3.5 | |
| | 2.5 | 55.0 ± 4.6 | |
| | 5 | 34.7 ± 2.5 | |
| | 10 | 11.0 ± 1.0 | |
| Amp with Loss | | | 100.0 ± 0.0 |
| | | | 83.0 ± 3.8 |
| | | | 53.9 ± 3.9 |
| | | | 33.7 ± 5.9 |
| | | | 9.3 ± 2.3 |
| SCC104 | 0 | 100 ± 0.0 | |
| | 1 | 82.3 ± 4.7 | |
| | 2.5 | 55.3 ± 2.1 | |
| | 5 | 33.7 ± 1.2 | |
| | 10 | 7.7 ± 0.6 | |
| SCC122 | 0 | 100 ± 0.0 | |
| | 1 | 77.0 ± 1.0 | |
| | 2.5 | 54.7 ± 0.6 | |
| | 5 | 24.0 ± 1.7 | |
| | 10 | 4.0 ± 1.0 | |
| SCC142 | 0 | 100 ± 0.0 | |
| | 1 | 81.0 ± 4.0 | |
| | 2.5 | 51.7 ± 4.6 | |
| | 5 | 35.3 ± 1.5 | |
| | 10 | 9.7 ± 0.6 | |
| No Amp with Loss | | | 100.0 ± 0.0 |
| | | | 80.1 ± 4.0 |
| | | | 53.9 ± 3.1 |
| | | | 31.0 ± 5.5 |
| | | | 7.1 ± 2.6 |
| SCC125 | 0 | 100 ± 0.0 | |
| | 1 | 83.3 ± 5.0 | |
| | 2.5 | 40.3 ± 3.2 | |
| | 5 | 27.7 ± 0.6 | |
| | 10 | 0.7 ± 0.6 | |

Loss of Distal 11q in HNSCC is Associated with Reduced Sensitivity to IR (Radiosurvival). A clonogenic survival assay was used to determine the sensitivity of HNSCC to DNA damage induced by ionizing radiation (FIG. 28A-B, see also Table 15, above). Results for the assay in triplicate were grouped as "No Amplification No Loss" (UPCI:SCC099, 116 and 182), "Amplification with Loss" (UPCI:SCC078, 084, 131 and 136), and "No Amplification with Loss" (UPCI: SCC104, 122 and 142). Normal human oral keratinocytes (NHOK) were included as a control. UPCI:SCC125 was not included in the group analysis due to the heterogeneity in copy number revealed by FISH. In the grouped analysis, NHOK showed 59.7±2.1% survival at 1 Gy, and no survival at 10 Gy of IR. Similarly, the HNSCC cells with "No Amplification, No Loss" showed 56.3±3.7% survival at 1 Gy, and no survival at 10 Gy IR. Thus, the normal human oral keratinocytes (NHOK) and cell lines without 11q loss are sensitive to ionizing radiation. Conversely, the "Amplification with Loss" HNSCC cell lines had 83±3.8% survival at 1 Gy, and 9.3±2.3% survival at 10 Gy IR. The "No Amplification with Loss" cells had 80.1±4.0% survival at 1 Gy, and 7.1±2.6% survival after exposure to 10 Gy IR. The UPCI:SCC125 cells had a high surviving fraction after 1 Gy (83.3±5.0%), and a small, but visible surviving fraction at 10 Gy (0.7±0.6%). Thus, unexpectedly, the HNSCC cell lines with distal 11q loss ("Amplification and Loss" (UPCI:SCC078, 084, 131 and 136) and "No Amplification with Loss" (UPCI:SCC 104, 122 and 142)) demonstrate loss of sensitivity to ionizing radiation with a substantial proportion of cells surviving a usually lethal single fraction of 10 Gy IR (radiosurvival). The term radiosurvival is used to refer to the observation that 10% of HNSCC cells with 11q loss survive the dose of 10 Gy IR, whereas none of the control cells or HNSCC cells without 11q loss survive the same dose (Golding et al., 2004).

7.3 Discussion

Amplification of 11q13 occurs in about 45% of HNSCC and is associated with a poor prognosis. Previously, Roh and colleagues determined that 11q13 amplification was an early event in HNSCC development, at times appearing in dysplastic tissue (Roh et al., 2000). In the BFB cycle model of 11q13 amplification, distal 11q loss necessarily precedes 11q13 amplification and is therefore an earlier event in HNSCC tumorigenesis. While the amplification of genes in band 11q13 is thought to play an important role in the progression of HNSCC, the impact of the preceeding loss of genes on distal 11q has not been examined in detail. In addition to HNSCC, loss of distal 11q has been reported in a variety of tumors including breast carcinoma, esophageal carcinoma, cervical carcinoma and prostate cancer (Tomlinson et al., 1995; Dahiya et al., 1997; Evans et al., 1998; Jin et al., 1998, 2006; Matsumoto et al., 2004; Miyai et al., 2004; Wang et al., 2004). Genes encoding several proteins critical to the DNA damage response, including MRE11A, ATM and H2AFX, are located on distal 11q. Thus, loss of distal 11q may lead to defects in DNA damage recognition and repair and play a role in chromosomal instability and altered response to therapy in a variety of tumors.

The data presented herein confirms the loss of distal 11q in a large proportion of HNSCC by FISH (Table 12), LOH (FIG. 26) and QuMA. Loss of distal 11q in HNSCC was also shown by Jin et al. (1998, 2006). While LOH and QuMA showed segmental loss from approximately 11q14.2 to 11qter, FISH analysis directly demonstrated relative copy number loss of MRE11A, ATM, and H2AFX in a subset of our HNSCC cell lines. In addition to HNSCC cell lines, we observed relative loss of ATM copy number in all five primary head and neck tumors studied. Although at a lower frequency, ATM loss was also observed in at least 60% of a small, but unselected sample of ovarian and breast carcinomas.

In response to ionizing radiation, a reduction in γ-H2AX focus formation was observed in HNSCC cell lines with distal 11q loss irrespective of 11q13 amplification. These cell lines had considerably reduced mean numbers of foci after treatment with IR compared with normal controls or HNSCC cell lines without loss of distal 11q. This could result from either a reduction in H2AX protein present in the chromatin around DSBs, a reduction in the ATM kinase activity that phosphorylates H2AX after DNA damage or the disruption of substrate-kinase interactions. Since H2AX phosphorylation following IR is partially ATM-dependent, it is possible that the reduction in ATM protein, and perhaps concomitant reduction in activity, is responsible for the reduced number of foci. Given that γ-H2AX focus formation has been shown to be a valid assessment of continuity of elements in the DNA damage response (Rogakou et al., 1998; Paull et al., 2000), particularly those involved upstream in the recognition of strand breaks, the results above indicate that distal 11q loss is associated with a compromised DNA damage response.

Chromosomal breakage was examined following treatment with IR as a measure of chromosomal instability in HNSCC, and anaphase bridge formation in untreated HNSCC was calculated as a measure of baseline chromosomal instability. As shown in FIG. 7A-D and Table 14A, UPCI:SCC084 (Amplification with Loss) and UPCI:SCC104 (No Amplification with Loss) demonstrate a significant increase in the number of chromosome aberrations following IR. In comparison, UPCI:SCC116, which had no amplification or distal loss, did not demonstrate a significant increase in IR-dependent chromosomal aberrations. Thus, elevated chromosomal breakage levels correlate with 11q loss, partial insufficiency for MRE11A, ATM and H2AFX, and deficits in γ-H2AX focus formation. Anaphase bridges were found to be increased in the subset of cell lines with loss of distal 11q, regardless of 11q13 amplification (Table 14B). Cell lines without loss of distal 11q had frequencies similar to those of normal cells. In addition to being a hallmark of chromosomal instability, an increased incidence of anaphase bridges supports the BFB mechanism for gene amplification. It has been shown that mre11 and tefu (dATM) knockout mutants in Drosophila melanogaster exhibit a high frequency of telomere fusions, dicentric chromosomes and anaphase bridging (Bi et al., 2004; Ciapponi et al., 2004). The Drosophila dicentric chromosomes break and initiate breakage-fusion-bridge cycles, similar to the anaphase bridges and BFB cycles seen in HNSCC with distal 11q loss. Partial loss of MRE11A and ATM, as well as other genes, is thought to result from the deletion event that can precede BFB cycles, eventually leading to 11q13 amplification in HNSCC. Additional consequences for the cell result from amplification of CCND1 and the other genes in the 11q13 amplicon, including FADD, TAOS1, TAOS2, and EMS1 (Huang et al., 2002; Huang et al., 2006). The observations of BFB cycles as the primary mechanism of 11q13 amplification (Reshmi et al., 2007), as well as the observation of increased chromosomal instability in cell lines with 11q loss are strong evidence that loss of distal 11q is an important factor that precedes 11q13 gene amplification and may play a role in the development and/or progression of HNSCC.

Survival of the HNSCC cell lines following IR was investigated using a clonogenic survival assay. Since chromosome instability and deficits in γ-H2AX focus formation were observed following treatment with IR in HNSCC cell lines with 11q deletions, it had been expected that these cell lines would also be highly sensitive to ionizing radiation. Indeed, previous studies have shown that loss of ATM or MRE11A correlates with radiosensitivity (Gatti et al., 1991; Stewart et al., 1999; Prime et al., 2001). Surprisingly, it was found that loss of distal 11q in HNSCC is associated with radiosurvival, as 7-10% of cells in all tested HNSCC cell lines with distal 11q loss survived 10 Gy IR in a single fraction, whereas none of the control cells, including HNSCC cells without 11q loss, survived this dose of IR. Thus, counterintuitively, distal 11q loss appears to be associated with both chromosomal instability and radiosurvival. Mutations in TP53 between exons 5-9 are summarized in Table 12. Since there was equal representation of wild-type and mutant TP53 in all three groups of cell lines, TP53 alterations should not be responsible for the observed radiosurvival in the "Loss, No Amplification" and "Amplification with Loss" cells. Radiosurvival does not appear to be associated with loss of any specific gene on distal 11q, but there is a possibility that other undocumented differences in the cell lines may contribute to the observed deficiencies in the DNA damage response and the radiosurvival. Previous studies have postulated that inhibition of ATM kinase activity in tumors may increase the efficacy of radiotherapy and genotoxic chemotherapy in the treatment of TP53-mutant cancers (Westphal et al., 1998; Fedier et al., 2003). Without making any claims as to the nature of the TP53 mutations in the cell lines (Table 12), the evidence indicates that HNSCC cell lines, regardless of the presence of functional TP53, do not necessarily respond uniformly to ionizing radiation. The findings herein show that despite IR-dependent chromosomal instability and deficits in γ-H2AX focus formation, the HNSCC cell lines with 11q loss exhibit radiosurvival. This suggests that increased chromosomal damage in response to ionizing radiation may not predict radiosensitivity, and questions the efficacy of using an ATM-inhibitor in the treatment of HNSCC. The association between distal 11q loss and radiosurvival in cell lines may have direct translational implications for HNSCC patients, as aggressive radiation therapy may not be beneficial to patients with distal 11q loss.

Recently, a number of studies have shown that the DNA damage response protects against tumor formation, and that inactivation of components of the DNA damage response pathway may lead to chromosomal instability, uncontrolled cell proliferation and tumorigenesis (Bartkova et al., 2005; Gorgoulis et al., 2005). The data herein indicate that, along with CCND1 amplification, distal 11q loss is an early event in HNSCC tumorigenesis and promotes chromosomal instability. Since a number of HNSCC cell lines and the tumors from which they were derived are haploinsufficient for distal 11q, the remaining allele of MRE11A, ATM, H2AFX or other genes on distal 11q could undergo mutation or deletion leading to complete loss of function of the particular gene. Alternatively, it is possible that in a carrier of an ATM mutation, the normal allele could be deleted during tumor formation, resulting in absence of a functional allele. The data presented herein indicates that, following loss of distal 11q, the pathways that rely on the MRE11A, ATM, and H2AFX genes for DNA damage recognition and repair are compromised, and no longer function sufficiently to maintain chromosomal integrity. This loss of the normal DNA damage response appears to promote chromosomal instability and foster a genetic environment that selects for tumor cells with a growth advantage. Thus, loss of distal 11q in HNSCC appears to lead to chromosomal instability and contributes to tumor development, progression, and resistance to therapy.

8. EXAMPLE

Loss of Distal 11q in Carcinomas from Multiple Sites

8.1 Materials and Methods

Cell Culture. HNSCC cell lines, normal human oral keratinocytes (NHOK), and normal human fibroblasts were established in the inventors' laboratory. hTERT-transfected human oral keratinocytes were OKF6/TERT-1 from the laboratory of Dr. James G. Rheinwald; Dickson et al., 2000. GM09607, an ATM null cell line, was from Coriell Cell Repositories, Camden, N.J. The HNSCC cell lines were grown in Minimal Essential Medium (Gibco Invitrogen, Grand Island, N.Y.), supplemented with 1% non-essential amino acids, 1% L-glutamine, 0.05 mg/ml Gentamicin and 10% FBS) (all supplements from Gibco Invitrogen) (White, et al. 2007). NHOK established from uvulopalatopharyngoplasty specimens were cultured in serum-free KGM-2 medium (Clonetics, Walkersville, Md.), supplemented with BPE (bovine pituitary extract), hEGF, insulin (bovine), hydrocortisone, GA-1000 (Gentamicin, Amphotericin B), epinephrine and transferrin as per the manufacturer's instructions (supplements supplied in the KGM-2 BulletKit™ from Clonetics). Finite passage normal human fibroblasts established from uvulopalatopharyngoplasty tissue were cultured in Minimal Essential Medium (Gibco Invitrogen), supplemented with 1% non-essential amino acids, 1% L-glutamine, 0.05 mg/ml Gentamicin and 10% FBS) (Gibco Invitrogen). The OKF6/TERT-1 cells were initially cultured in Keratinocyte-SFM supplemented with 25 µg/ml bovine pituitary extract, 0.2 ng/ml epidermal growth factor, 0.3 mM CaCl2 and penicillin-streptomycin (Gibco Invitrogen). These keratinocytes were expanded to high density in a 1:1 mixture of Keratinocyte-SFM and DMEM-F12. The DMEM-F12 was a 1:1 mixture of calcium-free and glutamine-free DMEM and Ham's F-12 supplemented with 25 µg/ml bovine pituitary extract, 0.2 ng/ml epidermal growth factor, 1.5 mM L-glutamine and penicillin-streptomycin (Gibco Invitrogen). GM09607 (Coriell Cell Repositories, Camden, N.J.) was cultured in Dulbecco's Modified Eagle Medium (DMEM), supplemented with 1% non-essential amino acids, 0.05 mg/ml penicillin-streptomycin-L-glutamine, and 10% FBS (Gibco Invitrogen). Breast, lung, ovarian, and prostate cancer and multiple myeloma cell lines were obtained from various sources and grown under culture conditions recommended by the originator.

Fluorescence In Situ Hybridization (FISH). To prepare mitotic cells for FISH analyses, carcinoma cells were harvested following a 5 h treatment with 0.1 µg/ml Colcemid™ (Irvine Scientific, Santa Ana, Calif.), hypotonic KCl (0.075M) treatment for 16 min, and fixation in 3:1 methanol: glacial acetic acid. All other cells were harvested using the same method, except that 1 h of Colcemid™ was preferred for non-tumor cells. FISH analysis was used to detect copy number changes in the CCND1 and ATM genes in the cancer cell lines. For FISH analysis, cells were harvested, dropped onto slides, treated with RNase/2×SSC, and dehydrated using a graded series (70%, 80% and 100%) of ethanol washes. Chromatin was denatured with 70% formamide and the cells were dehydrated in a second graded series of ethanol washes. The CCND1 and ATM probes for FISH were prepared following DNA extraction from BACs purchased from Children's Hospital of Oakland Research Institute (CHORI, Oakland, Calif.). The BAC DNA was isolated and labeled using a nick translation kit from Vysis/Abbott Molecular Inc. (Des Plaines, Ill.). The labeled DNA was precipitated with ethanol, resuspended in hybridization buffer, denatured for 5 min at 75° C., and preannealed for 15-30 min at 37° C. Each probe was hybridized for 16 h at 37° C., after which slides were washed with SSC/Tween-20. Slides were counterstained with DAPI and mounted with antifade prior to analysis. All FISH analyses were carried out using an Olympus BX-61 epifluorescence microscope (Olympus Microscopes, Melville, N.Y.). An Applied Imaging CytoVision workstation with Genus v3.6 software was used for image capture and analysis (Applied Imaging, San Jose, Calif.).

Paraffin and Frozen Section FISH. Anonymous frozen sections of breast carcinomas and paraffin sections of the stage III ovarian carcinomas were obtained from the Magee-Womens Hospital Tissue Procurement Program. The paraffin sections of anonymous HNSCC were obtained from the Head and Neck SPORE Tissue Bank at the University of Pittsburgh. 4-5 µM thick sections of formalin-fixed, paraffin-embedded tissue were mounted on positively charged microscope slides. The slides were aged overnight at 60° C., following which they were deparaffinized twice with xylene for 5 min each at room temperature. The slides were dehydrated in two 100% ethanol washes, 2 min each at room temperature. The slides were then treated with 0.5×SkipDewax solution (Insitus Biotechnologies, Albuquerque, N. Mex.) at 80° C. for 15 min followed by a wash in distilled water for one min at room temperature, treatment in 0.2N HCl for 20 min at room temperature, pretreatment with 1 M sodium thiocyanate at 80° C. for 30 min, a wash in distilled water for one min at room temperature, two washes with 2×SSC 5 min each, and then treatment with protease (pepsin) solution for 15 min at 37° C. Next, the slides were fixed in 10% Formalin for 10 min at room temperature. After two 2×SSC washes at room temperature, the slides were dehydrated with a graded series of ethanol washes at room temperature, and allowed to dry on slide warmer. Next, slides were denatured at 75° C. in 70% formamide, followed by a cold series of ethanol washes. The probes for paraffin FISH were prepared as described for FISH above. The hybridization of the FISH probes and post-hybridization treatment of the paraffin sections was carried out as described for FISH above. 4-5 µM thick sections of OCT-embedded, fresh frozen breast carcinomas were mounted on positively charged microscope slides. The slides were placed in 0.8% sodium citrate for 20 min, fixed in 3:1 methanol acetic acid, and air dried. The slides were aged at 90° C. for 10 min, digested in 0.005% pepsin in 0.2N HCl at 37° C. for 60 sec, incubated in 70% ethanol for 30 sec, pretreated in 2×SSC at 37° C. for 60 min, dehydrated in a graded series of ethanol, denatured and hybridized as for FISH above.

8.2 Results and Discussion

Dual-color FISH with BAC probes to CCND1 and ATM were performed along with a centromere 11 enumeration probe in HNSCC (CEP 11; D11Z1) (Vysis/Abbott Molecular Inc.). Table 16, below, summarizes the FISH results. The copy number ratio of the ATM gene and the CCND1 gene was determined to be lost, gained, amplified or normal with respect to the centromere enumeration probe for chromosome 11. Arbitrary cut-off values of 15% were used for ATM loss and 10% for CCND1 amplification in paraffin sections.

The results show that distal 11q, marked by ATM is lost in 19 of 26 (73%) primary HNSCC examined and that CCND1 is amplified in 8 of 26 (31%) primary HNSCC. Primary ovarian tumors, reported first by Parikh et al. (Parikh, et al. 2007) showed loss of distal 11q in 2/10 (20%) and cyclin D1 amplification in 60%. Primary breast tumors showed loss in 29/68 (43%) and cyclin D1 amplification in 10/68 (15%). Loss of distal 11q with or without 11q13 amplification is seen in cell lines derived from HNSCC, ovarian, breast, prostate, and lung cancer cell lines and multiple myeloma cell lines.

The literature shows that cancer patients with ATM gene loss have a worse prognosis than those without ATM gene loss. Further, a recent study showed that the residual ATM allele is mutated in 36% of B-cell chronic lymphocytic leukemias (CLL) with a distal 11q deletion, and that these CLLs express a defective cellular response to ionizing radiation or cytotoxic drug exposure in vitro (Austen, et al. 2007). Further, these authors found that inactivation of the second ATM allele was associated with decreased survival beyond that already associated by an 11q deletion. In an immunohistochemistry study of the predictive value of molecular markers in squamous cell carcinoma of the esophagus, the authors found that tumors positive for ATM kinase phosphorylated at Ser1981 and CHK2 kinase phosphorylated at Thr68 (markers that were correlated with each other) responded to radiochemotherapy (45 Gy IR, cisplatin and 5-fluorouracil) with tumor regression and had better overall survival compared to tumors that were negative for CHK2 expression (Sarbia, et al. 2007). Another recent study of ATM expression in 70 gastric cancer specimens showed consistent decreased expression and phosphorylation of the protein and revealed that a low level of phosphorylated ATM was statistically significantly correlated with poor differentiation, lymph node metastasis, and poor 5-year survival (Kang, et al. 2008). Analysis of ATM expression in breast cancer showed that ATM expression levels in tumors were decreased by approximately 50% compared to adjacent normal mucosa (Ye, et al. 2007). Further, patients with the lowest tertile of ATM mRNA had less favorable disease-free survival and overall survival compared to patients in the upper two tertiles (Ye, et al. 2007). In a study that shows the importance of 11q loss in breast cancer, the protein expression of ATM and the MRE11/RAD50/NBS1 complex were examined by immunohistochemistry in tumors from 224 women with early breast cancer who were randomized to receive adjuvant chemotherapy or postoperative radiotherapy (Soderlund, et al. 2007). The authors found that the staining intensity of these four proteins was decreased in the majority of tumors compared to the staining of normal breast tissue. Weak expression of the MRN complex correlated with high histologic grade and estrogen receptor negativity. Importantly, the greatest benefit of radiotherapy was seen in patients with moderate/strong expression of the MRN complex, whereas patients with negative/weak MRN expression had no benefit of radiotherapy compared with adjuvant chemotherapy, suggesting that an intact MRN complex is critical to the tumor-cell killing effect of radiotherapy. These results all support the idea that the diminished DNA damage response resulting from distal 11q loss is associated with reduced sensitivity to IR and a worse prognosis in cancer patients.

A number of studies have shown that the DNA damage response protects against tumor formation, and that inactivation of components of the DNA damage response pathway may lead to chromosomal instability, uncontrolled cell proliferation and tumorigenesis (Bartkova, et al. 2005; Gorgoulis, et al. 2005). The results presented herein indicate that along with CCND1 amplification, distal 11q loss is an early event in tumorigenesis and promotes chromosomal instability. Since a number of cancer cell lines and the tumors from which they were derived are haploinsufficient for distal 11q, the remaining allele of MRE11A, ATM, H2AFX or other genes on distal 11q could undergo mutation or deletion leading to complete loss of function of the particular gene. Alternatively, it is possible that in a carrier of an ATM mutation, the normal allele could be deleted during tumor formation, resulting in absence of a functional allele. It has been demonstrated that, following loss of distal 11q, the pathways that rely on the MRE11A, ATM, and H2AFX genes for DNA damage recognition and repair are compromised, and no longer function sufficiently to maintain chromosomal integrity. This loss of the normal DNA damage response appears to promote chromosomal instability and foster a genetic environment that selects for tumor cells with a growth advantage. Thus, loss of distal 11q in cancer cells appears to lead to chromosomal instability and contributes to tumor development, progression, and resistance to therapy.

TABLE 16

Copy number alterations in CCND1 and ATM in tumors and cancer cell lines from various sites.

| | | FISH | | | | | | | |
| --- | --- | --- | --- | --- | --- | --- | --- | --- | --- |
| | | CCND1 | | | | ATM | | | |
| | | Percentage of cells with each copy number alteraiton | | | | | | | |
| Specimen Type | Sample ID | Loss | Normal | Gain | Amp | Loss | Normal | Gain | Amp |
| Breast cancer cell lines | T47-D | 1 | 81 | 18 | 0 | 4 | 91 | 5 | 0 |
| | MCF-7 | 1 | 50 | 49 | 0 | 93 | 7 | 0 | 0 |
| Multiple Myeloma | RPMI | 34 | 52 | 14 | 0 | 17 | 60 | 22 | 1 |
| | OPM2 | 0 | 62 | 38 | 0 | 42 | 54 | 4 | 0 |
| | U266 | 89 | 11 | 0 | 0 | 73 | 25 | 2 | 0 |
| | H929 | 84 | 15 | 1 | 0 | 77 | 20 | 77 | 0 |
| Lung cancer cell lines | 54T | 0 | 6 | 81 | 12 | 4 | 96 | 0 | 0 |
| | 84T | 0 | 0 | 83 | 16 | 87 | 11 | 0 | 0 |
| | 94T | 0 | 1 | 81 | 17 | 6 | 92 | 2 | 0 |
| | 98T | 0 | 73 | 27 | 0 | 22 | 78 | 0 | 0 |
| | 201T | 0 | 59 | 41 | 0 | 13 | 87 | 0 | 0 |
| | 253T | 0 | 78 | 22 | 0 | 93 | 7 | 0 | 0 |
| | 273T | 0 | 94 | 6 | 0 | 35 | 65 | 0 | 0 |
| | 343T | 0 | 88 | 9 | 3 | 0 | 25 | 75 | 0 |
| Ovarian cancer cell lines | OVCAR-3 | 27 | 55 | 17 | 0 | 3 | 97 | 0 | 0 |
| | ES-2 | 0 | 0 | 32 | 68 | 95 | 5 | 0 | 0 |
| | SKOV-3 | 4 | 89 | 6 | 0 | 100 | 0 | 0 | 0 |
| Ovarian Primary tumors | TP02-349 1A | 0 | 64 | 11 | 25 | 2 | 95 | 3 | 0 |
| | TP02-255 1E | 0 | 84 | 12 | 4 | 15 | 85 | 0 | 0 |
| | TP02-217 D | 0 | 93 | 5 | 2 | 3 | 97 | 0 | 0 |
| | TP02-238 2D | 0 | 88 | 8 | 4 | 54 | 41 | 5 | 0 |
| | TP02-500 7A | 0 | 68 | 16 | 16 | 0 | 53 | 5 | 42 |
| | TP02-545 1B | 0 | 66 | 12 | 22 | 5 | 79 | 10 | 6 |
| | TP02-628 3C | 0 | 82 | 12 | 6 | 42 | 51 | 7 | 0 |
| | TP02-539 1G | 0 | 53 | 31 | 16 | 2 | 87 | 11 | 0 |
| | TP02-505 2C | 0 | 5 | 14 | 81 | 7 | 93 | 0 | 0 |
| | TP02-236 2B | 0 | 70 | 17 | 13 | 0 | 11 | 0 | 89 |
| Prostate tumor cell lines | 1532T | 0 | 1 | 66 | 33 | 97 | 1 | 2 | 0 |
| | 1542T | 1 | 45 | 54 | 0 | 0 | 75 | 25 | 0 |
| | PC-3 | 2 | 96 | 2 | 0 | 15 | 85 | 0 | 0 |
| | PCC1 | 100 | 0 | 0 | 0 | 100 | 0 | 0 | 0 |
| | DU145 | 1 | 97 | 2 | 0 | 0 | 96 | 4 | 0 |
| | LAPC4 | 17 | 80 | 3 | 0 | 74 | 26 | 0 | 0 |
| | LNCap | 6 | 92 | 2 | 0 | 12 | 88 | 0 | 0 |
| Breast Primary tumors in OCT | TP98-2 | 3 | 89 | 8 | 0 | 7 | 93 | 0 | 0 |
| | TP98-15 | 2 | 91 | 7 | 0 | 8 | 90 | 2 | 0 |
| | TP98-63 | 3 | 92 | 5 | 0 | 9 | 89 | 2 | 0 |
| | TP98-84 | 0 | 91 | 9 | 0 | 7 | 89 | 4 | 0 |
| | TP98-98 | 0 | 72 | 26 | 2 | 8 | 92 | 0 | 0 |
| | TP98-102 | 1 | 94 | 5 | 0 | 4 | 95 | 1 | 0 |
| | TP98-130 | 0 | 91 | 9 | 0 | 6 | 94 | 0 | 0 |
| | TP98-146 | 0 | 79 | 21 | 0 | 17 | 82 | 1 | 0 |
| | TP98-155 | 0 | 89 | 11 | 0 | 18 | 81 | 1 | 0 |
| | TP98-167 | 3 | 94 | 3 | 0 | 6 | 94 | 0 | 0 |
| | TP98-175 | 0 | 93 | 7 | 0 | 8 | 92 | 0 | 0 |
| | TP98-176 | 11 | 61 | 23 | 5 | 48 | 52 | 0 | 0 |
| | TP98-182 | 0 | 42 | 12 | 47 | 18 | 80 | 2 | 0 |
| | TP98-206 | 0 | 98 | 2 | 0 | 5 | 95 | 0 | 0 |
| | TP98-221 | 0 | 34 | 0 | 66 | 51 | 48 | 1 | 0 |
| | TP98-230 | 3 | 95 | 2 | 0 | 32 | 64 | 4 | 0 |
| | TP98-237 | 9 | 84 | 7 | 0 | 12 | 86 | 2 | 0 |
| | TP98-258 | 11 | 80 | 9 | 0 | 1 | 97 | 1 | 1 |
| | TP98-268 | 2 | 95 | 3 | 0 | 4 | 94 | 2 | 0 |
| | TP98-276 | 36 | 64 | 0 | 0 | 49 | 51 | 0 | 0 |
| | TP98-279 | 0 | 4 | 6 | 90 | 23 | 77 | 0 | 0 |
| | TP98-280 | 0 | 94 | 6 | 0 | 8 | 91 | 1 | 0 |
| | TP98-290 | 13 | 70 | 15 | 2 | 18 | 82 | 0 | 0 |
| | TP98-298 | 17 | 73 | 8 | 2 | 10 | 87 | 3 | 0 |
| | TP98-299 | 2 | 79 | 18 | 2 | 7 | 91 | 2 | 0 |
| | TP98-310 | 2 | 22 | 17 | 59 | 44 | 55 | 1 | 0 |
| | TP98-322 | 0 | 16 | 9 | 75 | 24 | 76 | 0 | 0 |
| | TP98-323 | 0 | 38 | 62 | 0 | 57 | 43 | 0 | 0 |
| | TP98-324 | 11 | 89 | 0 | 0 | 1 | 93 | 6 | 0 |

TABLE 16-continued

Copy number alterations in CCND1 and ATM in tumors and cancer cell lines from various sites.

| | | FISH | | | | | | | |
|---|---|---|---|---|---|---|---|---|---|
| | | CCND1 | | | | ATM | | | |
| | | Percentage of cells with each copy number alteraiton | | | | | | | |
| Specimen Type | Sample ID | Loss | Normal | Gain | Amp | Loss | Normal | Gain | Amp |
| | TP98-334 | 0 | 90 | 10 | 0 | 7 | 93 | 0 | 0 |
| | TP98-342 | 0 | 91 | 9 | 0 | 5 | 95 | 0 | 0 |
| | TP98-350 | 0 | 94 | 6 | 0 | 10 | 89 | 1 | 0 |
| | TP98-355 | 0 | 97 | 3 | 0 | 6 | 94 | 0 | 0 |
| | TP98-376 | 3 | 89 | 8 | 0 | 5 | 93 | 2 | 0 |
| | TP98-391 | 0 | 93 | 7 | 0 | 10 | 90 | 0 | 0 |
| | TP98-410 | 0 | 90 | 10 | 0 | 9 | 91 | 0 | 0 |
| | TP98-411 | 1 | 88 | 11 | 0 | 6 | 94 | 0 | 0 |
| | TP98-412 | 0 | 87 | 13 | 0 | 23 | 76 | 1 | 0 |
| | TP98-418 | 1 | 94 | 5 | 0 | 8 | 92 | 0 | 0 |
| | TP99-31 | 3 | 86 | 11 | 0 | 9 | 91 | 0 | 0 |
| | TP99-33 | 0 | 93 | 7 | 0 | 8 | 92 | 0 | 0 |
| | TP99-36 | 0 | 4 | 2 | 94 | 22 | 77 | 1 | 0 |
| | TP99-39 | 0 | 89 | 11 | 0 | 9 | 90 | 1 | 0 |
| | TP99-46 | 1 | 90 | 9 | 0 | 5 | 95 | 0 | 0 |
| | TP99-51 | 0 | 5 | 4 | 91 | 30 | 70 | 0 | 0 |
| | TP99-52 | 8 | 80 | 12 | 0 | 6 | 86 | 8 | 0 |
| | TP99-60 | 3 | 81 | 16 | 0 | 8 | 88 | 4 | 0 |
| | TP99-65 | 0 | 82 | 18 | 0 | 10 | 90 | 0 | 0 |
| | TP99-71 | 0 | 31 | 69 | 0 | 46 | 54 | 0 | 0 |
| | TP99-74 | 0 | 86 | 14 | 0 | 9 | 90 | 0 | 0 |
| | TP99-83 | 4 | 79 | 17 | 0 | 18 | 80 | 2 | 0 |
| | TP99-84 | 2 | 93 | 5 | 0 | 4 | 96 | 0 | 0 |
| | TP99-85 | 15 | 71 | 13 | 0 | 25 | 73 | 2 | 0 |
| | TP99-88 | 18 | 43 | 35 | 4 | 24 | 76 | 0 | 0 |
| | TP99-89 | 11 | 78 | 11 | 0 | 41 | 52 | 7 | 0 |
| | TP99-96 | 17 | 67 | 17 | 0 | 6 | 86 | 9 | 0 |
| | TP99-98 | 2 | 15 | 54 | 3 | 65 | 35 | 0 | 0 |
| | TP99-99 | 38 | 50 | 11 | 2 | 14 | 84 | 2 | 0 |
| | TP99-106 | 0 | 4 | 30 | 65 | 72 | 28 | 0 | 0 |
| | TP99-109 | 16 | 64 | 20 | 0 | 22 | 65 | 12 | 0 |
| | TP99-110 | 4 | 84 | 12 | 0 | 11 | 88 | 1 | 0 |
| | TP99-111 | 0 | 0 | 4 | 96 | 16 | 84 | 0 | 0 |
| | TP99-117 | 0 | 93 | 7 | 0 | 7 | 93 | 0 | 0 |
| | TP99-118 | 12 | 86 | 0 | 0 | 62 | 38 | 0 | 0 |
| | TP99-130 | 5 | 87 | 8 | 0 | 46 | 52 | 0 | 1 |
| | TP99-134 | 0 | 50 | 25 | 25 | 54 | 45 | 1 | 0 |
| | TP99-137 | 0 | 95 | 5 | 0 | 38 | 62 | 0 | 0 |
| | TP99-146 | 0 | 81 | 19 | 0 | 22 | 78 | 0 | 0 |
| HNSCC Paraffin Primary tumors | 62097-4 1F | 2.0 | 58.0 | 31.0 | 9.0 | 28 | 72 | 0 | 0 |
| | 62139-5 3G | 2.0 | 62.0 | 22.0 | 14.0 | 58 | 40 | 2 | 0 |
| | 62141-8 C | 2.0 | 83.0 | 13.0 | 2.0 | 5 | 95 | 0 | 0 |
| | 62165-4 3K | 0 | 73 | 23 | 4 | 92 | 8 | 0 | 0 |
| | 62211-6 2F | 4 | 46 | 49 | 1 | 29 | 71 | 0 | 0 |
| | 62211-6 2G | 2 | 48 | 50 | 0 | 50 | 50 | 0 | 0 |
| | 62211-6 2H | 10 | 73 | 17 | 0 | 50 | 50 | 0 | 0 |
| | 62212-9 2O | 1 | 18 | 16 | 65 | 46 | 54 | 0 | 0 |
| | 62212-9 2P | 2 | 21 | 35 | 42 | 21 | 79 | 0 | 0 |
| | 62212-9 2Q | 2 | 24 | 17 | 57 | 37 | 63 | 0 | 0 |
| | 62220-0 1F | 3 | 93 | 4 | 0 | 0 | 100 | 0 | 0 |
| | 62220-0 1G | 8 | 85 | 7 | 0 | 2 | 98 | 0 | 0 |
| | 62224-2 2d | 3 | 91 | 6 | 0 | 10 | 90 | 0 | 0 |
| | 62224-2-2E | 14 | 72 | 14 | 0 | 15 | 85 | 0 | 0 |
| | 62224-2 2F | 3 | 94 | 3 | 0 | 0 | 100 | 0 | 0 |
| | 62233-6 1d | 6 | 71 | 23 | 0 | 25 | 75 | 0 | 0 |
| | 62233-6 1F | 2 | 95 | 3 | 0 | 29 | 71 | 0 | 0 |
| | 62237-8 83 | 7 | 85 | 8 | 0 | 0 | 100 | 0 | 0 |
| | 62237-8 8L | 7 | 84 | 9 | 0 | 11 | 89 | 0 | 0 |
| | 62261-1 2B | 1 | 64 | 19 | 16 | 32 | 68 | 0 | 0 |
| | 62262-4 3D | 11 | 89 | 0 | 0 | 38 | 62 | 0 | 0 |
| | 62262-4 3E | 12 | 82 | 6 | 0 | 86 | 14 | 0 | 0 |
| | 62262-4 3F | 11 | 89 | 0 | 0 | 62 | 38 | 0 | 0 |
| | 62265-3 6C | 0 | 9 | 7 | 84 | 69 | 31 | 0 | 0 |
| | 62265-3 6D | 0 | 10 | 3 | 87 | 2 | 98 | 0 | 0 |
| | 62265-3 6E | 2 | 17 | 3 | 78 | 5 | 95 | 0 | 0 |
| | 62272-1 3G | 0 | 32 | 11 | 57 | 7 | 93 | 0 | 0 |
| | 62272-1 3P | 0 | 28 | 5 | 67 | 91 | 9 | 0 | 0 |
| | 62273-4 1G | 7 | 87 | 6 | 0 | 4 | 96 | 0 | 0 |
| | 62273-4 1H | 4 | 93 | 3 | 0 | 73 | 27 | 0 | 0 |
| | 62273-4 1I | 8 | 83 | 9 | 0 | 3 | 97 | 0 | 0 |

TABLE 16-continued

Copy number alterations in CCND1 and ATM in tumors and cancer cell lines from various sites.

| | | FISH | | | | | | | |
|---|---|---|---|---|---|---|---|---|---|
| | | CCND1 | | | | ATM | | | |
| | | Percentage of cells with each copy number alteraiton | | | | | | | |
| Specimen Type | Sample ID | Loss | Normal | Gain | Amp | Loss | Normal | Gain | Amp |
| | 62280-2 2H | 8 | 86 | 6 | 0 | 9 | 91 | 0 | 0 |
| | 62280-2 2L | 6 | 90 | 4 | 0 | 3 | 97 | 0 | 0 |
| | 62295-4 1B | 3 | 85 | 12 | 0 | 45 | 55 | 0 | 0 |
| | 62297-0 1C | 17 | 63 | 20 | 0 | 12 | 88 | 0 | 0 |
| | 622970 1D | 8 | 79 | 11 | 2 | 1 | 98 | 1 | 0 |
| | 62298-3 1F | 3 | 86 | 11 | 0 | 4 | 96 | 0 | 0 |
| | 62298-3 1G | 7 | 86 | 7 | 0 | 0 | 100 | 0 | 0 |
| | 62300-5 6M | 5 | 86 | 9 | 0 | 84 | 16 | 0 | 0 |
| | 62300-5 6N | 7 | 83 | 10 | 0 | 38 | 59 | 3 | 0 |
| | 62300-5 6O | 6 | 81 | 13 | 0 | 1 | 79 | 20 | 0 |
| | 62302-1 8H | 0 | 58 | 4 | 38 | 28 | 72 | 0 | 0 |
| | 62302-1 8I | 0 | 52 | 3 | 45 | 13 | 85 | 2 | 0 |
| | 62306-3 1E | 4 | 79 | 17 | 0 | 19 | 81 | 0 | 0 |
| | 62306-3 1F | 16 | 79 | 5 | 0 | 0 | 100 | 0 | 0 |
| | 62315-7 4Q | 35 | 63 | 2 | 0 | 51 | 49 | 0 | 0 |
| | 62315-7 4R | 38 | 62 | 0 | 0 | 87 | 13 | 0 | 0 |
| | 62315-7 4S | 27 | 73 | 0 | 0 | 95 | 5 | 0 | 0 |
| | 62397-9 5K | 0 | 43 | 0 | 57 | 45 | 48 | 7 | 0 |
| | 62397-9 5Z | 4 | 88 | 8 | 0 | 81 | 19 | 0 | 0 |

Appendix A
List of Bacterial Artificial Chromosomes (BAC) and Centromere Enumeration Probes (CEP) Used for Fish Analysis

| Gene name | BAC ID | Fluorescent tag |
|---|---|---|
| ATM | CTD2047A4 | Spectrum Orange ™ |
| ATR | RP11-427D1 | Spectrum Green ™ |
| | RP11-383G6 | Spectrum Green ™ |
| CHEK1 | RP11-712D22 | Spectrum Orange ™ |
| CCND1 | RP11-699M19 | Spectrum Aqua ™ |
| H2AFX | RP11-892K21 | Spectrum Green ™ |
| MRE11A | RP11-685N10 | Spectrum Orange ™ |
| TP53 | RP11-199F11 | Spectrum Orange ™ |

All BACs were purchased from the Children's Hospital Oakland Research Institute (C.H.O.R.I.), Oakland, Calif. Two BACs RP11-427D1 and RP11-383G6 corresponding to the 5' and 3' ends of the ATR gene respectively were used simultaneously.

Appendix B
Sequences for ATR and CHEK1 siRNA

ATR and CHEK1 siRNAs were obtained from Dharmacon Inc. The individual sequences from the smartpool are outlined below:

ATR sequences:

(SEQ ID NO: 27)
GAACAACACUGCUGGUUUG GAAGUCAUCUGUUCAUUAU (SEQ ID NO: 28)
GAAAUAAGGUAGACUCAAU CAACAUAAAUCCAAGAAGA

CHEK1 sequences:

(SEQ ID NO: 29)
UAAAGUACCACACAUCUUGUU UAUUGGAUAUUGCCUUUCUU (SEQID NO: 30)
AUAUGAUCAGGACAUGUGGUU CCAUUGAUAGCCCAACUUCUU

APPENDIX C

LIST OF ANTIBODIES USED FOR IMMUNOBLOTTING

| Antibody | Type | Company | Concentration |
|---|---|---|---|
| Total ATR | Rabbit polyclonal | Affinity Bioreagents, Golden, CO. | 1:500-1:1000 |
| Total p53 (D-01) | Mouse monoclonal | Santa Cruz | 1:2000 |
| Total ATM | Rabbit polyclonal | Cell Signaling | 1:500 |
| Total CHEK1 | Rabbit polyclonal | Cell Signaling | 1:1000 |
| Total H2AX | Mouse monoclonal | Cell Signaling | 1:1000 |
| Total MRE11A | Goat polyclonal | Santa Cruz | 1:1000 |
| pATM (Ser 1981) | Rabbit polyclonal | Cell Signaling | 1:500 |
| pATR (Ser 428) | Mouse monoclonal | Cell Signaling | 1:500 |
| pBRCA1 (Ser 1497) | Goat polyclonal | Santa Cruz | 1:1000 |
| pCHEK1 (Ser 345) | Rabbit polyclonal | Cell Signaling | 1:1000 |
| pCHK2 (Thr 68) | Rabbit polyclonal | Cell Signaling | 1:1000 |
| pSMC1 (Ser 987) | Rabbit polyclonal | Cell Signaling | 1:1000 |
| pCDC25C (Ser 216) | Rabbit monoclonal | Cell Signaling | 1:1000 |
| γ-H2AX (Ser 139) | Mouse monoclonal | Upstate | 1:1000 |
| Actin | Mouse monoclonal | Sigma | 1:2000 |
| Tubulin | Rabbit polyclonal | Santa Cruz | 1:2000 |

APPENDIX D

Primer and probe sequences for QuMA and qRT-PCR analyses

| Gene | Forward (5'-3') | Reverse (5'-3') | Probe (5'-3') |
|---|---|---|---|
| MRE11A | GGAATTAGTGAAATACCAGTTGGAA (SEQ ID NO: 1) | CTCTGAAACGACGTACCTCCTCA (SEQ ID NO: 4) | 6-FAM-TTCTTAAAGAACGTCATATTGATGCCCTCGA-TAMARA (SEQ ID NO: 7) |

APPENDIX D -continued

Primer and probe sequences for QuMA and qRT-PCR analyses

| | | | |
|---|---|---|---|
| E2AX | CTCTGAAACGACGTACCTCCTCA (SEQ ID NO: 2) | CGCCCAGCAGCTTGTTG (SEQ ID NO: 5) | 6-FAM-CACCGCTGAGATCCTGGAGCTGG-TAMARA (SEQ ID NO: 8) |
| ATM | GGCGGCAGTGCTGGAGTA (SEQ ID NO: 3) | TTTTAACTTGGTTTTATGACAATTGCT (SEQ ID NO: 6) | 6-FAM-CTGCTCCTAATCCACCTCA TTTTCCATCGC-TAMARA (SEQ ID NO: 9) |

| Microsatellite | forward (5'-3') | Reverse (5'-3') |
|---|---|---|
| D11S4207 | TAGAGATCCCGTTCGACTTG (SEQ ID NO: 10) | GCTGGGTGTTACACAGGAC (SEQ ID NO: 11) |
| D11S787 | GTGGGCTTATTGTGGTAGTAGTC (SEQ ID NO: 12) | CAAGAGGAGGCAGGAGAGTC (SEQ ID NO: 13) |
| D11S1352 | TTTGTGAAATCTGAAGCACC (SEQ ID NO: 14) | TCCTTCATATCCTGAATCTCTG (SEQ ID NO: 15) |
| D11S901 | CCCACATAGATTACTGGCCTC (SEQ ID NO: 16) | ATTCCTACATTAGCAGTTGGCA (SEQ ID NO: 17) |
| D11S1887 | CTCCTCTGTATTCCCACAAAAC (SEQ ID NO: 18) | ACCTGACATTGTATCTAAACCTC (SEQ ID NO: 19) |
| D11S1358 | CTACAACCTGGATGAACCCTA (SEQ ID NO: 20) | AACCAACATTCTACTTTCTGTCT (SEQ ID NO: 21) |
| D11S917 | ATGATGCCATATCTTGTCTTGA (SEQ ID NO: 22) | AATTTAAAGACAGATGCCAAGC (SEQ ID NO: 23) |
| D11S1893 | CTAGTCCCTGGAACCTGGAT (SEQ ID NO: 24) | GGCTGATGTGGGCTTTTTCAA (SEQ ID NO: 25) |

9. References

Aaltonen, et al. (1993) *Science,* 260, 812-816.
Abraham (2001) *Genes Dev.* 15(17), 2177-96.
Åkervall, et al. (1997) *Cancer,* 79:3, 80-389.
Albertson, et al. (2003) *Nat Genet,* 34, 369-76.
Alnemri, et al. (1996) *Cell,* 87(2), 171.
Artandi, et al. (2000) *Nature,* 406(6796), 641-5.
Ashman, et al. (2003) *Br J Cancer,* 89(5), 864-9.
Austen, et all. (2007) *J. Clin. One.,* 25(34), 5448-57.
Bakkenist, et al. (2003) *Nature,* 421, 499-506.
Balz, et al. (2003) *Cancer Res.,* 63(6), 1188-91.
Bao, et al. (2004) *Oncogene.* 23(33), 5586-93.
Baocheng, et al. (2005) *Cancer Res,* 65(19), 8613-6.
Bartek, et al. (2004) *Nature Reviews Molecular Cell Biology,* 5, 792-804.
Bartek, et al. (2003) *Cancer Cell,* 3(5), 421-9.
Bartkova, et al. (2005) *Nature* 434, 864-870.
Bartkova, et al. (1995) *Cancer Res,* 55(4), 949-56.
Bassing, et al. (2003) *Cell,* 114(3), 359-70.
Bernard, et al. (1995) *Genes Chromosomes Cancer,* 13(2), 75-85.
Bernstein, et al. (2002) *Mutat Res.,* 511(2), 145-78.
Bi, et al. (2004) *Curr. Biol.,* 14, 1438-1353.
Blackburn (1991) *Nature,* 350, 569-73.
Bockmuhl, et al. (2000) *Am J Pathol.,* 157(2), 369-75.
Bockmuhl, et al. (2002) *Genes Chromosomes Cancer,* 33(1), 29-35.
Bockmuhl, et al. (1998) *Head Neck.,* 20(2):145-51.
Bodnar, et al. (1998) *Science.* 279(5349), 349-52.
Boffetta, et al. (2006) *Lancet Oncol.* 7(2), 149-56.
Bolt, et al. (2005) *Oral Oncol.,* 41, 1013-1020.
Broeks, et al. (2000) *Am. J. Hum. Genet.,* 66, 494-500.
Broker, et al. (2005) *Clin Cancer Res.,* 11(9), 3155-62.
Broustas, et al. (2004) *J Biol Chem.,* 279(25), 26780-8.
Brown, et al. (2003) *Genes Dev.,* 17(5), 615-28.
Brown (2005) *Alcohol,* 35, 161-168.
Bryan, et al. (1997) *Nature medicine,* 3, 1271-74.
Burma, et al. (2001) *J Biol Chem.,* 276(45), 42462-7.
Bursch, et al. (2000) *Ann N Y Acad Sci.,* 926, 1-12.
Busby, et al. (2000) *Cancer Res.,* 60(8), 2108-12.
Byun, et al. (2005) *Genes Dev.,* 19(9), 1040-52.
Cabral, et al. (2003) *J Biol Chem.,* 278(20), 17792-9.
Califano, et al. (1996) *Cancer Res.,* 56(11), 2488-92.
Califano, et al. (2000) *Clinical Cancer Res,* 6(2), 347-352.
Carnero, et al. (2000) *Nat Cell Biol.,* 2(3), 148-55.
Casper, et al. (2002) *Cell,* 111(6), 779-89.
Castedo, et al. (2004) *Oncogene,* 23(16), 2825-37.
Celeste, et al. (2003) *Cell,* 114(3), 371-83.
Chakrabarti, et al. (1991) *Indian J Med Sci.,* 45(10), 273-5.
Chang, et al. (1993) *Am J Gastroenterol.,* 88(2), 174-86.
Cheng, et al. (2005) *Cancer Res.,* 65(19), 8646-54.
Chin, et al. (1999) *Cell,* 97(4), 527-38
Chu (1997) *J Biol Chem.,* 272(39), 24097-100.
Ciapponi, et al. (2004) *Curr. Biol.,* 14, 1360-1366.
Cohen (1997) *Biochem J.,* 15, 326.
Cole, et al. (1992) *Science,* 258(5088), 1650-4.
Coquelle, et al. (1998) *Mol Cell,* 2(2), 259-65
Coquelle, et al. (1997) *Cell,* 89(2), 215-25.
Cortez, et al. (2001) *Science,* 294(5547), 1713-6.
Croce, et al. (1999) *J Clin Oncol.,* 17(5), 1618-24.
Cuadrado, et al. (2006) *J Exp Med.,* 203(2), 297-303.
Dahiya, et al. (1997) *Int. J. Cancer,* 72, 283-288
Dave, et al. (1992) *Cancer,* 70, 1017-23.
de Boer, et al. (2000) *Carcinogenesis,* 21(3), 453-60.
De Klein, et al. (2000) *Curr Biol.,* 10(8), 479-82.
De Villiers (1994) *Curr Top Microbiol Immunol,* 186, 1-12.
Dickson, et al. (2000) *Mol. Cell Biol.,* 20(4), 1436-1447.

Dillehay, et al. (1988) *NCI Monogr.*, (6), 173-6.
Elbashir, et al. (2001) *Nature*, 411, 494-98.
Enomoto, et al. (2004) *Oncogene*, 23(29), 5014-22.
Eshleman, et al. (1996) *Hum Mol Genet.*, 5 Spec No: 1489-94.
Evans, et al. (2004) *Head Neck*, 26(1), 63-70.
Evans, et al. (1998) *Oncogene*, 16, 2557-2264.
Fabian, et al. (1996) *J. Otolaryngol.* 25, 88-93.
Fedier, et al. (2003) *Ann Oncol.*, 14, 938-945.
Fesik (2005) *Nat Rev Cancer*, 5(11), 876-85.
Forastiere, et al. (2001) *N Engl J Med.*, 345(26), 1890-900.
Fracchiolla, et al. (1997) *Cancer*, 79, 1114-1121.
Smith, et al. (1999) *Genes Dev*, 13 916-934.
Gatti, et al. (1991) *Medicine (Baltimore)*, 70, 99-117.
Gillison, et al. (2000) *J Natl Cancer Inst.*, 92(9):709-20.
Gisselsson (2003) *Adv Cancer Res*, 87, 1-29.
Gisselsson, et al. (2002) *Br J Cancer*, 87(2), 202-7.
Goldenberg, et al. (2004) *Otolaryngol Head Neck Surg.*, 131(6), 986-93.
Golding, et al. (2004) *J. Biol. Chem.*, 279, 15402-15410.
Gollin (2001) *Head Neck*, 23, 238-53.
Gollin (2004) *Curr Opin Oncol.*, 25-31.
Gonzalez, et al. (2002) *Laryngoscope*, 112(3), 482-7.
Gorgoulis, et al. (2005) *Nature*, 434(7035), 907-13.
Graeber, et al. (1996) *Nature*, 379(6560), 88-91.
Graves, et al. (2000) *J Biol Chem.*, 275(8), 5600-5.
Guan, et al. (2004) *Cancer Res.*, 64(12), 4197-200.
Guan, et al. (2001) *Cancer Res.*, 61(9), 3806-9.
Ha, et al. (2003) *Crit Rev Oral Biol Med.*, 14(5), 363-9.
Hammond, et al. (2003) *J Biol Chem.*, 278(14), 12207-13.
Hammond, et al. (2004) *Cancer Res.*, 64(18), 6556-62.
Hanahan, et al. (2000) *Cell*, 100(1), 57-70.
Hefferin, et a (2005) *DNA Repair (Amst).*, 4(6), 639-48.
Hekmat-Nejad, et al. (2000) *Curr Biol.*, 10, 1565-1573.
Helt, et al. (2005) *J Biol Chem.*, 280(2), 1186-92.
Hemmer, et al. (2006) *Oncol Rep.*, 15(1), 243-6.
Heselmeyer, et al. (1996) *Proc Natl Acad Sci*, 93, 479-484.
Hickman, et al. (2002) *Curr Opin Genet Dev.*, 12(1), 60-6.
Ho, et al. (2004) *Crit Rev Oral Biol Med*, 15(4), 188-196.
Hoeijmakers (1994) *Eur J Cancer*, 30A(13), 1912-21.
Hoffelder, et al. (2004) *Chromosoma*, 112(8), 389-97.
Holm (1982) *Laryngoscope*, 92(9 Pt 1), 1064-9.
Huang, et al. (2006) *Genes Chromosomes Cancer*, 45, 1058-1069.
Huang, et al. (2002) *Proc Natl Acad Sci USA*, 99(17), 11369-74.
Huebner, et al. (2001) *Nat Rev Cancer*, 1(3), 214-21.
Igney, et al. (2002) *Nat Rev Cancer*, 2(4), 277-88.
Izzo, et al. (1998) *Oncogene*, 17(18), 2313-2322.
Jackson, et al. (2000) *Cancer Res.*, 60(3), 566-72.
Jackson (2001) *Biochem Soc Trans.*, 29(Pt 6), 655-61.
Jackson (2002) *Carcinogenesis*, 23(5), 687-96.
Janssen, et al. (2005) *Head Neck*, 27(7), 622-38.
Jarvinen, et al. (2006) *Oncogene PMID*, 16715129.
Jemal, et al. (2007) *CA Cancer J. Clin.*, 57, 43-66.
Jemal, et al. (2006) *CA Cancer J Clin.*, 56(2), 106-30.
Jin, et al. (2006) *Cytogenet Genome Res.*, 115, 99-106.
Jin, et al. (2002) *Cancer Genet Cytogenet.*, 132, 85-96.
Jin, et al. (2002) *Int J Cancer*, 98(3), 475-479.
Jin, et al. (1998) *Genes Chromosomes Cancer*, 22(4), 312-20.
Jiricny (2006) *Nat Rev Mol Cell Biol.*, 7(5) 335-46.
Jung, et al. (2006) *Mol Cancer Res.*, 4(3), 169-76.
Kalogeropoulos, et al. (2004) *Cell Cycle*, 3(9).
Kang, et al. (2008) *Mutat Res.*, 638(1-2), 17-25.
Kao-Shan, et al. (1987) *Cancer Res.*, 47(23), 6278-82.
Kastan, et al. (2004) *Nature*, 432(7015), 316-23.
Kawabe (2004) *Mol Cancer Ther.*, 4, 513-9.
Kaye, et al. (1993) *Proc Natl Acad Sci USA*, 90(19), 9150-4.
Kettunen, et al. (2000) *Cancer Genet Cytogenet.*, 117(1), 66-70
Khanna, et al. (2001) *Nat Genet.*, 27(3), 247-54.
Kim, et al. (2000) *Annu Rev Biochem.*, 69, 303-42.
Kim, et al. (1994) *Science*, 266(5193), 2011-5.
Kinzler, et al. (1996) *Nature*, 379(6560), 19-20.
Kunkel, et al. (2005) *Annu Rev Biochem.*, 74, 681-710.
Lane (1992) *Nature*, 358(6381), 15-6.
Lee, et al. (2004) *Science*, 304(5667), 93-6.
Lengauer, et al. (1998) *Nature*, 396(6712), 643-9.
Lese, et al. (1995) *Genes Chromosomes Cancer*, 12(4), 288-95.
Levi, et al. (1998) *Int J Cancer*, 77(5), 705-9.
Levine (1997) *Cell*, 88, 323-331.
Li, et al. (1994) *J Natl Cancer Inst.*, 86(20), 1524-9.
Li, et al. (1998) *Radiat Res.*, 149(4), 338-42.
Lichter, et al. (1994) *Methods Mol Biol*, 29, 449-478.
Liu, et al. (2000) *Genes Dev.*, 14(12), 1448-59.
Livingston, et al. (1990) *Environ Mol Mutagen*, 15(3), 136-44.
Llewellyn, et al. (2004) *Oral Oncol.*, 40(3), 304-13.
Loeb, et al. (2003) *Proc Natl Acad Sci USA*, 100(3), 776-81.
Lukas, et al. (2004) *DNA Repair (Amst).*, 3(8-9), 997-1007.
Lundberg, et al. (1999) *Eur J Cancer*, 35, 531-539.
Luo, et al. (2004) *Mutat Res*, 554(1-2), 375-85.
Lyman (1992) *Prim Care*, 19(3), 465-79.
Ma, et al. (2000) *Oncogene*, 19(23), 2739-44.
Mack, et al. (2004) *Radiat Res.*, 162(6), 623-34.
Macleod (2000) *Curr Opin Genet Dev.*, 10(1), 81-93.
Majumder, et al. (2005) *Cancer Epidemiol Biomarkers Prev.*, 14(9), 2106-12.
Maniwa, et al. (2005) *Cancer.*, 103(1), 126-32.
Mao, et al. (1996) *Nat Med.*, 2(6), 682-5.
Martin-Granizo, et al. (1997) *Otolaryngol Head Neck Surg.*, 117(3 Pt 1), 268-75.
Maser, et al. (2002) *Science*, 297(5581), 565-9.
Massague (2004) *Nature*, 432(7015), 298-306.
Matsumoto, et al. (2004) *Hum. Pathol.*, 35, 322-327.
McClintock (1938) *MO Agric Exp Sta Res Bull*, 290, 1-48.
McClintock (1939) *Proc Natl Acad Sci USA*, 25, 405-416.
McKaig, et al. (1998) *Head Neck*, 20(3), 250-65.
Meyn (1999) *Clin Genet.*, 55(5), 289-304.
Michalides, et al. (2002) *Head Neck*, 24(7), 694-704.
Michalides, et al. (1997) *Arch Otolaryngol Head Neck Surg.*, 123, 497-502.
Michalides, et al. (1995) *Cancer Res.*, 55, 975-978.
Mineta, et al. (2000) *Oral Oncol.*, 36, 194-198.
Miyai, et al. (2004) *Gynecol. Oncol.*, 94, 115-120.
Mohindra, et al. (2002) *Hum Mol Genet.*, 11(18), 2189-200.
Momand, et al. (1998) *Nucleic Acids Res.*, 26(15), 3453-9
Monni, et al. (1998) *Genes Chromosomes Cancer*, 21(4), 298-307.
Mork, et al. (2001) *N Engl J Med.*, 344(15), 1125-31.
Mumford, et al. (2006) *Tob Control*, 15(3), 166-71.
Munger, et al. (1992) *Cancer Surv.*, 12, 197-217.
Musk, et al. (1990) *Int J Radiat Biol.*, 57(6), 1105-12.
Nagao, et al. (2000) *Eur. J. Cancer*, 368:466.
Nakahara, et al. (2000) *Cancer Lett*, 160(1), 3-8.
Neville. et al. (2002) *CA Cancer J Clin.*, 52(4), 195-215.
Nevins (2001) *Hum Mol Genet.*, 10(7), 699-703.
Nghiem, et al. (2001) *Proc Natl Acad Sci USA*, 98(16), 9092-7.
Noguchi, et al. (2003) *Oncol Rep.* 10(5), 1393-400.
Nugent, et al. (1998) *Genes Dev.*, 12(8), 1073-85.

O'Connell, et al. (2005) *J Cell Sci.,* 118(Pt 1), 1-6.
O'Driscoll (2003) *Nat Genet.,* 33(4), 497-501.
Ogden (2005) *Alcohol,* 35, 169-173.
O'Hagan, et al. (2002) *Cancer Cell,* 2(2), 149-55.
Okada, et al. (2004) *Nat Rev Cancer,* 4(8), 592-603.
Parikh, et al. (2007) *Genes Chromosomes Cancer,* 46(8), 761-75.
Parkin, et al. (2005) *CA Cancer J Clin* 55, 74-108.
Parrilla-Castellar, et al. (2004) *DNA Repair (Amst).,* (8-9), 1009-14.
Paull, et al. (2000) *Curr. Biol.,* 10, 886-895.
Pei, et al. (2001) *Genes Chromosomes Cancer.* 31(3), 282-7.
Peltomaki (2003) *J Clin Oncol.,* 21(6), 1174-9.
Petti (2003) *Oral Oncol.,* 39(8), 770-80.
Phelps, et al. (1998) *Antivir Chem Chemother.,* 9(5), 359-77.
Poppe. et al. (2004) *Blood,* 103(1), 229-35.
Poschl, et al. (2004) *Alcohol Alcohol,* 39(3), 155-65.
Poschl, et al. (2004) *Proc Nutr Soc.,* 63(1), 65-71.
Prime, et al. (2001) *Oral Oncol.,* 37(1), 1-16.
Quintyne, et al. (2005) *Science,* 307(5706), 127-9.
Ragin, et al. (2004) *Int J Cancer,* 110(5), 701-9.
Redon, et al. (2002) *Cancer Res.,* 62(21), 6211-7.
Redon, et al. (2001) *Cancer Res.,* 61(10), 4122-9.
Reichart (2001) *Clin Oral Investig,* 5(4), 207-13.
Reshmi, et al. (2007) *Cytogenet Genome Res.,* 116, 46-52.
Reshmi, et al. (2005) *J Dent Res,* 84(2), 107-17.
Rhodus (2005) *Dent Clin North Am.,* 49(1), 143-65.
Riedl, et al. (2004) *Nat Rev Mol Cell Biol.,* 5(11), 897-907.
Rogakou, et al. (2000) *Biol. Chem.,* 275, 9390-9395.
Rogakou, et al. (1998) *J. Biol. Chem.* 273, 5858-5868.
Roh, et al. (2000) *Cancer Res.* 60, 6496-6502.
Sabatier, et al. (2005) *Mol Cancer Res.,* 3(3), 139-50.
Sanchez, et al. (1997) *Science,* 277(5331), 1497-501.
Sarbia, et al. (2007) *British Journal of Cancer,* 97(10), 1404-8.
Sarkaria, et al. (1999) *Cancer Res.,* 59(17), 4375-82.
Sartor, et al. (1999) *Br J Cancer,* 80(1-2), 79-86.
Sartor, et al. (1999) *Br J Cancer,* 80(1-2), 79-86.
Sattler, et al. (1999) *Prostate,* 39(2), 79-86.
Saunders, et al. (2000) *Proc Natl Acad Sci USA,* 97, 303-308.
Schantz, et al. (2002) *Arch Otolaryngol Head Neck Surg.,* 128(3), 268-74.
Schraml, et al. (1999) *Clin Cancer Res.,* 5, 1966-1975.
Schuuring, et al. (1998) *Cell Adhes Commun.,* 6, 185-209.
Schuuring, et al. (1992) *Oncogene,* 7(2), 355-361.
Schuuring (1995) *Gene,* 159(1), 83-96.
Seitz, et al. (1998) *Recent Dev Alcohol,* 14:67-95.
Seitz, et al. (2002) *Nutritional Toxicology,* 2nd edn, 122-154.
Serrano, et al. (1996) *Cell,* 85(1), 27-37.
Shao, et al. (1997) *Cancer Res.,* 57(18), 4029-35.
Sherr, et al. (2002) *Cancer Cell,* 2(2):103-12.
Sherr (1998) *Genes Dev.,* 12(19), 2984-91.
Shiloh (2001a) *Curr Opin Genet Dev,* 11(1):71-7.
Shiloh (2001b) *Nat Rev Cancer,* 3(3):155-68.
Shiloh, (2003) *Cell Cycle,* 2(2), 116-7.
Shintani, et al. (2001) *Oral Oncol.,* 37(6), 498-504.
Shiu, et al. (2004) *Eur J Cancer Prev.,* 13(1), 39-45.
Shuster, et al. (2000) *Genes Chromosomes Cancer,* 28(2), 153-63.
Sidransky (1995) *Curr Opin Oncol,* 7(3), 229-33.
Silverman (2001) *J Am Dent Assoc.,* 132:7 S-11S.
Singh, et al. (2002) *Am J Pathol.,* 161(2), 365-71.
Siprashvili, et al. (1997) *Proc Natl Acad Sci USA,* 94(25), 13771-6.
Smith, et al. (1999) *Genes Dev.,* 13(8), 916-34.
Smith, et al. (1998) *Nat Genet,* 19(1), 39-46.
Soderlund, et al. (2007) *Int. J. Rad. Onco., Bio., Phys.,* 68(1), 50-8.
Spitkovsky, et al. (2002) *J Biol Chem.,* 277(28), 25576-82.
Stein, et al. (2002) *Genes Chromosomes Cancer,* 34(3), 333-40.
Stell (1991) *Head Neck,* 13(4), 277-81.
Stewart, et al. (1999) *Cell,* 99, 577-587.
Stich, et al. (1992) *Int J Cancer,* 50(2), 172-6.
Sticht, et al. (2005) *Br J Cancer,* 92(4), 770-4.
Stoltzfus, et al. (2005) *Int J Gynecol Cancer,* 15(1), 120-6.
Storz (2005) *Front Biosci.,* 10, 1881-96.
Stracker, et al. (2004) *DNA Repair(Amst).,* 3(8-9), 845-54.
Sudbo, et al. (2002) *JCO,* 20, 456-462.
Sweasy, et al. (2006) *Cell Cycle,* 5(3), 250-9.
Syljuasen, et al. (2005) *Mol Cell Biol.,* 25(9), 3553-62.
Takai, et al. (2000) *Genes Dev.,* 14(12), 1439-47.
Telmer, et al. (2003) *Hum Mutat.,* 2, 158-65.
Thelen, et al. (1999) *Cell.* 96(6), 769-70.
Theunissen, et al. (2003) *Mol Cell,* 12(6), 1511-23.
Tibbetts, et al. (1999) *Genes Dev.,* 13(2), 152-7.
Tomar (2003) *Am J Med Sci.,* 326(4), 248-54.
Tomlinson, et al. (1995) *J. Clin. Pathol.,* 48, 424-428.
Trujillo, et al. (1998) *J Biol Chem.,* 273(34), 21447-50.
Tsuchiya, et al. (1998) *Anticancer Res,* 18(1B), 657-66.
Tsuchiya, et al. (1998) *Anticancer Res.,* 18(1B), 657-66.
Van Dyke, et al. (1994) *Genes Chromosomes Cancer,* 9, 192-206.
Vaupel, et al. (2001) *Semin Oncol.,* 28(2 Suppl 8), 29-35.
Vaziri, et al. (1998) *Curr Biol.,* 8(5), 279-82.
Virgilio, et al. (1996) *Proc Natl Acad Sci USA,* 93(18), 9770-5.
Voorhoeve, et al. (2003) *Cancer Cell,* 4(4), 311-9.
Wall, et al. (2003) *Lancet,* 5; 362(9393), 1401-3.
Wang, et al. (2004) *Cancer Res.,* 64, 64-71.
Wang, et al, (2003) *J Biol Chem.,* 278(33), 30869-74.
Ward, et al. (2001) *J Biol Chem.,* 276(51), 47759-62.
Weinberg (1995) *Cell,* 5; 81(3):323-30.
Werness, et al. (1990) *Science,* 248(4951), 76-9.
Westphal, et al. (1998) *Cancer Res.,* 58, 5637-5639.
White, et al. (2007) *Oral Onco.,* 43(7), 701-12/
Wood, et al. (2001) *Science,* 291(5507), 1284-89.
Wood (1997) *J Biol Chem,* 272(38), 23465-8.
Xu, et al. (2001) *Mol Cell Biol,* 21(10), 3445-50.
Yabro (1992) *Semin Oncol Nurs.,* 8(1), 30-9.
Yancik (2005) *Cancer J,* 11(6), 437-41.
Yang, et al. (2001) *Cancer Genet Cytogenet,* 131(1), 48-53.
Ye, et al. (2007) *Cancer,* 109(9), 1729-35.
Yeh, et al. (2003) *Oncol Rep,* 10(3), 659-63.
Young, et al. (2004) *Nat Rev Cancer,* 4(10), 757-68.
Yu, et al. (2004) *Curr Opin Oncol.,* 16(1), 19-24.
Zatkova, et al. (2004) *Genes Chromosomes Cancer,* 39(4), 263-76.
Zhao, et al. (2002) *J Biol Chem.,* 277(48), 46609-15.
Zhivotovsky, et al. (2004) *Nat Rev Mol Cell Biol,* 5(9), 752-62.
Zhou, et al. (2003) *Cancer Biol Ther.,* 2(4 Suppl 1), S16-22.
Zhou, et al. (2003) *Prog Cell Cycle Res,* 5, 413-21.
Zou, et al. (2003). *Science,* 300(5625), 1542-8.

Various publications are cited herein, the contents of which are hereby incorporated by reference in their entireties.

We claim:

1. A method of identifying a patient suffering from a cancer which is likely to be refractory to radiation therapy comprising:
   (i) identifying an 11q deletion in a patient sample considered to be representative of the cancer by a method selected from the group consisting of fluorescence in situ hybridization, quantitative microsatellite analysis, and loss of heterozygosity analysis;
   (ii) identifying, in the patient sample, overexpression of a gene selected from the group consisting of ATR, CEK1, CCND1, and a combination thereof by a method selected from the group consisting of quantitative reverse transcriptase PCR, Western blot, and fluorescence in situ hybridization; and
   (iii) identifying, in the patient sample, a decrease or absence of p53 expression and/or activity by a method selected from the group consisting of quantitative reverse transcriptase PCR and Western blot,
   wherein an 11q deletion, overexpression of ATR, CHEK1, CCND1, or a combination thereof, and a decrease or absence of p53 expression and/or activity indicates that the cancer is likely to be refractory to radiation therapy and may benefit from inhibition of the ATR/CHEK1 pathway, wherein the cancer is selected from the group consisting of head and neck squamous cell carcinoma, breast carcinoma, ovarian carcinoma, lung carcinoma, multiple myeloma cancer, and prostate cancer.

2. A method of treating a patient suffering from a cancer selected from the group consisting of head and neck squamous cell carcinoma, breast carcinoma, ovarian carcinoma, lung carcinoma, multiple myeloma cancer, and prostate cancer, comprising (i) identifying the patient as being likely to benefit from inhibition of the ATR/CHEK1 pathway by a method comprising:
   (a) identifying an 11q deletion in a patient sample considered to be representative of the cancer by a method selected from the group consisting of probe hybridization, fluorescence in situ hybridization, quantitative microsatellite analysis, PCR, quantitative DNA PCR, loss of heterozygosity analysis, array comparative genomic hybridization, and karyotype analysis,
   (b) identifying, in the patient sample, overexpression of a gene selected from the group consisting of ATR, CHEK1, CCND1, and a combination thereof by a method selected from the group consisting of antibody-binding, probe hybridization, quantitative real-time PCR, quantitative reverse transcriptase PCR, Northern blot, immunohistochemistry, fluorescence in situ hybridization, and Western blot, and
   (c) identifying, in the patient sample, a decrease or absence in p53 expression and/or activity by a method selected from the group consisting of antibody-binding, probe hybridization, quantitative real-time PCR, quantitative reverse transcriptase PCR, Northern blot, immunohistochemistry, fluorescence in situ hybridization, and Western blot, wherein an 11q deletion, overexpression of ATR, CHEK1, CCND1, or a combination thereof, and a decrease or absence in p53 expression and/or activity indicates that the cancer is likely to benefit from inhibition of the ATR/CHEK1 pathway; and
   (ii) treating the patient with an inhibitor of the ATR/CHEK1 pathway.

3. The method of claim 1, wherein the cancer is oral squamous cell carcinoma.

4. The method of claim 1, wherein overexpression of ATR is identified.

5. The method of claim 1, wherein overexpression of CHEK1 is identified.

6. The method of claim 1, wherein overexpression of CCND1 is identified.

7. The method of claim 2, wherein the cancer is oral squamous cell carcinoma.

8. The method of claim 2, wherein overexpression of ATR is identified.

9. The method of claim 2, wherein overexpression of CHEK1 is identified.

10. The method of claim 2, wherein overexpression of CCND1 is identified.

* * * * *